US006495666B2

(12) United States Patent
Shitara et al.

(10) Patent No.: US 6,495,666 B2
(45) Date of Patent: *Dec. 17, 2002

(54) POLYPEPTIDE COMPOSING HUMAN CHIMERIC ANTIBODY

(75) Inventors: Kenya Shitara, Tokyo (JP); Nobuo Hanai, Kanagawa (JP); Mamoru Hasegawa, Kanagawa (JP); Hiromasa Miyaji, Tokyo (JP); Yoshihisa Kuwana, Munich (DE)

(73) Assignee: Kyowa Hakko Kogyo Co., Ltd. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/764,304

(22) Filed: Jan. 19, 2001

(65) Prior Publication Data

US 2002/0026036 A1 Feb. 28, 2002

Related U.S. Application Data

(62) Division of application No. 09/225,322, filed on Jan. 5, 1999, which is a division of application No. 08/454,680, filed on May 31, 1995, now Pat. No. 5,866,692, which is a division of application No. 08/408,133, filed on Mar. 21, 1995, now Pat. No. 5,750,078, which is a continuation of application No. 08/292,178, filed on Aug. 17, 1994, now abandoned, which is a continuation of application No. 07/947,674, filed on Sep. 17, 1992, now abandoned.

(30) Foreign Application Priority Data

Sep. 18, 1991 (JP) .............................................. 3-238375

(51) Int. Cl.$^7$ ............................................. C07K 14/00

(52) U.S. Cl. ................. 530/350; 530/387.1; 530/388.8; 530/388.85

(58) Field of Search ............................... 530/350, 387.1, 530/387.3, 388.1, 388.8, 388.85; 424/130.1, 133.1, 135.1; 514/2

(56) References Cited

U.S. PATENT DOCUMENTS

| | | | |
|---|---|---|---|
| 4,849,509 A | 7/1989 | Thurin et al. | |
| 5,750,078 A | 5/1998 | Shitara | |
| 5,866,692 A | 2/1999 | Shitara et al. | |

FOREIGN PATENT DOCUMENTS

| | | |
|---|---|---|
| EP | 0 171 496 | 2/1986 |
| EP | 0 173 494 | 3/1986 |
| EP | 0 239 400 | 9/1987 |
| EP | 0 255 694 | 2/1988 |
| EP | 0 266 663 | 5/1988 |
| EP | 0 267 615 | 5/1988 |
| EP | 0 314 161 | 5/1989 |
| EP | 0 332 879 | 9/1989 |
| EP | 0 493 686 | 7/1992 |
| JP | 60-258128 | 12/1985 |
| WO | WO 86/01533 | 5/1986 |
| WO | 9109967 | 7/1991 |

OTHER PUBLICATIONS

R. O. Dillman et al., "Therapy of Chronic Lymphocytic Leukemia and Cutaneous T–Cell Lymphoma With T101 Monoclonal Antibody" J. Clin. Oncol., 2, 881, 1984.
A. F. LoBugulio et al., "Phase I Trial of Multiple Large Doses of Murine Monoclonal Antibody CO17–1A" J. Nat. Cancer Institute, 80, 932, 1988.
A. N. Houghton et al., "Mouse monoclonal IgG3 antibody detecting GD3 ganglioside: A phase I trial in patients with malignant melanoa", Proc. Natl. Acad. Sci. USA, 82, 1242, 1985.
M. B. Khazaeli et al., "Phase I Trial of Multiple Large Doses of Murine Monoclonal antibody CO17–1A" J. Nat. Cancer Institute, 80, 937, 1987.
N. S. Courtenay–Luck et al., "Development of Primary and Secondary Immune Responses to Mouse Monoclonal Antibodies used in the Diagnosis and Therapy of Malignant Neoplasms" Cancer Res. 46, 6489, 1986.
A. F. LoBuglio et al., "Mouse/human chimeric monoclonal antibody in man: Kinetics and immune response" Proc. Natl. Acad. Sci. USA, 86, 4220, 1989.
B. M. Mueller et al., "Enhancement of Antibody–Dependent Cytotoxicity With A Chimeric Anti–GD2 Antibody" J. Immuno., 144, 1382, 1990.
C.S., Pukel et al., GD3, A Prominent Ganglioside of Human Melanoma J. Exp. Med., 155, 1133, 1982.
E. Nudelman et al., Characterization of a Human Melanoma–associated Ganglioside Antigen Defined by a Monoclonal Antibody, 4.2% J. Biol. Chem. 257, 12752, 1982.
J. A. Werkmeister et al., "Fluctuations in the Expression of an Glycolipid Antigen Associated with Differentiation of Melanoma Cells Monitored by a Monoclonal Antibody, Leo Mel 3" Cancer Res. 47, 225, 1987.
M.–Y. Yeh et al.. "A Cell–Surface Antigen Which is Present in the Ganglioside Franction and Shared By Human Melanomas" Int. J. Cancer, 29, 269, 1982.
S. L. Morrison et al., "Chimeric human antibody molecules: Mouse antigen–binding domains with human constant region domains" Proc. Natl. Acad. Sci. USA, 81, 6851, 1984.*
K. Kameyama et al., "Convenient plasmid vectors for construction of chimeric mouse/human antibodies" FEBS Letters, 244, 301, 1989.*
S. D. Gillies et al., "High–level expression of chimeric antibodies using adapted cDNA variable region cassettes" J. Immunol. Method, 125 191, 1989.*

(List continued on next page.)

Primary Examiner—Sheela Huff
Assistant Examiner—Larry R. Helms
(74) Attorney, Agent, or Firm—Nixon & Vanderhye P.C.

(57) ABSTRACT

A humanized chimera antibody, a pharmaceutical composition comprising a humanized chimera antibody and a pharmaceutically acceptable carrier, and a method of treating cancer which comprises administering to a patient a pharmaceutically acceptable amount of the humanized chimera antibody, are disclosed.

2 Claims, 30 Drawing Sheets

OTHER PUBLICATIONS

L. Reichmann et al., "Reshaping human antibodies for therapy" Nature, 332, 323, 1988.*

H. Miyaji et al., "Expression of human beta–interferon in Namalwa KJM–1 which was adapted to serum–free medium" Cytotechnology, 3, 133, 1990.*

T. Mizukami et al., "A New SV40–Based Vector Developed for cDNA Expression in Animal Cells" J. Biochem. 101, 1307, 1987.*

Y. Kuwana et al., "Expression of Chimeric Receptor Composes of Immunoglobulin–Derived V Resions and T–Cell Receptor–Derived C Regions" Biochem. Biophys. Res. Commun., 149, 960, 1987.*

Y. Kuwana et al., "Production of the constant domain of murine T–cell receptor β–chain in *Escherichia coli*" FEBS Letters, 219, 360, 1987.*

S. Subramani et al., "Expression of the Mouse Dihydrofolate Reductase Complementary Deoxyribonucleic Acid in Simian Virus 40 Vectors" Mol. Cell. Biol. 1, 854, 1981.*

W. Roeder et al., "Linkage of the four γ subclass heavy chain genes" Proc. Natl. Acad. Sci. USA, 78 474, 1981.*

H. Sakano et al., "Sequences at the somatic recombination sites of immunoglobulin light–chain genes" Nature, 280, 288, 1979.*

Barker et al., "Effect of a Chimeric Anti–Ganglioside GC2 Antibody on Cell–mediated Lysis of Human Neuroblastoma Cells", Cancer Research 51(1):1440149 (1991).*

Ritter et al., "Antibody Response to Immunization with Purified GD3 Ganglioside and GD3 Derivatives (Lactones, Amide and Gangliosidol) in the Mouse", Immunobiol. 182(1):32–43 (1990).*

Waldmann Science 252:1657–1661 1991.*

Harris et al., TiB Tech 11:42–44 1993.*

Queen et al., PNAS 86:10029–1033 1989.*

Sonnino et al., The Molecular Immunology of Complex Charbohydrates Eds Wu & Adams Plenum Press New York 437–464 1988.*

Paul, Fundamental Immunology, Chapter 8, p. 242., 1993.*

* cited by examiner

FIG. 5
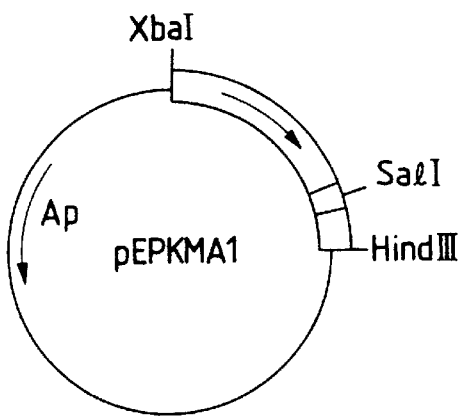
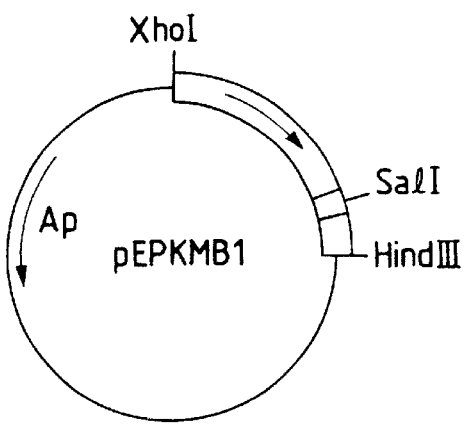
FIG. 7
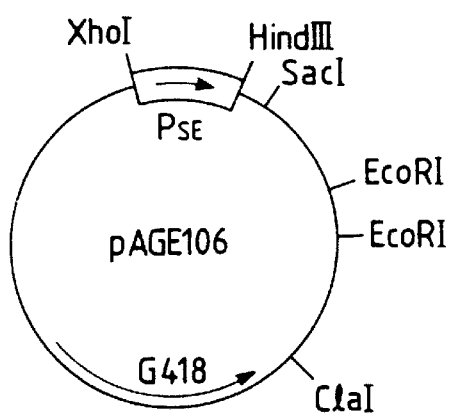
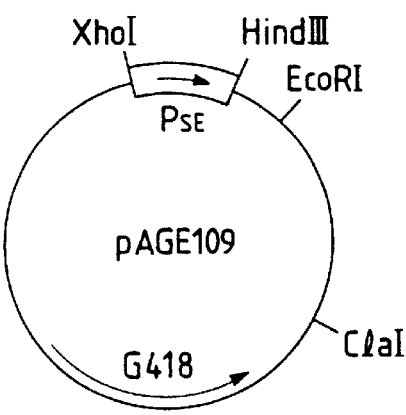

FIG. 11
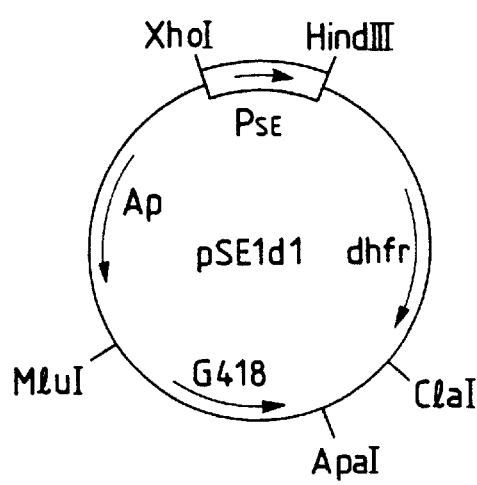
↓ HindIII
  Klenow polI
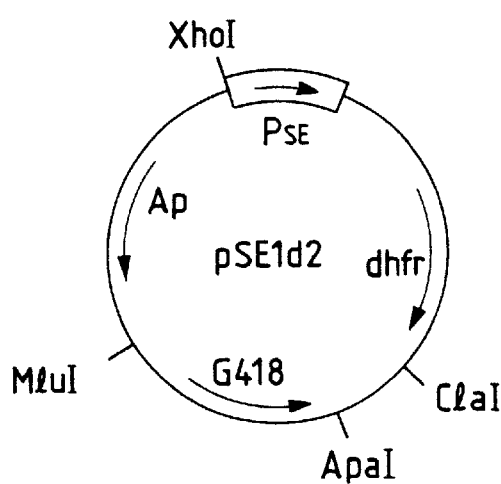
FIG. 13
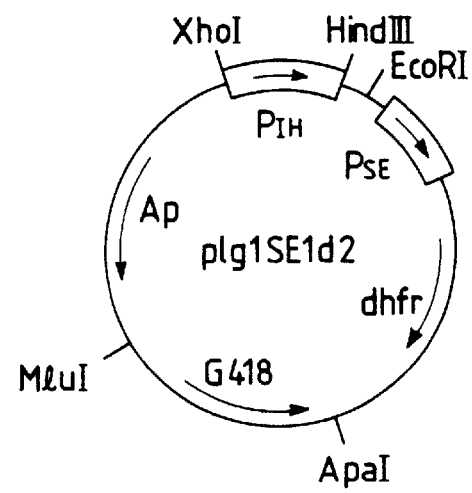
↓ ApaI
  Klenow polI
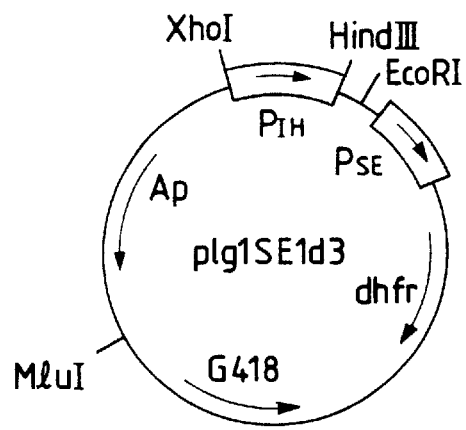

FIG. 15
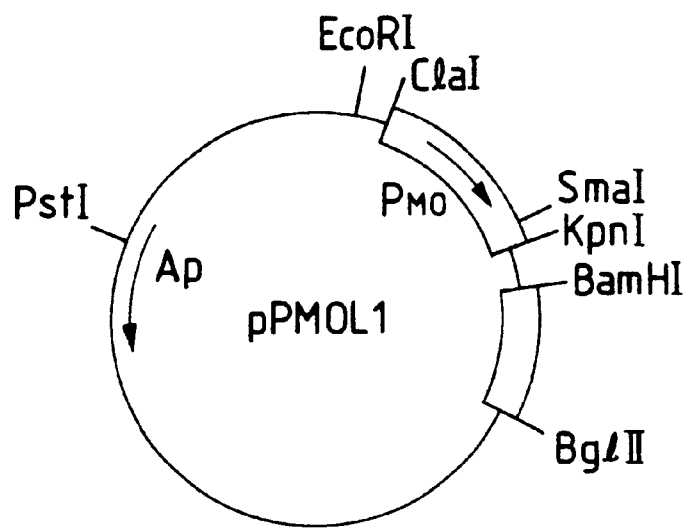
ClaI
Klenow polI
XhoI linker pCCTCGAGG
GGAGCTCCp
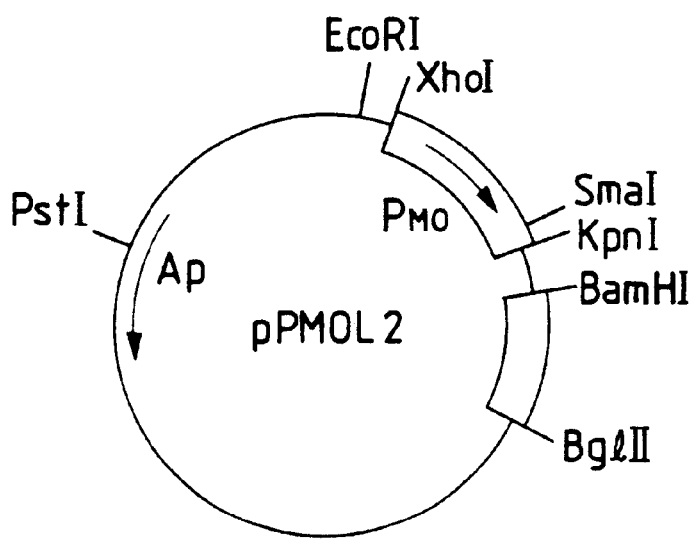

FIG. 16
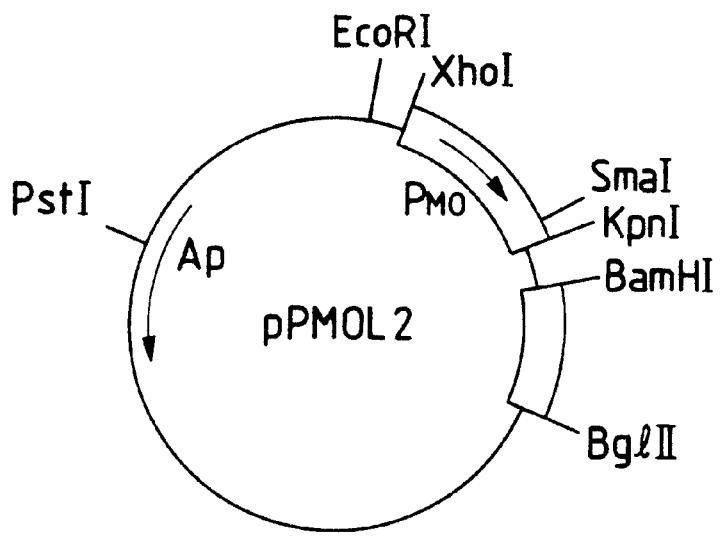
SmaI
EcoRI linker  pGGAATTCC
              CCTTAAGGp
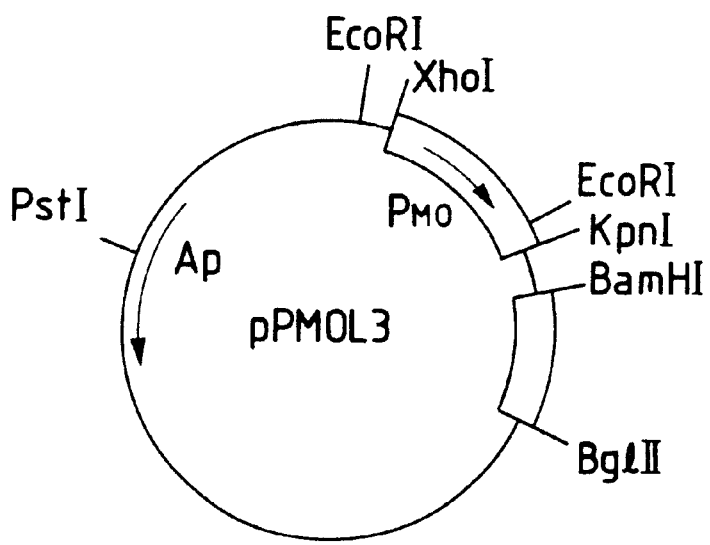

FIG. 18
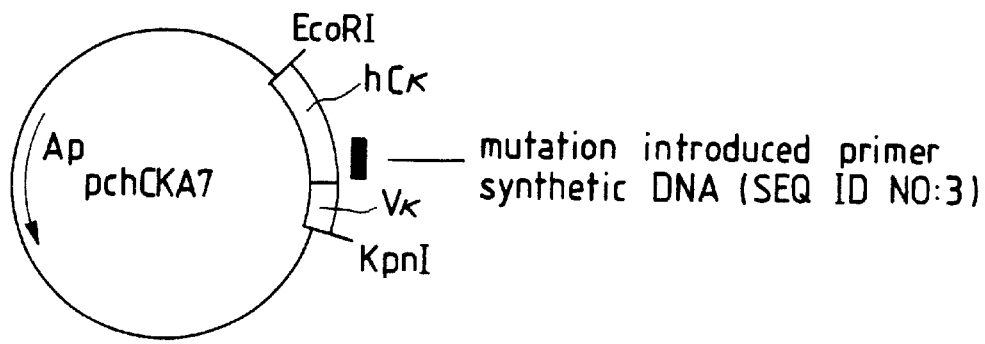
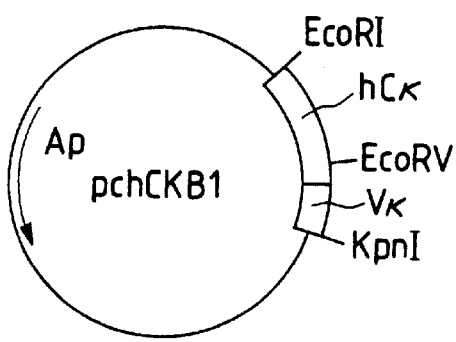

FIG. 19
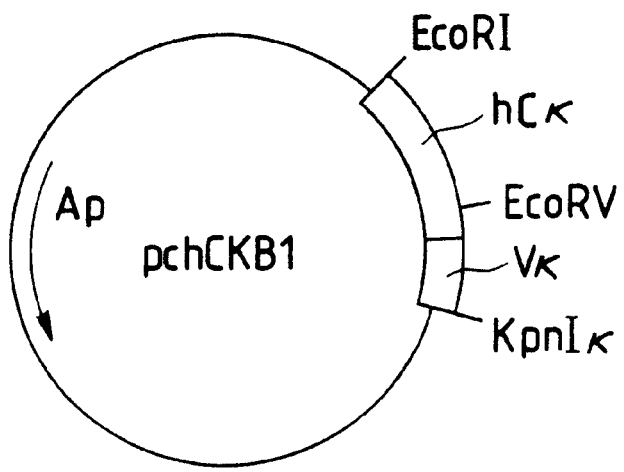
EcoRI
Klenow polI
HindIII linker  pCAAGCTTG
                 GTTCGAACp
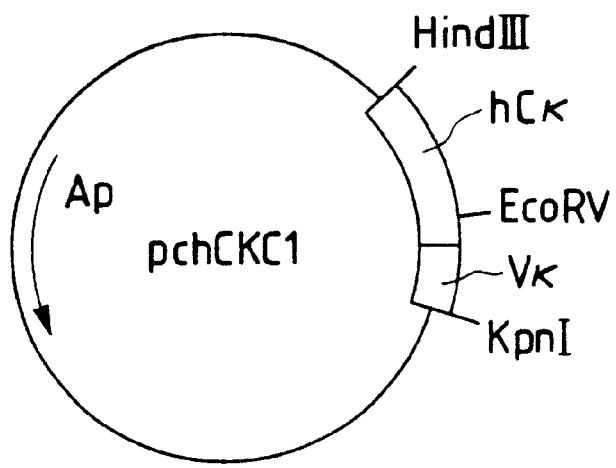

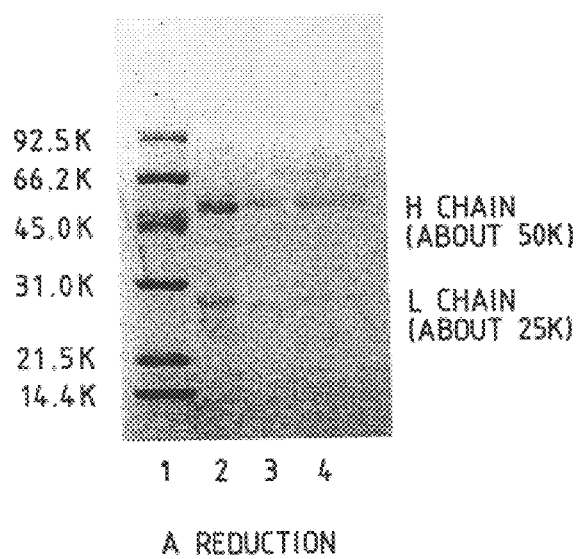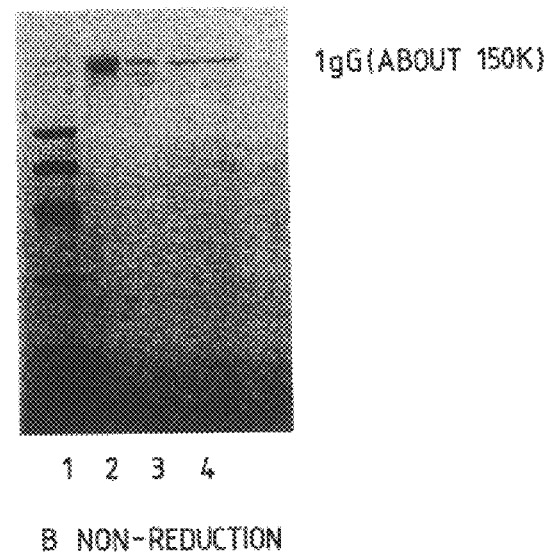
FIG. 31A / FIG. 31B

Melanoma
SK-MEL-28

Melanoma
G361

SEQUENCE LISTING

```
<160> NUMBER OF SEQ ID NOS: 19

<210> SEQ ID NO 1
<211> LENGTH: 812
<212> TYPE: DNA
<213> ORGANISM: Artificial Sequence
<220> FEATURE:
<223> OTHER INFORMATION: Description of Artificial Sequence:
      Rat Hybridoma
<220> FEATURE:
<221> NAME/KEY: TATA_signal
<222> LOCATION: (256)..(262)
<221> NAME/KEY: sig_peptide
<222> LOCATION: (300)..(440)
<221> NAME/KEY: CDS
<222> LOCATION: (300)..(344)
<221> NAME/KEY: CDS
<222> LOCATION: (429)..(806)
<221> NAME/KEY: mat_peptide
<222> LOCATION: (300)..(806)
<221> NAME/KEY: intron
<222> LOCATION: (346)..(428)

<400> SEQUENCE: 1
aaagtcagac aactttgtag agtaggttct atcaatccta ctgcaatcca acatcactga      60
```

```
ggacaaatgt ttatactgag gaacctggtc ttgtgtgata cgtactttct gtgggaagca    120
gatacgcact ctcatgtggc tcctgaattt cccatcacag aatgatacat cttgagtcct    180
aaaatttaag tacaccatca gtgtcagcac ctggtgagga aatgcaaatc tctcctggat    240
ccacccaacc ttgggttgaa aagccaaagc tgggcctggg tactcactgg tgtgcagcc    299 atg gac agg ctt act tcc tca ttc cta ctg ctg atg gtc cct gca t       345
Met Asp Arg Leu Thr Ser Ser Phe Leu Leu Leu Met Val Pro Ala
-19             -15                 -10                 -5 gtgagtacca aagcttccta agtgatgaac tgttctatcc tcacctgttc aaacctgacc    405
tcctcccctt tgatttctcc acag  at gtc ctg tct cag gtt act ctg aaa      455
                              Tyr Val Leu Ser Gln Val Thr Leu Lys
                                    1                       5 gaa tct ggc cct ggg ata ttg cag ccc tcc cag acc ctc agt ctg act     503
Glu Ser Gly Pro Gly Ile Leu Gln Pro Ser Gln Thr Leu Ser Leu Thr
            10                  15                  20 tgc tct ttc tct ggg ttt tca ctg agc act tat ggt atg tgt gtg ggc     551
Cys Ser Phe Ser Gly Phe Ser Leu Ser Thr Tyr Gly Met Cys Val Gly
                25                  30                  35 tgg att cgt cag tct tca ggg aag ggt ctg gag tgg ctg gca aac gtt     599
Trp Ile Arg Gln Ser Ser Gly Lys Gly Leu Glu Trp Leu Ala Asn Val
        40                  45                  50 tgg tgg agt gat gct aag tac tac aat cca tct ctg aaa aac cgg ctc     647
Trp Trp Ser Asp Ala Lys Tyr Tyr Asn Pro Ser Leu Lys Asn Arg Leu
    55                  60                  65 aca atc tcc aag gac acc tcc aac aac caa gca ttc ctc aag atc acc     695
Thr Ile Ser Lys Asp Thr Ser Asn Asn Gln Ala Phe Leu Lys Ile Thr
70                  75                  80                  85 aat atg gac act gca gat act gcc ata tac tac tgt gct ggg aga ggg    743
Asn Met Asp Thr Ala Asp Thr Ala Ile Tyr Tyr Cys Ala Gly Arg Gly
                90                  95                  100 gct acg gag ggt ata gtg agc ttt gat tac tgg ggc cac gga gtc atg    791
Ala Thr Glu Gly Ile Val Ser Phe Asp Tyr Trp Gly His Gly Val Met
            105                 110                 115 gtc aca gtc tcc tca ggtaag                                          812
Val Thr Val Ser Ser
        120

<210> SEQ ID NO 2
<211> LENGTH: 141
<212> TYPE: PRT
<213> ORGANISM: Artificial Sequence
<220> FEATURE:
<223> OTHER INFORMATION: Rat hybridoma

<400> SEQUENCE: 2

Met Asp Arg Leu Thr Ser Ser Phe Leu Leu Leu Met Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Ser Thr Tyr Gly Met Cys Val Gly Trp Ile Arg Gln Ser Ser Gly Lys
    50                  55                  60

Gly Leu Glu Trp Leu Ala Asn Val Trp Trp Ser Asp Ala Lys Tyr Tyr
65                  70                  75                  80

Asn Pro Ser Leu Lys Asn Arg Leu Thr Ile Ser Lys Asp Thr Ser Asn
                85                  90                  95
```

Asn Gln Ala Phe Leu Lys Ile Thr Asn Met Asp Thr Ala Asp Thr Ala
                100                 105                 110

Ile Tyr Tyr Cys Ala Gly Arg Gly Ala Thr Glu Gly Ile Val Ser Phe
        115                 120                 125

Asp Tyr Trp Gly His Gly Val Met Val Thr Val Ser Ser
    130                 135                 140

<210> SEQ ID NO 3
<211> LENGTH: 19
<212> TYPE: PRT
<213> ORGANISM: Artificial Sequence
<220> FEATURE:
<223> OTHER INFORMATION: Rat Hybridoma

<400> SEQUENCE: 3

Met Asp Arg Leu Thr Ser Ser Phe Leu Leu Leu Met Val Pro Ala Tyr
 1               5                  10                  15

Val Leu Ser

<210> SEQ ID NO 4
<211> LENGTH: 126
<212> TYPE: PRT
<213> ORGANISM: Artificial Sequence
<220> FEATURE:
<223> OTHER INFORMATION: Rat hybridoma

<400> SEQUENCE: 4

Tyr Val Leu Ser Gln Val Thr Leu Lys Glu Ser Gly Pro Gly Ile Leu
 1               5                  10                  15

Gln Pro Ser Gln Thr Leu Ser Leu Thr Cys Ser Phe Ser Gly Phe Ser
            20                  25                  30

Leu Ser Thr Tyr Gly Met Cys Val Gly Trp Ile Arg Gln Ser Ser Gly
        35                  40                  45

Lys Gly Leu Glu Trp Leu Ala Asn Val Trp Trp Ser Asp Ala Lys Tyr
 50                  55                  60

Tyr Asn Pro Ser Leu Lys Asn Arg Leu Thr Ile Ser Lys Asp Thr Ser
 65                  70                  75                  80

Asn Asn Gln Ala Phe Leu Lys Ile Thr Asn Met Asp Thr Ala Asp Thr
                85                  90                  95

Ala Ile Tyr Tyr Cys Ala Gly Arg Gly Ala Thr Glu Gly Ile Val Ser
            100                 105                 110

Phe Asp Tyr Trp Gly His Gly Val Met Val Thr Val Ser Ser
        115                 120                 125

<210> SEQ ID NO 5
<211> LENGTH: 46
<212> TYPE: DNA
<213> ORGANISM: Artificial Sequence
<220> FEATURE:
<223> OTHER INFORMATION: cDNA KM-641

<400> SEQUENCE: 5
agctgaattc gggcccgata tcaagcttgt cgactctaga ggtacc            46

<210> SEQ ID NO 6
<211> LENGTH: 29
<212> TYPE: DNA
<213> ORGANISM: Artificial Sequence
<220> FEATURE:
<223> OTHER INFORMATION: DNA KM-641

<400> SEQUENCE: 6

-continued

```
gatgaagaca gatatcgcag ccacagttc                                       29
```

```
<210> SEQ ID NO 7
<211> LENGTH: 403
<212> TYPE: DNA
<213> ORGANISM: Artificial Sequence
<220> FEATURE:
<223> OTHER INFORMATION: cDNA KM-641
<220> FEATURE:
<221> NAME/KEY: CDS
<222> LOCATION: (14)..(403)
<221> NAME/KEY: sig_peptide
<222> LOCATION: (14)..(43)

<400> SEQUENCE: 7
```

```
aattcggcac gag ctt gtc ctt gtt ttc aaa ggt gtt cag tgt gaa gtg       49
            Leu Val Leu Val Phe Lys Gly Val Gln Cys Glu Val
                1               5                   10 acg ctg gtg gag tct ggg gga gac ttt gtg aaa cct gga ggg tcc ctg       97
Thr Leu Val Glu Ser Gly Gly Asp Phe Val Lys Pro Gly Gly Ser Leu
        15                  20                  25 aaa gtc tcc tgt gca gcc tct gga ttc gct ttc agt cat tat gcc atg      145
Lys Val Ser Cys Ala Ala Ser Gly Phe Ala Phe Ser His Tyr Ala Met
    30                  35                  40 tct tgg gtt cgc cag act ccg gcg aag agg ctg gaa tgg gtc gca ggt      193
Ser Trp Val Arg Gln Thr Pro Ala Lys Arg Leu Glu Trp Val Ala Gly
45                  50                  55                  60 att agt agt ggt ggt agt ggc acc tac tat tca gac agt gta aag ggc      241
Ile Ser Ser Gly Gly Ser Gly Thr Tyr Tyr Ser Asp Ser Val Lys Gly
                65                  70                  75 cga ttc acc att tcc aga gac aat gcc aag aac acc ctg tac ctg caa      289
Arg Phe Thr Ile Ser Arg Asp Asn Ala Lys Asn Thr Leu Tyr Leu Gln
            80                  85                  90 atg cgc agt ctg agg tct gag gac tcg gcc atg tat ttc tgt aca aga      337
Met Arg Ser Leu Arg Ser Glu Asp Ser Ala Met Tyr Phe Cys Thr Arg
        95                  100                 105 gtt aaa ctg gga acc tac tac ttt gac tcc tgg ggc caa ggc acc act      385
Val Lys Leu Gly Thr Tyr Tyr Phe Asp Ser Trp Gly Gln Gly Thr Thr
    110                 115                 120 ctc act gtc tcc tca gct                                              403
Leu Thr Val Ser Ser Ala
125                 130
```

```
<210> SEQ ID NO 8
<211> LENGTH: 130
<212> TYPE: PRT
<213> ORGANISM: Artificial Sequence
<220> FEATURE:
<223> OTHER INFORMATION: cDNA KM-641

<400> SEQUENCE: 8
```

```
Leu Val Leu Val Phe Lys Gly Val Gln Cys Glu Val Thr Leu Val Glu
1               5                   10                  15

Ser Gly Gly Asp Phe Val Lys Pro Gly Gly Ser Leu Lys Val Ser Cys
            20                  25                  30

Ala Ala Ser Gly Phe Ala Phe Ser His Tyr Ala Met Ser Trp Val Arg
        35                  40                  45

Gln Thr Pro Ala Lys Arg Leu Glu Trp Val Ala Gly Ile Ser Ser Gly
    50                  55                  60

Gly Ser Gly Thr Tyr Tyr Ser Asp Ser Val Lys Gly Arg Phe Thr Ile
65                  70                  75                  80
```

```
Ser Arg Asp Asn Ala Lys Asn Thr Leu Tyr Leu Gln Met Arg Ser Leu
                85                  90                  95

Arg Ser Glu Asp Ser Ala Met Tyr Phe Cys Thr Arg Val Lys Leu Gly
            100                 105                 110

Thr Tyr Tyr Phe Asp Ser Trp Gly Gln Gly Thr Thr Leu Thr Val Ser
                115                 120                 125

Ser Ala
    130

<210> SEQ ID NO 9
<211> LENGTH: 408
<212> TYPE: DNA
<213> ORGANISM: Artificial Sequence
<220> FEATURE:
<223> OTHER INFORMATION: cDNA KM-641
<220> FEATURE:
<221> NAME/KEY: CDS
<222> LOCATION: (25)..(408)
<221> NAME/KEY: mat_peptide
<222> LOCATION: (85)..(408)
<221> NAME/KEY: sig_peptide
<222> LOCATION: (25)..(84)

<400> SEQUENCE: 9
aattcggcac gagtcagcct ggac atg atg tcc tct gct cag ttc ctt ggt        51
                          Met Met Ser Ser Ala Gln Phe Leu Gly
                              -20                 -15 ctc ctg ttg ctc tgt ttt caa ggt acc aga tgt gat atc cag atg aca       99
Leu Leu Leu Leu Cys Phe Gln Gly Thr Arg Cys Asp Ile Gln Met Thr
    -10                 -5              -1   1               5 cag act gca tcc tcc ctg cct gcc tct ctg gga gac aga gtc acc atc      147
Gln Thr Ala Ser Ser Leu Pro Ala Ser Leu Gly Asp Arg Val Thr Ile
            10                  15                  20 agt tgc agt gca agt cag gac att agt aat tat tta aac tgg tat caa      195
Ser Cys Ser Ala Ser Gln Asp Ile Ser Asn Tyr Leu Asn Trp Tyr Gln
                25                  30                  35 cag aaa cca gat gga act gtt aaa ctc ctg atc ttt tac tca tca aat      243
Gln Lys Pro Asp Gly Thr Val Lys Leu Leu Ile Phe Tyr Ser Ser Asn
        40                  45                  50 tta cac tcg gga gtc cca tca agg ttc agt ggc ggt ggg tcc ggg aca      291
Leu His Ser Gly Val Pro Ser Arg Phe Ser Gly Gly Gly Ser Gly Thr
    55                  60                  65 gat tat tct ctc acc atc agc aac ctg gag cct gaa gat att gcc act      339
Asp Tyr Ser Leu Thr Ile Ser Asn Leu Glu Pro Glu Asp Ile Ala Thr
70                  75                  80                  85 tac ttt tgt cat cag tat agt aag ctt ccg tgg acg ttc ggt gga ggc      387
Tyr Phe Cys His Gln Tyr Ser Lys Leu Pro Trp Thr Phe Gly Gly Gly
                90                  95                 100 acc aag ctg gaa atc aaa cgg                                          408
Thr Lys Leu Glu Ile Lys Arg
            105

<210> SEQ ID NO 10
<211> LENGTH: 128
<212> TYPE: PRT
<213> ORGANISM: Artificial Sequence
<220> FEATURE:
<223> OTHER INFORMATION: cDNA KM-641

<400> SEQUENCE: 10

Met Met Ser Ser Ala Gln Phe Leu Gly Leu Leu Leu Leu Cys Phe Gln
-20                 -15                 -10                 -5

Gly Thr Arg Cys Asp Ile Gln Met Thr Gln Thr Ala Ser Ser Leu Pro
```

```
              -1   1            5                   10
        Ala Ser Leu Gly Asp Arg Val Thr Ile Ser Cys Ser Ala Ser Gln Asp
                     15                  20                  25

Ile Ser Asn Tyr Leu Asn Trp Tyr Gln Gln Lys Pro Asp Gly Thr Val
                     30                  35                  40

Lys Leu Leu Ile Phe Tyr Ser Ser Asn Leu His Ser Gly Val Pro Ser
             45                  50                  55                  60

Arg Phe Ser Gly Gly Gly Ser Gly Thr Asp Tyr Ser Leu Thr Ile Ser
                         65                  70                  75

Asn Leu Glu Pro Glu Asp Ile Ala Thr Tyr Phe Cys His Gln Tyr Ser
                     80                  85                  90

Lys Leu Pro Trp Thr Phe Gly Gly Gly Thr Lys Leu Glu Ile Lys Arg
                     95                 100                 105

<210> SEQ ID NO 11
<211> LENGTH: 35
<212> TYPE: DNA
<213> ORGANISM: Artificial Sequence
<220> FEATURE:
<221> NAME/KEY: CDS
<222> LOCATION: (9)..(35)
<223> OTHER INFORMATION: cDNA KM-641

<400> SEQUENCE: 11 aattcacc atg gag ttt ggg ctc agc tgg ctt ttt                        35
        Met Glu Phe Gly Leu Ser Trp Leu Phe
         1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: cDNA KM-641

<400> SEQUENCE: 12

Met Glu Phe Gly Leu Ser Trp Leu Phe
 1               5

<210> SEQ ID NO 13
<211> LENGTH: 42
<212> TYPE: DNA
<213> ORGANISM: Artificial Sequence
<220> FEATURE:
<223> OTHER INFORMATION: H chain variable
      region
<220> FEATURE:
<221> NAME/KEY: CDS
<222> LOCATION: (1)..(42)

<400> SEQUENCE: 13 caa ggt acc acg tta act gtc tcc tca gcc tcc acc aag ggc            42
Gln Gly Thr Thr Leu Thr Val Ser Ser Ala Ser Thr Lys Gly
 1               5                  10

<210> SEQ ID NO 14
<211> LENGTH: 14
<212> TYPE: PRT
<213> ORGANISM: Artificial Sequence
<220> FEATURE:
<223> OTHER INFORMATION: H chain variable
      region

<400> SEQUENCE: 14

Gln Gly Thr Thr Leu Thr Val Ser Ser Ala Ser Thr Lys Gly
```

<210> SEQ ID NO 15
<211> LENGTH: 61
<212> TYPE: DNA
<213> ORGANISM: Artificial Sequence
<220> FEATURE:
<221> NAME/KEY: CDS
<222> LOCATION: (3)..(59)
<223> OTHER INFORMATION: cDNA KM-641

<400> SEQUENCE: 15

```
ag ctt cca tgg acg ttc ggt gga ggc acc aag ctg gaa atc aaa cga      47
   Leu Pro Trp Thr Phe Gly Gly Gly Thr Lys Leu Glu Ile Lys Arg
     1               5                  10                  15 act gtg gct gca cc                                                   61
Thr Val Ala Ala
```

<210> SEQ ID NO 16
<211> LENGTH: 19
<212> TYPE: PRT
<213> ORGANISM: Artificial Sequence
<220> FEATURE:
<223> OTHER INFORMATION: cDNA KM-641

<400> SEQUENCE: 16

Leu Pro Trp Thr Phe Gly Gly Gly Thr Lys Leu Glu Ile Lys Arg Thr
 1               5                  10                  15

Val Ala Ala

<210> SEQ ID NO 17
<211> LENGTH: 27
<212> TYPE: DNA
<213> ORGANISM: Artificial Sequence
<220> FEATURE:
<223> OTHER INFORMATION: pchCKA7 insert

<400> SEQUENCE: 17
aaacgaactg tggctgcacc atctgtc                                        27

<210> SEQ ID NO 18
<211> LENGTH: 130
<212> TYPE: PRT
<213> ORGANISM: Artificial Sequence
<220> FEATURE:
<223> OTHER INFORMATION: cDNA KM-641

<400> SEQUENCE: 18

Leu Val Leu Val Phe Lys Gly Val Gln Cys Glu Val Thr Leu Val Glu
 1               5                  10                  15

Ser Gly Gly Asp Phe Val Lys Pro Gly Gly Ser Leu Lys Val Ser Cys
            20                  25                  30

Ala Ala Ser Gly Phe Ala Phe Ser His Tyr Ala Met Ser Trp Val Arg
        35                  40                  45

Gln Thr Pro Ala Lys Arg Leu Glu Trp Val Ala Tyr Ile Ser Ser Gly
    50                  55                  60

Gly Ser Gly Thr Tyr Tyr Ser Asp Ser Val Lys Gly Arg Phe Thr Ile
65                  70                  75                  80

Ser Arg Asp Asn Ala Lys Asn Thr Leu Tyr Leu Gln Met Arg Ser Leu
                85                  90                  95

Arg Ser Glu Asp Ser Ala Met Tyr Phe Cys Thr Arg Val Lys Leu Gly
            100                 105                 110

```
Thr Tyr Tyr Phe Asp Ser Trp Gly Gln Gly Thr Thr Leu Thr Val Ser
        115                 120                 125

Ser Ala
    130

<210> SEQ ID NO 19
<211> LENGTH: 128
<212> TYPE: PRT
<213> ORGANISM: Artificial Sequence
<220> FEATURE:
<223> OTHER INFORMATION: light chain
      variable region

<400> SEQUENCE: 19

Met Met Ser Ser Ala Gln Phe Leu Gly Leu Leu Leu Cys Phe Gln
  1           5                  10                  15

Gly Thr Arg Cys Asp Ile Gln Met Thr Gln Thr Ala Ser Ser Leu Pro
            20                  25                  30

Ala Ser Leu Gly Asp Arg Val Thr Ile Ser Cys Ser Ala Ser Gln Asp
            35                  40                  45

Ile Ser Asn Tyr Leu Asn Trp Tyr Gln Gln Lys Pro Asp Gly Thr Val
 50                  55                  60

Lys Leu Leu Ile Phe Tyr Ser Ser Asn Leu His Ser Gly Val Pro Ser
 65                  70                  75                  80

Arg Phe Ser Gly Gly Gly Ser Gly Thr Asp Tyr Ser Leu Thr Ile Ser
                85                  90                  95

Asn Leu Glu Pro Glu Asp Ile Ala Thr Tyr Phe Cys His Gln Tyr Ser
            100                 105                 110

Lys Leu Pro Trp Thr Phe Gly Gly Thr Lys Leu Glu Ile Lys Arg
            115                 120                 125
```

POLYPEPTIDE COMPOSING HUMAN CHIMERIC ANTIBODY

This is a divisional of application Ser. No. 09/225,322, filed Jan. 5, 1999, now pending, which in turn is divisional of application Ser. No. 08/454,680, filed May 31, 1995, now U.S. Pat. No. 5,866,692; which is a divisional of Ser. No. 08/408,133, filed Mar. 21, 1995, now U.S. Pat. No. 5,750,078; which is a continuation of Ser. No. 08/292,178, filed Aug. 17, 1994, abandoned; which is a continuation of Ser. No. 07/947,674, filed Sep. 17, 1992, abandoned, the entire content of which is hereby incorporated by reference in this application.

FIELD OF THE INVENTION

This invention relates to a process for the production of humanized chimera antibody. In contrast to mouse monoclonal antibody, humanized chimera antibody does not cause formation of anti-mouse immunoglobulin antibody in the body of a patient. Thus, side effects are reduced or eliminated and half life in blood increases when the chimera antibody is used. Therapeutic effects which are superior to those obtained in the case of using mouse monoclonal antibody can be obtained in the treatment of human cancers and the like.

BACKGROUND OF THE INVENTION

It is known that, when mouse antibodies are administered to humans, they are recognized as foreign substances and cause formation of anti-mouse immunoglobulin antibodies in the human body, and the thus formed antibodies react with the administered mouse antibodies. As a result, side effects occur (J. Clin. Oncol., 2, 881 (1984); Blood, 65, 1349–1363 (1985); J. Natl. Cancer Inst., 80, 932 (1988); Proc. Natl. Acad. Sci. U.S.A., 82, 1242 (1985)), the antibodies are cleared away quickly (J. Nucl. Med., 26, 1011 (1985); Blood, 65, 1349–1363 (1985); J. Natl. Cancer Inst., 80, 937 (1988)) and effects of the antibodies are reduced (J. Immunol., 135, 1530 (1985); Cancer Res., 46, 6489 (1986)). When mouse monoclonal antibody is converted into humanized chimera antibody, human anti-mouse immunoglobulin antibody form in minimal amounts if at all, and the half life of the chimera antibody in human blood is six times as long as that of mouse monoclonal antibody (Proc. Natl. Acad. Sci. U.S.A., 86, 4220 (1989)). In addition, it is probable that the Fc region of mouse antibody does not fully activate human complement and human effector cells, in comparison with the Fc region of human antibody. For example, the antitumor activity of mouse monoclonal antibody to ganglioside $GD_2$, which is effected via human effector cells, is improved when the monoclonal antibody is converted into chimera antibody that has the human antibody Fc region (J. Immunol., 144, 1382–1386 (1990)).

Ganglioside is one of the animal cell membrane-constituting glycolipids and is composed of a sugar chain as a hydrophilic side chain, sphingosine as a hydrophobic side chain and fatty acids. It is known that expression of ganglioside varies depending on the type of cells, organs and animal species. In addition, it has been revealed that quantity and quality of the expressed ganglioside change during the canceration process of cells (Cancer Res., 45, 2405 (1985)). For example, it has been reported that gangliosides $GD_2$, $GD_3$, $GM_2$ and the like which hardly exist in normal cells were found in the cells of neuroblastoma, lung small cell carcinoma and melanoma belonging to neuroectodermal-origin tumor which is said to be highly malignant (J. Exp. Med., 155, 1133 (1982); J. Biol. Chem., 257, 12752 (1982); Cancer Res., 47, 225 (1987); ibid., 47, 1098 (1987); ibid., 45, 2642 (1985); Proc. Natl. Acad. Sci. U.S.A., 80, 5392 (1983)).

Ganglioside $GD_3$ has been found most frequently in melanoma cells among the neuroectodermal-origin tumors, and anti-ganglioside $GD_3$ monoclonal antibodies (to be referred to as "anti-$GD_3$ monoclonal antibody" hereinafter) belonging to the mouse IgM class and IgG class have been reported (Int. J. Cancer, 29, 269 (1982); J. Biol. Chem., 257, 12752 (1982); Cancer Res., 47, 225 (1987); Acta Neuropathol., 79, 317 (1989); Proc. Natl. Acad. Sci. U.S.A., 77, 6114 (1980); J. Exp. Med., 155, 1133 (1982); Proc. Natl. Acad. Sci. U.S.A., 81, 5767 (1984)).

KM-641 (FERM BP-3116) disclosed in EP-A-0 493 686 is an anti-$GD_3$ monoclonal antibody belonging to the mouse IgG3 class, which reacts not only with ganglioside $GD_3$ but also with ganglioside 3',8'-LD1 and is possessed of a broad range of antitumor spectrum. In addition, KM-641 has stronger binding activities to antigens than anti-$GD_3$ monoclonal antibody R24 which has been disclosed in J. Exp. Med., 155, 1133 (1982) and it shows strong antitumor activities.

The mouse monoclonal antibody R24 to the ganglioside $GD_3$ was once used for the treatment of melanoma, but the administered mouse monoclonal antibody R24 did not fully exert its effect due to the formation of anti-mouse immunoglobulin antibody in the patient's body (Eur. J. Cancer Clin. Oncol., 24, suppl 2, s 65 (1988)).

Consequently, the use of chimera antibody for anti-$GD_3$ monoclonal antibody would be advantageous in that anti-mouse immunoglobulin antibody does not form in the body, side effects are reduced or eliminated, its half life in blood is prolonged and its antitumor effector effect increases, and thus therapeutic effects of the chimera antibody which are superior to those of mouse monoclonal antibody can be obtained in the treatment of human cancers and the like.

Several processes for the production of humanized chimera antibodies are known. Humanized chimera antibody, in which constant regions of the heavy chain (to be referred to as "H chain" hereinafter) and the light chain (to be referred to as "L chain" hereinafter) of mouse monoclonal antibody are converted into human constant regions, is produced in animal cells making use of recombinant DNA techniques. Examples of such processes include a process in which humanized chimera antibody is produced using chromosomal DNA as a gene which encodes mouse H chain variable region (to be referred to as "$V_H$" hereinafter) and L chain variable region (to be referred to as "$V_L$" hereinafter) (Morrison et al., Proc. Natl. Acad. Sci. U.S.A., 81, 6851 (1984); Neuberger et al., Nature, 314, 268 (1985); Nishimura et al., Cancer Res., 47, 999 (1987); Dorai et al., J. Immunol., 139, 4232 (1987); Kameyama et al., FEBS letter, 244, 301 (1989)) and another process in which humanized chimera antibody is produced using cDNA (Gillies et al., J. Immunol. Methods, 125, 191 (1989); Liu et al., published International Application in Japan No. 2-501886). Cloning and base sequence determination of hybridoma cell chromosomal DNA which encodes mouse $V_H$ and $V_L$ require much time and labor in comparison with those of cDNA that encodes mouse $V_H$ and $V_L$. Consequently, the process in which cDNA is used for the production of humanized chimera antibody is more desirable than the chromosomal DNA process.

Gillies et al. have succeeded in expressing humanized chimera antibody in animal cells, making use of an expression vector for animal cells having inserted therein a humanized chimera H chain gene obtained by linking mouse $V_H$-encoding cDNA with human $C_H$-encoding chromosomal DNA, and a humanized chimera L chain gene obtained by linking mouse $V_L$-encoding cDNA with human $C_L$-encoding chromosomal DNA (J. Immunol. Methods, 125, 191 (1989)). However, when an attempt was made to prepare chimera antibodies from several types of antibodies, a problem was found that there were certain chimera antibodies whose L chains could not be expressed without converting leader sequences. In addition, humanized chimera antibody can be produced more simply when cDNA which encodes human $C_H$ and $C_L$ is used instead of the human $C_H$- and $C_L$-encoding chromosomal DNA.

In published International Application in Japan No. 2-501886, Liu et al. discloses a process for the expression of humanized chimera antibody in animal cells, which comprises using an expression vector for animal cells having inserted therein a chimera H chain cDNA obtained by linking mouse $V_H$-encoding cDNA with human $C_H$-encoding cDNA and a chimera L chain cDNA obtained by linking mouse VsL-encoding cDNA with human $C_L$-encoding cDNA. According to this process, however, it is necessary to alter the Ja portion of the $V_H$-encoding cDNA and the $J_L$ portion of the $V_L$-encoding cDNA by means of mutation, because the cDNA which encodes mouse $V_H$ or $V_L$ is linked with the human $C_H$- or $C_L$-encoding cDNA at the J region in the mouse variable region. In addition, with regard to the chimera L chain prepared using mouse Jk5, leucine which is one of the amino acids of the framework 4 is changed to isoleucine when made into humanized chimera antibody. Although amino acid sequence of complementarity-determining region (to be referred to as "CDR" hereinafter) is especially important for antigen-antibody binding, the amino acid sequence of the framework is also an important factor. For example, Riechmann et al. have prepared CDR graft antibody by grafting a rat antibody CDR into a human antibody framework and reported that binding activity of the antibody was reduced by the framework conversion and the antibody activity increased when amino acid sequence of the framework was partially changed (Nature, 332, 323 (1988)). Consequently, there is a possibility that the binding activity of humanized chimera antibody is undesirably reduced when the antibody is produced by the mouse Jk5-aided process disclosed by Liu et al.

In view of the above, when any mouse antibody is converted into humanized chimera antibody, it has been desired to simply and easily produce humanized chimera antibody in which amino acids of the mouse antibody variable region remain completely unchanged.

OBJECTS OF THE INVENTION

An object of the present invention is to provide a process for the production of humanized chimera antibody by which the chimera antibody is produced easily without changing any of the amino acids of its mouse antibody variable region. Another object of the present invention is to provide a humanized chimera antibody to ganglioside $GD_3$ and a process for the production of such antibody.

SUMMARY OF THE INVENTION

The present invention relates to a process for producing humanized chimera antibody which comprises the steps of:
(1) constructing a cassette vector by inserting a cDNA coding for human antibody $C_H$ into an expression vector for animal cell use and establishing a cloning site in the upstream region $C_H$ of said cassette vector for inserting a cDNA which encodes nonhuman animal $V_H$;
(2) digesting a cDNA coding for nonhuman animal antibody $V_H$ with restriction enzymes;
(3) inserting said cDNA coding for nonhuman animal antibody $V_H$ into the cassette vector, using a synthetic DNA which comprises a base sequence corresponding to the 5'-end side of said human antibody $C_H$ and a base sequence corresponding to the 3'-end side of said nonhuman animal antibody $V_H$ and is possessed of restriction enzyme recognition sites on both of its ends, thereby constructing a humanized chimera antibody H chain expression vector in which said cDNA coding for human antibody $C_H$ and said cDNA coding for nonhuman animal antibody $V_H$ are linked together through said synthetic DNA;
(4) constructing a cassette vector by inserting a cDNA coding for human antibody $C_L$ into an expression vector for animal cell use and establishing a cloning site in the upstream region of the $C_L$ of said cassette vector for inserting a cDNA which encodes nonhuman animal antibody $V_L$;
(5) digesting a cDNA coding for nonhuman animal antibody $V_L$ with restriction enzymes;
(6) inserting said cDNA coding for nonhuman animal antibody $V_L$ into the cassette vector, using a synthetic DNA which comprises a base sequence corresponding to the 5'-end side of said human antibody $C_L$ and a base sequence corresponding to the 3'-end side of said nonhuman animal antibody $V_L$ and is possessed of restriction enzyme recognition sites on both of its ends, thereby constructing a humanized chimera antibody L chain expression vector in watch said cDNA coding for human antibody $C_L$ and said cDNA coding for nonhuman animal antibody $V_L$ are linked together through said synthetic DNA;
(7) introducing these expression vectors into host cells to obtain a transformant; and
(8) culturing said transformant in an appropriate culture medium, thereby allowing the transformant to produce and accumulate a humanized chimera antibody, and collecting said humanized chimera antibody from the resulting culture broth.

The cassette vector to be used in the present invention is a vector which is obtained by inserting a cDNA that encodes a constant region of human antibody into an expression vector for animal cell use, in which a cloning site is located in the upstream region of the constant region for inserting a cDNA that encodes a variable region of nonhuman animal antibody. An expression vector for humanized chimera antibody can be constructed easily by inserting a variable region of nonhuman animal antibody into the cloning site of the cassette vector, using a synthetic DNA which comprises a base sequence corresponding to the 5'-end side of a constant region of human antibody and a base sequence corresponding to the 3'-end side of a variable region of nonhuman animal antibody and is possessed of restriction enzyme recognition sites on its both ends.

The present invention also relates to a humanized chimera antibody obtainable by the above-described process, a pharmaceutical composition comprising the humanized chimera antibody and a pharmaceutically acceptable carrier, and a method of treating cancer which comprises administering to a patient a pharmaceutically acceptable amount of said humanized chimera antibody.

BRIEF DESCRIPTION OF THE DRAWINGS

FIG. 5 shows a construction scheme for plasmid pEP-KMB1.

FIG. 7 shows a construction scheme for plasmid pAGE109.

FIG. 11 shows a construction scheme for plasmid pSE1D2.

FIG. 13 shows a construction scheme for plasmid pIG1SE1d3.

FIG. 15 shows a construction scheme for plasmid pPMOL2.

FIG. 16 shows a construction scheme for plasmid pPMOL3.

FIG. 18 shows a construction scheme for plasmid pch-CKB1 (also SEQ ID NO:9).

FIG. 19 shows a construction scheme for plasmid pck-CKC1.

FIG. 31 shows a pattern of SDS-PAGE (4 to 15% gradient gel) of purified anti-GD$_3$ chimera antibody KM-871 (about 5 μg/lane) carried out under reductive condition (A) or non-reductive condition (B), where the lanes starting from the left respectively indicate electrophoretic patterns of molecular weight markers, human IgG standard, mouse anti-GD$_3$ antibody KM-641 and anti-GD$_3$ chimera antibody KM-871.

DETAILED DESCRIPTION OF THE INVENTION

1. Construction of Cassette Vector

Figure 1:
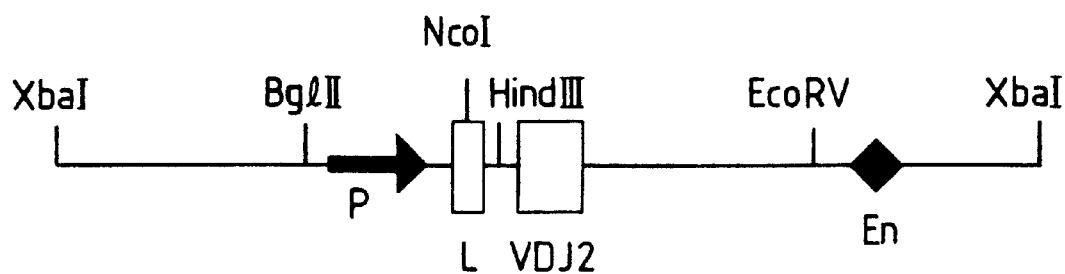
FIG. 1 shows a restriction enzyme cleavage map of a 9.3 kb XbaI fragment of KM50 cell chromosomal DNA.

The cassette vector to be used in the present invention is constructed by inserting a cDNA which encodes a human antibody constant region into an expression vector for animal cell use. Essential components in the expression vector for animal cell use include promoter, enhancer, polyA signal, splicing signal, drug resistance gene as a selection marker (e.g., ampicillin resistance gene, etc.) and the like. Any expression vector for animal cell use may be used for this purpose, as long as it can contain and express the cDNA molecule which encodes a human antibody constant reason. For example, pAGE107 (Cytotechnology, 3, 133 (1990)) is useful as such an expression vector. Examples of the promoter and enhancer for use in the expression vector for animal cell use include: SV40 early promoter and enhancer (J. Biochem., 101, 1307 (1987)); LTR promoter and enhancer of Moloney mouse leukemia virus (Biochem. Biophys. Res. Comun., 149, 960 (1987)); and immunoglobulin H chain promoter (Cell, 41, 479 (1985)) and enhancer (Cell, 33, 717 (1983)). The immunoglobulin H chain promoter and enhancer can be prepared using appropriate antibody-producing hybridoma cells, such as rat hybridoma KM50 cells which produce anti-human serum albumin antibody as disclosed in JP-A-60-258128 (the term "JP-A" as used herein means an "unexamined published Japanese patent application"). The following describes processes for the preparation of the immunoglobulin H chain promoter and enhancer making use of KH50 cells.

Each chromosomal DNA is obtained from cultured KM50 cells, and P3X63Ag8U.1 (to be referred to as "P3U1" hereinafter) cells (ATCC CRL1597) which are to be fused with KM50 and rat kidney cells in accordance with the procedure disclosed in Molecular Cloning (2nd. ed., Cold Spring Harbor Laboratory Press, 1989, p9.14). Next, a DNA fragment containing immunoglobulin promoter and enhancer and a gene of the variable region of activated immunoglobulin H chain, in which DNA rearrangement has been induced, is isolated from the chromosomal DNA extracted from KM50 cells, in accordance with the procedure disclosed in FEBS letter 244, 301 (1989). The immunoglobulin promoter and enhancer are cut out from the thus isolated DNA fragment and inserted into the aforementioned expression vector for animal cell use. Plasmid pIg1SE1d4 is an illustrative example of the animal cell expression vector which contains the immunoglobulin H chain promoter and enhancer.

Next, a cloning site is established in the upstream region of a human constant region of a cassette vector, for inserting a cDNA which encodes a variable region of nonhuman animal antibody. Into the thus established cloning site is inserted a cDNA which encodes a variable region of nonhuman animal antibody, using a synthetic DNA which comprises a base sequence corresponding to the 5'-end side of a constant region of human antibody and a base sequence corresponding to the 3'-end side of a variable region of nonhuman animal antibody and is possessed of restriction enzyme recognition sites on both of its ends. In this way, a humanized chimera antibody expression vector is constructed in which the cDNA coding for human antibody constant region and the cDNA coding for the variable region of nonhuman animal antibody are linked together through the synthetic DNA. The synthetic DNA to be used may be prepared using a DNA synthesizer, based on the base sequence which corresponds to the 5'-end side of a constant region of human antibody and the base sequence that corresponds to the 3'-end side of a variable region of nonhuman animal antibody. Illustrative examples of cloning site-containing cassette vectors include a cassette vector pChiIgHB2 which is used for the construction of an expression vector for the expression of humanized chimera antibody H chain and a cassette vector pChiIgLA2 which is used for the construction of an expression vector for the expression of humanized chimera antibody L chain.

A cassette vector for use in the construction of an expression vector for the expression of humanized chimera antibody H chain is constructed, for example, by cutting out a human $C_H$-encoding cDNA-containing fragment, from an ApaI site in the vicinity of the 5'-end of the cDNA to its 3'-end, and inserting the fragment into an appropriate expression vector for animal cell use such as plasmid pIg1SE1d4 or the like. Then, a cloning site is established in the thus constructed cassette vector for inserting a cDNA which encodes a $V_H$ of nonhuman animal antibody. Into the thus established cloning site is then inserted a cDNA fragment encoding a nonhuman animal antibody $V_H$, which is obtained by digesting a $V_H$-encoding cDNA with an appropriate restriction enzyme, using a synthetic DNA molecule which comprises a base sequence corresponding to the 5'-end side (5'-end to ApaI site) of a human antibody $C_H$ and a base sequence corresponding to the 3'-end side of a nonhuman animal antibody $V_H$ and is possessed of restriction enzyme recognition sites on both of its ends. In this way, an expression vector for use in the expression of humanized chimera antibody H chain is easily obtained without altering amino acid sequence of the expressed $V_H$.

A cassette vector for constructing of an expression vector for the expression for humanized chimera antibody L chain may be constructed for example by introducing an EcoRV site into the vicinity of 5'-end side of a human $C_L$-encoding cDNA by means of mutation, cutting out a fragment from the resulting human cDNA from the EcoRV site to the 3'-end and inserting the fragment into an appropriate expression vector such as plasmid pIg1SE1d4 or the like. Then, a cloning site is established in the thus constructed cassette vector for inserting a cDNA which encodes a nonhuman animal antibody $V_L$. Into the thus established cloning site is then inserted a cDNA fragment encoding a nonhuman animal antibody $V_L$, which is obtained by digesting a $V_L$-encoding cDNA with an appropriate restriction enzyme, using a synthetic DNA which comprises a base sequence corresponding to the 5'-end side (5'-end to EcoRV site) of a human antibody $C_L$ and a base sequence corresponding to the 3'-end side of a nonhuman animal antibody $V_L$ and is possessed of restriction enzyme recognition sites on both of its ends. In this way, an expression vector for use in the expression of humanized chimera antibody L chain is easily obtained without altering amino acid sequence of the expressed $V_L$.

Examples of the cDNAs which encode the human $C_H$ and human $C_L$ described above are disclosed, for instance, in Cell 22, 197 (1982). Such cDNAs can e prepared from human antibody-producing myeloma cells, humanized monoclonal antibody-producing hybridoma cells, humanized chimera antibody-producing cells (SP2-PC chimera; FEBS Letters, 244, 301 (1989)) and the like, in accordance with known procedures disclosed for instance in Proc. Natl. Acad. Sci. U.S.A. 82, 7025 (1985) and ibid., 79 7025 (1985). That is, cDNA is synthesized using mRNA extracted from the above-described cells, in accordance with the procedure disclosed in Molecular Cloning 2nd. ed.; 1989, p8.1. A library is prepared from the thus synthesized cDNA using a phage vector or a plasmid vector, in accordance with the procedure disclosed in Molecular Cloning 2nd. ed.; 1989, p8.1, 1.53. Next, a recombinant phage or a recombinant plasmid which contains human $C_H$-encoding cDNA or human $C_L$-encoding cDNA is obtained from the thus prepared library using a human antibody constant region or a human antibody variable region as a probe, in accordance with the procedure disclosed in Molecular Cloning 2nd. ed.; 1989, p8.1, 1.53. Base sequences of the human $C_H$-encoding cDNA and the human $C_L$-encoding cDNA are determined in accordance with the procedure disclosed in Molecular Cloning, 2nd. ed.; 1989, p13.1. Introduction of an appropriate restriction enzyme recognition site into the human $C_L$-encoding cDNA, for example insertion of an EcoRV recognition site into a region in the vicinity of the 5'-end of the cDNA, may be effected in accordance with the procedure disclosed in Molecular Cloning, 2nd. ed.; 1989, p15.1.

2. Production of Humanized Chimera Antibody

Firstly, cDNAs which encode $V_H$ and $V_L$ of nonhuman animal antibody, such as mouse anti-$GD_3$ monoclonal antibody, are prepared in the following manner.

That is, cDNA is synthesized using mRNA extracted from appropriate hybridoma cells which produce mouse anti-$GD_3$ monoclonal antibody, such as mouse anti-$GD_3$ monoclonal antibody KM-641 (FERM BP-3116). A library is prepared from the thus synthesized cDNA using a phage vector or a plasmid vector. Next, a recombinant phage or a recombinant plasmid which contains $V_H$-encoding cDNA or $V_L$-encoding cDNA is obtained from the thus prepared library using a constant region or a variable region of nonhuman antibody, such as mouse antibody, as a probe. Base sequences of the $V_H$-encoding cDNA and the $V_L$-encoding cDNA are determined in accordance with the aforementioned procedure.

A fragment of the $V_H$-encoding cDNA, ranging from the 5'-end to an appropriate restriction enzyme site near the 3'-end (to be referred to as "site A" hereinafter), is cut out and inserted into the cloning site of the aforementioned cassette vector, using a synthetic DNA which comprises a base sequence corresponding to the 5'-end side of a human antibody $C_H$ and a base sequence corresponding to the 3'-end side (from 3'-end to site A) of a nonhuman animal antibody $V_H$ and is possessed of restriction enzyme recognition sites on both of its ends. In this way, an expression vector for use in the expression of humanized chimera antibody H chain is constructed by linking the human antibody $C_H$-encoding cDNA with the nonhuman antibody $V_H$-encoding cDNA through the synthetic DNA. In the same way, a fragment of the $V_L$-encoding cDNA, ranging from the 5'-end to an appropriate restriction enzyme site near the 3'-end (to be referred to as "site B" hereinafter), is cut out and inserted into the cloning site of the aforementioned cassette vector, using a synthetic DNA molecule which comprises a base sequence corresponding to the 5'-end side of a human antibody $C_L$ and a base sequence corresponding to the 3'-end side (from 3'-end to site B) of a nonhuman animal antibody $V_L$ and is possessed of restriction enzyme recognition sites on both of its ends. In this way, an expression vector for use in the expression of humanized chimera antibody L chain is constructed by linking the human antibody $C_L$-encoding cDNA with the nonhuman antibody $V_L$-encoding cDNA through the synthetic DNA.

A transformant which is capable of producing humanized chimera antibody is obtained by transforming appropriate host cells with the thus prepared expression vectors for use in the expression of the H chain and L chain of humanized chimera antibody.

Any type of cells may be used as host cells for use in the introduction of the humanized chimera antibody expression vectors, as long as these cells are capable of expressing the humanized chimera antibody. Illustrative examples of such host cells include mouse SP2/0-Ag14 cells (ATCC CRL1581; to be referred to as "SP2/0 cells" hereinafter), mouse P3X63-Ag8.653 (ATCC CRL1580) and CHO cells which are deficient in dihydrofolate reductase gene (to be referred to as "dhfr" hereinafter) (Urlaub et al., Proc. Natl. Acad. Sci. U.S.A., 77, 4216 (1980)).

Introduction of the expression vectors for use in the expression of the H chain and L chain of humanized chimera antibody into host cells may be effected for example by the electroporation technique disclosed in JP-A-2-257891. A transformant capable of producing the humanized chimera antibody may be selected using RPMI1640 medium supplemented with G418 and fetal calf serum, in accordance with the procedure disclosed in JP-A-2-257891. A transformant, KM-871, which produces humanized chimera antibody that reacts with ganglioside $GD_3$ is an illustrative example of the transformant capable of producing humanized chimera antibody. KM-871 has been deposited on Aug.13, 1991, with Fermentation Research Institute, Agency of Industrial Science and Technology of 1–3, Higashi 1-chome, Tsukuba-shi, Ibaraki, Japan under the Budapest Treaty, and has been assigned the accession number FERM BP-3512.

For the cultivation of the thus-obtained transformants, any medium can be used as long as the desired antibody can be produced and accumulated in the medium. An example of such medium is RPMI1640 medium supplemented with G418 and fetal calf serum. The transformants may be inoculated into 200 $\mu$l to 100 ml of the above-mentioned medium to give a cell concentration of $1\times10^5$ to $1\times10^7$ cells/ml and cultivated at 37° C. in a 5% $CO_2$ incubator for 1 to 7 days. The desired chimera antibody is produced and accumulated in the culture medium.

Activity of the humanized chimera antibody in the culture broth is measured by enzyme-linked immunosorbent assay (ELISA method; E. Harlow et al., Manual of Antibody Experiments, Cold Spring Harbor Laboratory Press, 1988). Productivity of the humanized chimera antibody in the transformant can be improved making use of a dhfr amplification system in accordance with the procedure disclosed in JP-A-2-257891.

The humanized chimera antibody thus produced can be purified from supernatant fluid of the aforementioned cultured mixture making use of a protein A column (E. Harlow et al., Manual of Antibody Experiments, Cold Spring Harbor Laboratory Press, 1988). Illustrative examples of humanized chimera antibodies obtained in this way include those which react with ganglioside $GD_3$, such as humanized chimera antibody KM-871 and the like.

Reactivity of humanized chimera antibody is measured by ELISA method. The molecular weight of the H chain, the L chain or the entire molecule of purified humanized chimera antibody is measured by means of polyacrylamide gel electrophoresis (SDS-PAGE), Western blotting method (E. Harlow et al., Manual of Antibody Experiments, Cold Spring Harbor Laboratory Press, 1988) or the like.

Binding activity, or avidity, of the humanized chimera antibody to ganglioside $GD_3$ to a cultured cancer cell line is measured by means of the fluorescent antibody technique, the ELISA method or the like. Complement-dependent cytotoxicity (CDC activity) and antibody-dependent cell-mediated cytotoxicity (ADCC activity) of humanized chimera antibody to a cultured cancer cell line are measured in accordance with the procedures disclosed in Menekigaku Jikken Nyumon, (Manual of Immunological Experiments) Matsuhashi et al., Gakkai Shuppan Center, Japan, 1981).

The humanized chimera antibodies according to the present invention can be used alone as an anticancer agent. They may be formulated into an anticancer composition together with at least one pharmaceutically acceptable carrier. For instance, the humanized chimera antibodies are dissolved in physiological saline, an aqueous solution of glucose, lactose or mannitol and the like. The powder of the humanized chimera antibodies for injection can be prepared by lyophilizing the humanized chimera antibodies in accordance with the conventional method and mixing the lyophilized products with sodium chloride. The anticancer composition may further contain additives conventionally used well known in the art of medical preparation, for example, pharmaceutically acceptable salts.

The humanized chimera antibodies according to the present invention can be administered in the form of the above-described anticancer composition to mammals including human in a dose of 0.2 to 20 mg/kg/day. The dose may vary depending on the age, condition, etc. of patients. The administration of the anticancer composition can be effected by intraveous injection once a day (single administration or consecutive administration) or intermittently one to three times a week or once every two to three weeks.

The antincancer composition is expected to be useful for treating cancer such as melanoma, neuroblastoma and glioma.

The following examples and reference examples are provided to further illustrate the present invention. It is to be understood, however, that the examples are for purpose of illustration only and are not to be construed to limit the invention.

EXAMPLE 1

Construction of Cassette Vector

1. Isolation of Promoter and Enhancer Genes of KM50 Cell-derived Immunoglobulin H Chain (1) Preparation of Chromosomal DNA from KM50 Cells, P3U1 Cells and Rat Kidney Chromosomal DNA was prepared in the following manner in accordance with the procedure disclosed in Molecular Cloning, Maniatis et al., 1989, p9.16.

1.2×10⁸ KM50 cells, 2×10⁸ P3U1 cells (ATCC CRL1597) and 1.6 g of rat kidney (a kidney sample frozen at −80° C. was smashed thoroughly using a mallet) were each suspended in 2 ml of a buffer solution (pH 7.5) containing 10 mM Tris-HCl, 150 mM sodium chloride and 10 mM sodium ethylenediaminetetraacetate (to be referred to as "EDTA" hereinafter). To this suspension were added 0.8 mg of Proteinase K (Sigma Chemical Co.) and 10 mg of sodium lauryl sulfate (to be referred to as "SDS" hereinafter). After incubation at 37° C. for 10 hours, the resulting mixture was extracted with the same volume of phenol (once), chloroform (twice) and ether (once) in this order, and the extract was dialyzed for 10 hours against a buffer solution (pH 7.5) containing 10 mM Tris-HCl and 1 mM EDTA. A DNA solution was recovered from the dialysis tube and Ribonuclease A (Sigma Chemical Co.) was added thereto to give a final concentration of 20 μg/ml. After incubating at 37° C. for 6 hours to decompose RNA completely, the resulting solution was mixed with 15 mg of SDS and 1 mg of Proteinase K and incubated at 37° C. for 10 hours. The thus treated solution was extracted with the same volume of phenol, chloroform and ether (twice for each) in this order, and the extract was dialyzed for 10 hours against a buffer solution (pH 7.5) containing of 10 mM Tris-HCl and 1 mM EDTA. The DNA solution was recovered from the dialysis tube and used as a chromosomal DNA sample. A DNA concentration of each sample was determined by measuring the absorbance at 260 nm and, as a result, it was found that 1.6 mg, 1.5 mg and 1.9 mg of chromosomal DNA was obtained from 1.2×10⁸ KM50 cells, 2×10⁸ P3U1 cells and 1.6 g of rat kidney, respectively.

(2) Identification of Activated Immunoglobulin H Chain Gene in KM50 Cells by Southern Blotting A 3 μg portion of each of the chromosomal DNA samples obtained in the above step (1) from KM50 cells, P3U1 cells and rat kidney was dissolved in 25 μl of a buffer solution containing 10 mM Tris-HCl (pH 7.5), 6 mM magnesium chloride and 100 mM sodium chloride. Each of the thus prepared solution was mixed with 15 units of XbaI (Takara Shuzo Co., Ltd.; all restriction enzymes used in the following experiments were purchased from the same company) and incubated at 37° C. for 2 hours to cleave the chromosomal DNA at the XbaI site. The reaction mixture was subjected to agarose gel electrophoresis, resulting DNA fragments were transferred to a nitrocellulose filter in accordance with the method of Southern et al. (J. Mol. Biol., 98, 503, (1975)) and then subjected to hybridization in the known method (Kameyama et al., FEBS Letters, 244, 301–306 (1989)) using a mouse JH probe which is disclosed in the FEBS Letters article. A band equivalent to about 9.3 kb was observed only in the DNA sample of KM50 cells. In consequence, it was considered that the XbaI fragment of immunoglobulin DNA found in this band contained the activated immunoglobulin H chain gene derived from KM50 cells.

(3) Preparation of KM50 Cell Chromosomal DNA Library

A 60 μg portion of the 50 cell chromosomal DNA obtained in the above step (2) was dissolved in 250 μl of a buffer solution containing 10 mM Tris-HCl (pH 7.5), 6 mM magnesium chloride and 100 mM sodium chloride. The thus prepared solution was mixed with 150 units of XbaI and incubated at 37° C. for 2 hours to cleave the chromosomal DNA at the XbaI site. The reaction mixture was subjected to agarose gel electrophoresis and a 9.3 kb-equivalent fraction was recovered as about 2 μg of 9.3 kb DNA sample of KM50 cells, making use of the DEAE paper method (Maniatis et al., Molecular Cloning, 1989, p6.24). Separately, a 3 μg portion of lambda-ZAP (Stratagene Cloning Systems) to be used as a vector was dissolved in 200 μl of a buffer solution containing 10 mM Tris-HCl (pH 7.5), 6 mM magnesium chloride and 100 mM sodium chloride. The thus prepared solution was mixed with 50 units of XbaI and incubated at 37° C. for 2 hours to cleave the DNA at the XbaI site. The resulting reaction mixture was extracted with phenol-chloroform and then treated with ethanol to precipitate and recover about 3 μg of DNA. The thus recovered DNA sample was dissolved in a 100 μl of 100 mM Tris-HCl buffer (pH 7.5), and the resulting solution was mixed with 1 unit of alkaline phosphatase (Takara Shuzo Co., Ltd.) to effect dephosphorylation of restriction enzyme cleavage ends of the vector DNA. The resulting reaction mixture was extracted with phenol-chloroform and then treated with ethanol to precipitate and recover 2 μg of DNA. The thus recovered DNA sample was dissolved in 10 μl of a buffer solution containing 10 mM Tris-HCl (pH 7.5) and 1 mM EDTA to serve as a vector DNA sample. Next, 0.2 μg of the thus prepared vector DNA sample and 0.2 μg of the KM50 cell-derived 9.3 kb DNA sample were dissolved in 5 μl of a buffer solution containing 66 mM Tris-HCl (pH 7.5), 6.6 mM magnesium chloride, 10 mM dithiothreitol (to be referred to as "DTT" hereinafter) and 0.1 mM adenosine triphosphate (to be referred to as "ATP" hereinafter) (to be referred to as "T4 ligase buffer" hereinafter). The resulting solution was mixed with 175 units of T4 DNA ligase (Takara Shuzo Co., Ltd.) and incubated at 4° C. for 3 days. A 2 μl portion of the resulting reaction mixture was subjected to lambda phage packaging in the known method (Maniatis et al., Molecular Cloning, 1989, p2.95) using GigaPack Gold purchased from Stratagene Cloning Systems. *E. coli* BB4 cells were infected with this phage to obtain 200,000 phage clones. 100,000 out of these phage clones were fixed on nitrocellulose filters in the known method (Maniatis et al., Molecular Cloning, 1989, p2.112).

(4) Selection of Recombinant DNA Containing a Gene of the Activated (Anti-human Serum Albumin) Immunoglobulin H Chain Variable Region in KM50 Cells Two clones showing strong reaction with the ³²P-labeled mouse JH probe at 65° C. were isolated from the 100,000 phage clones prepared in the above step (3) in accordance with the procedure of Kameyama et al. (FEBS Letters, 44, 301–306, 1989). When the phage DNA was recovered in the conventional manner (Maniatis et al., Molecular Cloning, 1939, p2.118–2.169), it was found that the 9.3 kb XbaI fragment of the KM50 cell-derived chromosomal DNA was incorporated into the phage DNA.

(5) Base Sequence of the Gene of the Activated (Anti-human Serum Albumin) Immunoglobulin H Chain Variable Region in KM50 Cells Restriction enzyme cleavage maps of the two clones obtained in the above step (4) was prepared by digesting them with various restriction enzymes and it was found that completely the same DNA fragment (9.3 kb) has been inserted into these clones (FIG. 1). Next, base sequence of a part of the 9.3 kb DNA fragment, which was considered to contain the promoter and variable regions of the rat immunoglobulin H chain, was determined in accordance with the Sanger method (Sanger et al., Proc. Natl. Acad. Sci. U.S.A., 74, 5463 (1977); M13 Cloning and Sequencing Handbook, Amersham). In SEQ ID NO: 1, a region containing octamer sequences such as ATGCAAAT and TATA box sequences such as TTGAAAA and the like can be regarded as the immunoglobulin promoter region.

2. Construction of Heterologous Protein Expression Vector Using Promoter and Enhancer of the Activated (Anti-human Serum Albumin) Immunoglobulin H Chain Variable Region in KM50 Cells (1) Construction of pKMB11

Figure 2:
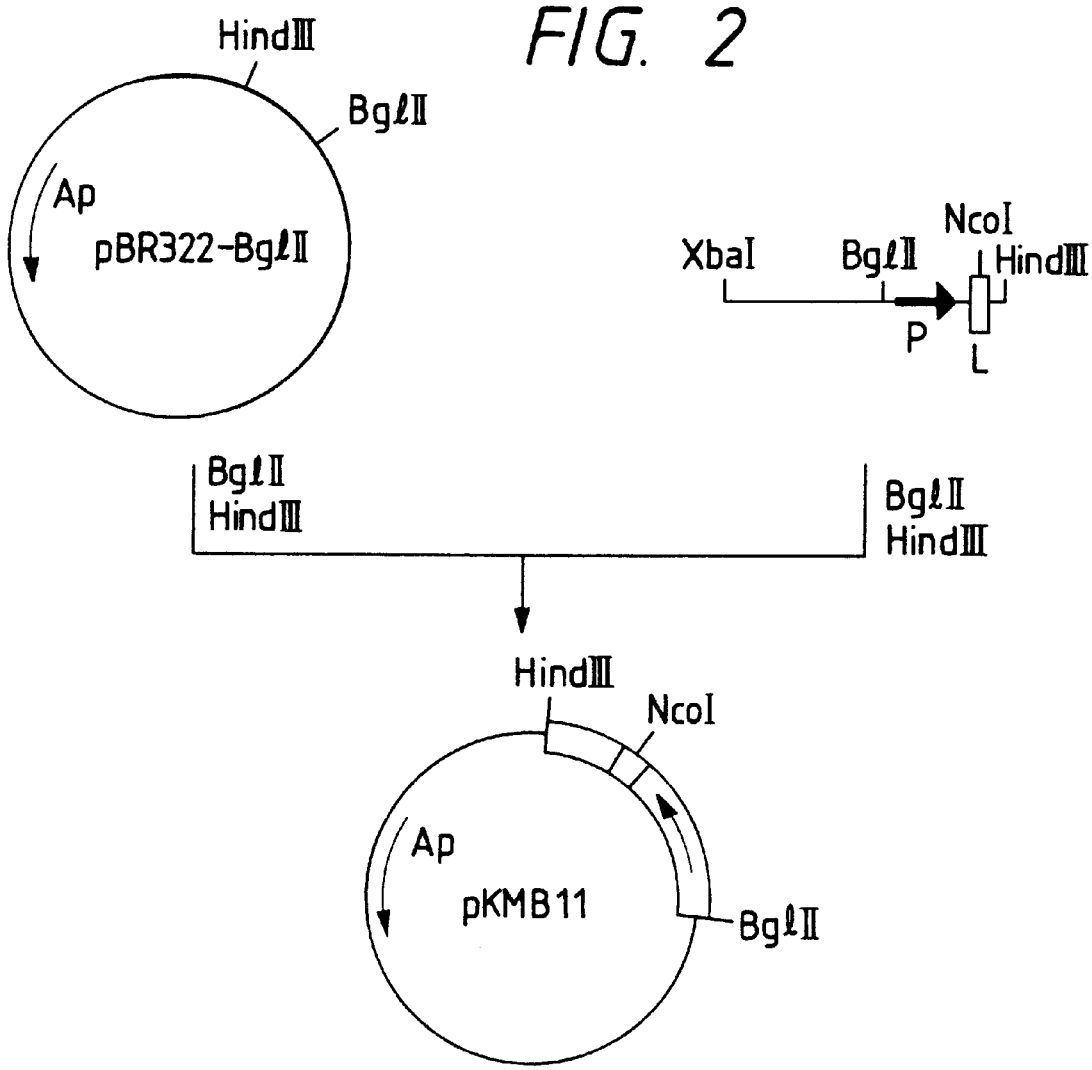
FIG. 2 shows a construction scheme for plasmid pKMB11.

A 1 μg portion of the 9.3 kb fragment of the immunoglobulin H chain variable region gene obtained in 1-(5) was dissolved in 30 μl of a buffer solution containing 10 mM Tris-HCl (pH 7.5), 6 mM magnesium chloride and 100 mM sodium chloride. The thus prepared solution was mixed with 10 units of BglII and 10 units of HindIII and incubated at 37° C. for 2 hours to cleave the DNA fragment at the BglII and HindIII sites. The resulting reaction mixture was subjected to agarose gel electrophoresis and 0.01 μg of a DNA fragment containing 0.8 kb immunoglobulin promoter was recovered. Separately, a 1 μg portion of a plasmid pBR322-BglII (Kuwana et al., FEBS Letters, 219, 360 (1987)) was dissolved in 30 μl of a buffer solution containing 10 mM Tris-HCl (pH 7.5), 6 mM magnesium chloride and 100 mM sodium chloride. The thus prepared solution was mixed with 10 units of BglII and 10 units of HindIII and incubated at 37° C. for 2 hours to cleave the plasmid at the BglII and HindIII sites. The resulting reaction mixture was subjected to agarose gel electrophoresis, a DNA fragment of about 4.2 kb was recovered. A 0.1 μg portion of the thus obtained pBR322-BglII derived DNA fragment of about 4.2 kb and 0.01 μg of the immunoglobulin promoter-containing DNA fragment were dissolved in 20 μl of a T4 ligase buffer, and the resulting solution was mixed with 175 units of T4 DNA ligase (Takara Shuzo Co., Ltd.) and incubated at 4° C. for 24 hours. Using the resulting reaction mixture, transformation of *E. coli* HB101 (J. Mol. Biol., 41, 459 (1969)) was carried out in accordance with the method of Scott et al. (M. Shigesada, Saibo Kogaku, 2, 616 (1983)) to isolate a colony having ampicillin resistance (to be referred to as "ApR" hereinafter). Plasmid DNA was recovered from the colony to obtain pKM11 as shown in FIG. 2.

(2) Construction of pKMD6

Figure 3:
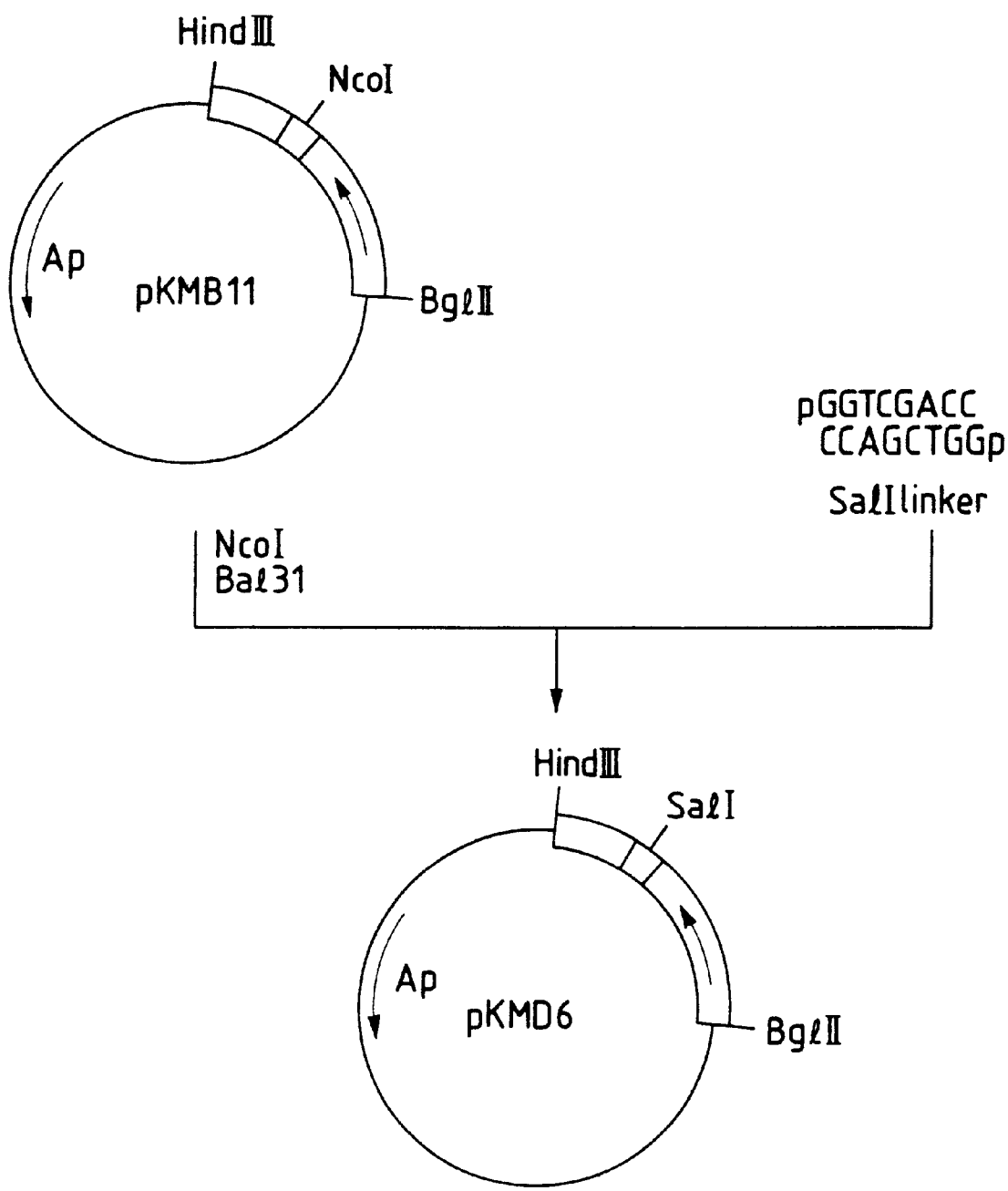
FIG. 3 shows a construction scheme for plasmid pkMD6.

In order to establish an appropriate restriction enzyme recognition site in downstream region of the immunoglobulin promoter, the plasmid pKMB11 constructed in the above step (1) was digested with nuclease BAL31 from the NcoI site. A 10 μg portion of the plasmid pKMB11 was dissolved in 100 μl of a buffer solution containing 10 mM Tris-HCl (pH 7.5), 6 mM magnesium chloride and 50 mM potassium chloride. The thus prepared solution was mixed with 30 units of NcoI and incubated at 37° C. for 2 hours to cleave the plasmid at the NcoI site. The resulting reaction mixture was extracted with phenol and chloroform and treated with ethanol. The thus precipitated DNA fragments were dissolved in 100 μl of BAL31 buffer which contained 20 mM Tris-HCl (pH 8.0), 600 mM sodium chloride, 12 mM calcium chloride, 12 mM magnesium chloride and 1 mM EDTA, and the resulting solution was mixed with 0.25 unit of BAL31 (Bethesda Research Laboratories, Inc. (BRL)) and incubated at 37° C. for 5 seconds. The reaction was stopped by extracting the reaction mixture with phenol. After extraction with chloroform and precipitation with ethanol, 1 μg of DNA was recovered. A 0.1 μg portion of the thus obtained DNA sample and 0.01 μg of a synthetic DNA linker SalI were dissolved in 20 μl of the T4 ligase buffer, and the resulting solution was mixed with 175 units of T4 DNA ligase and incubated at 4° C. for 24 hours. Using the resulting reaction mixture, transformation of *E. coli* HB101 was carried out in accordance with the method of Scott et al. to isolate an ApR colony. Plasmid DNA was recovered from the colony to obtain pKMD6 as shown in FIG. 3. The base sequence of the BAL31-digested portion of this plasmid was determined in accordance with the Sanger method and it was found that bases up to the third base (the 303 position base in the SEQ ID NO: 1) upstream from the initiation codon ATG of the immunoglobulin gene.

(3) Construction of pEPKMA1, pEPKMB1 and pAGE501

Since original promoter and enhancer of the immunoglobulin gene are separated from each other, it is necessary to construct a vector in which the promoter and enhancer are connected together so that it can be used as a vector for the expression of a heterologous protein. The following manipulation was carried out to construct such vectors.

Figure 4:
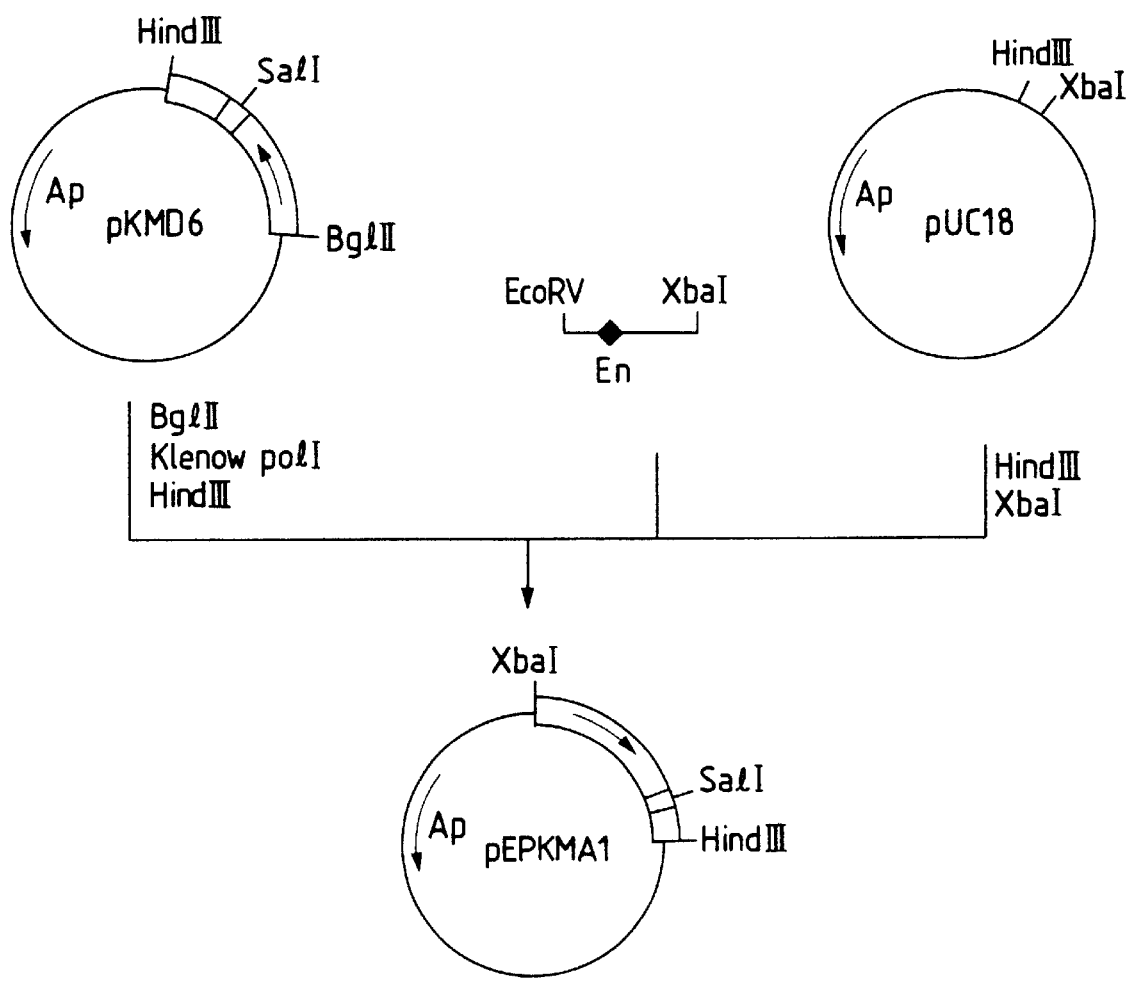
FIG. 4 shows a construction scheme for plasmid pEP-KMA1.

A 1 μg portion of the 9.3 kb fragment of the immunoglobulin H chain variable region gene obtained in 1-(5) was dissolved in 30 μl of a buffer solution containing 10 mM Tris-HCl (pH 7.5), 6 mM magnesium chloride and 100 mM sodium chloride. The thus prepared solution was mixed with 10 units of EcoRV and 10 units of XbaI and incubated at 37° C. for 2 hours to cleave the DNA fragment at the EcoRV and XbaI sites. The resulting reaction mixture was subjected to agarose gel electrophoresis and 0.1 μg of a DNA fragment of about 1 kb containing the immunoglobulin enhancer region was recovered. Separately, a 1 μg portion of the plasmid pKMD6 obtained in the above step (2) was dissolved in 100 μl of a buffer solution containing 10 mM Tris-HCl (pH 7.5) 6 mM magnesium chloride and 100 mM sodium chloride. The thus prepared solution was mixed with 10 units of BglII and incubated at 37° C. for 2 hours to cleave the plasmid at the BglII site. The resulting reaction mixture was extracted with phenol and chloroform and precipitated with ethanol. The thus precipitated DNA fragments were dissolved in 40 μl of DNA polymerase I buffer containing 50 mM Tris-HCl (pH 7.5), 10 mM magnesium chloride, 0.1 mM dATP (deoxyadenosine triphosphate), 0.1 mM dCTP (deoxycytidine triphosphate), 0.1 mM dGTP (deoxyguanosine triphosphate) and 0.1 mM dTTP (deoxythymidine triphosphate). The resulting solution was mixed with 6 units of *E. coli* DNA polymerase I Klenow fragment and incubated at 16° C. for 90 minutes to convert the cohesive 5'-end formed by the BglII digestion into blunt end. The reaction was stopped by extracting the reaction mixture with phenol. After extraction with chloroform and precipitation with ethanol, the resulting DNA fragments were dissolved in 30 μl of a buffer solution containing 10 mM Tris-HCl (pH 7.5), 6 mM magnesium chloride and 50 mM sodium chloride. The thus prepared solution was mixed with 10 units of HindIII and incubated at 37° C. for 2 hours to cleave the DNA fragment at the HindIII site. The resulting reaction mixture was subjected to agarose gel electrophoresis, 0.1 μg of a DNA fragment of about 0.8 kb containing the immunoglobulin promoter region was recovered. Next, a 0.2 μg portion of plasmid pUC18 (Messing, Methods in Enzymology, 101, 20 (1983)) was dissolved in 30 μl of a buffer solution containing 10 mM Tris-HCl (pH 7.5), 6 mM magnesium chloride and 100 mM sodium chloride. The thus Prepared solution was mixed with 10 units of HindIII and 10 units of XbaI and incubated at 37° C. for 2 hours to cleave the plasmid at the HindIII and XbaI sites. The resulting reaction mixture was subjected to agarose gel electrophoresis, 0.1 μg of a DNA fragment of about 2.7 kb was recovered. A 0.1 μg portion of the thus obtained pKMD6-derived 0.8 kb DNA fragment, 0.02 μg of the DNA fragment containing the immunoglobulin enhancer region and 0.1 μg of the pUC18 fragment were dissolved in 20 μl of the T4 ligase buffer, and the resulting solution was mixed with 175 units of T4 DNA ligase and incubated at 4° C. for 24 hours. Using the resulting reaction mixture, transformation of *E. coli* HB101 was carried out to isolate an ApR colony. Plasmid DNA was recovered from the colony to obtain pEPKMA1 as shown in FIG. 4.

Next, a 1 μg portion of the plasmid pEPKMA1 was dissolved in 100 μl of a buffer solution containing 10 mM Tris-HCl (pH 7.5), 6 mM magnesium chloride and 100 mM sodium chloride. The thus prepared solution was mixed with 10 units of XbaI and incubated at 37° C. for 2 hours to cleave the plasmid at the XbaI site. The resulting reaction mixture was extracted with phenol and chloroform and precipitated with ethanol. The thus precipitated DNA fragments were dissolved in 40 μl of the aforemetioned DNA polymerase I buffer solution, and the resulting solution was mixed with 6 units of *E. coli* DNA polymerase I Klenow fragment and incubated at 16° C. for 90 minutes to convert the cohesive 5'-end formed by the XbaI digestion into blunt end. The reaction was stopped by extracting the reaction mixture with phenol. After extraction with chloroform and precipitation with ethanol, DNA fragments was recovered. The thus obtained DNA sample and 0.01 μg of a synthetic DNA XhoI linker (Takara Shuzo Co., Ltd.) were dissolved in 20 μl of the T4 ligase buffer, and the resulting solution was mixed with 175 units of T4 DNA ligase and incubated at 4° C. for 24 hours. Using the resulting reaction mixture, transformation of *E. coli* HB101 was carried out to isolate an ApR colony. Plasmid DNA was recovered from the colony to obtain pEPKMB1 as shown in FIG. 5.

Next, SV40 early gene promoter and enhancer regions (to be referred to as "$P_{SE}$" hereinafter) of an expression vector pAGE107 for use in the expression of heterologous genes in animal cells (Miyaji et al., Cytotechnology, 3, 133–140 (1990)) were converted into KM50-derived immunoglobulin H chain promoter and enhancer (to be referred to as "$P_{IH}$" hereinafter) of pEPKMB1 in the following manner.

Figure 6:
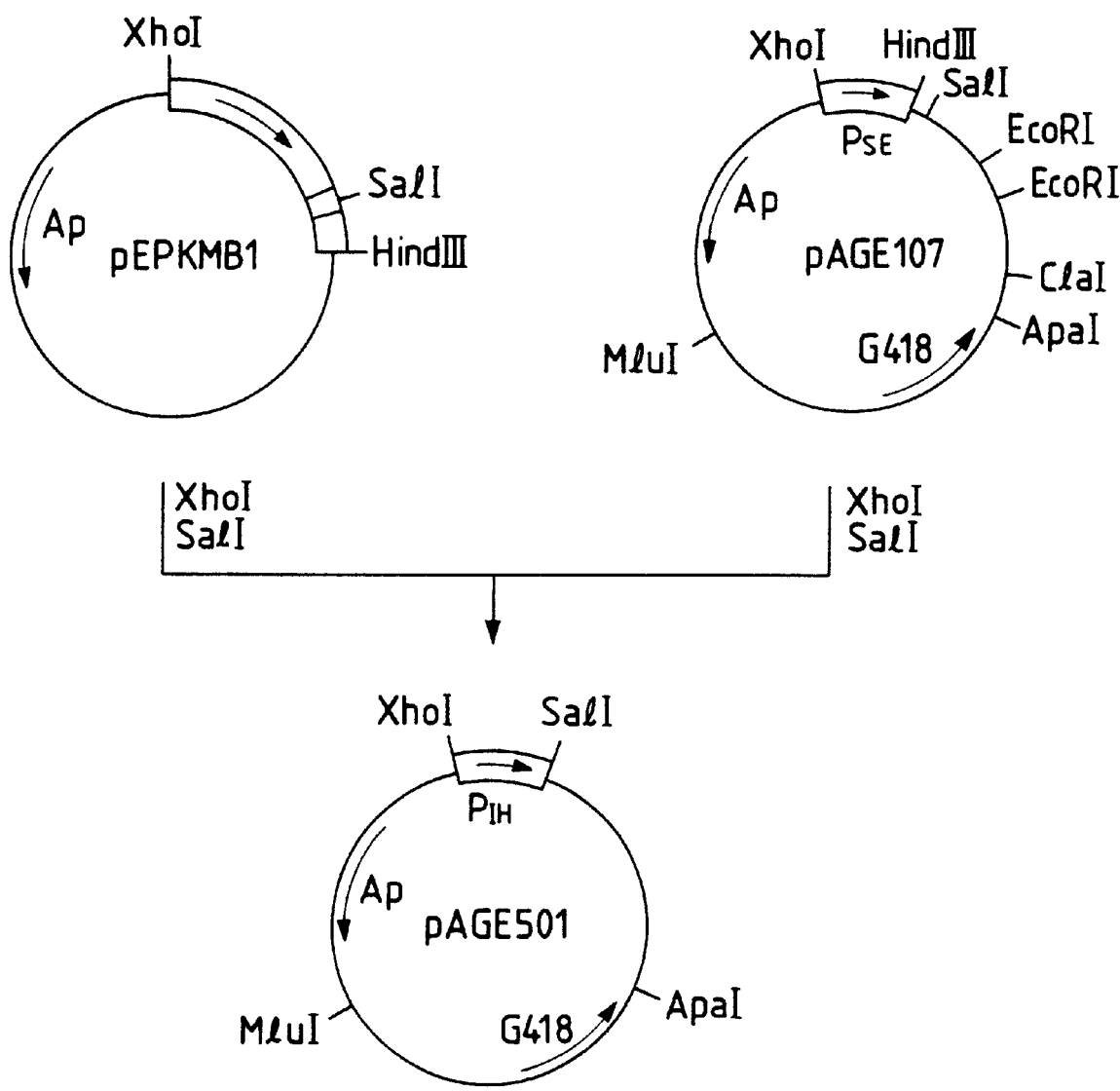
FIG. 6 shows a construction scheme for plasmid pAGE501.

A 1 μg portion of the plasmid pAGE107 was dissolved in 30 μl of a buffer solution containing 10 mM Tris-HCl (pH 7.5), 6 mM magnesium chloride and 150 mM sodium chloride. The thus prepared solution was mixed with 10 units of SalI and 10 units of XhoI and incubated at 37° C. for 2 hours to cleave the plasmid at the SalI and XhoI sites. The resulting reaction mixture was subjected to agarose gel electrophoresis and 0.5 μg of a DNA fragment of about 5.95 kb containing G418 resistance gene was recovered. Next, a 1 μg portion of the plasmid pEPKMB1 was dissolved in 30 μl of a buffer solution containing 10 mM Tris-HCl (pH 7.5), 6 mM magnesium chloride and 150 mM sodium chloride. The thus prepared solution was mixed with 10 units of SalI and 10 units of XhoI and incubated at 37° C. for 2 hours to cleave the plasmid at the SalI and XhoI sites. The resulting reaction mixture was subjected to agarose gel electrophoresis and 0.1 μg of a DNA fragment of about 1.7 kb containing immunoglobulin promoter and enhancer regions was recovered. A 0.1 μg portion of the thus obtained pAGE107-derived 5.95 kb DNA fragment and 0.02 μg of the DNA fragment containing immunoglobulin promoter and enhancer regions were dissolved in 20 μl of the T4 ligase buffer, and the resulting solution was mixed with 175 units of T4 DNA ligase and incubated at 4° C. for 24 hours. Using the resulting reaction mixture, transformation of *E. coli* HB101 was carried out to isolate an ApR colony. Plasmid DNA was recovered from the colony to obtain pAGE501 as shown in FIG. 6.

(4) Construction of pAGE109

One of the two EcoRI cleavage sites in plasmid pAGE106 was deleted in the following manner to construct pAGE109.

A 2 μg portion of the expression vector pAGE106 for use in the expression of heterologous genes in animal cells (JP-A 3-22979 or EP-A-0 405 285) was dissolved in 100 μl of a buffer solution containing 10 mM Tris-HCl (pH 7.5), 6 mM magnesium chloride and 50 mM sodium chloride. The thus prepared solution was mixed with 10 units of EcoRI and 10 units of SacI and incubated at 37° C. for 4 hours. The resulting reaction mixture was subjected to agarose gel electrophoresis and about 1.5 μg of a pAGE106 DNA fragment (4.3 kb) was recovered which contained the SV40 early gene promoter and G418 resistance gene cleaved with EcoRI and SacI. The thus recovered DNA fragment was dissolved in 40 μl of the DNA polymerase I buffer solution, and the resulting solution was mixed with 5 units of *E. coli* DNA polymerase I large fragment and incubated at 16° C. for 2 hours to convert the cohesive 3'-end formed by the SacI digestion and the cohesive 5'-end formed by the EcoRI digestion into blunt ends. The resulting reaction mixture was extracted with phenol and chloroform and then treated with ethanol. The thus precipitated sample was dissolved in 20 μl of the T4 ligase buffer, and the resulting solution was mixed with 350 units of T4 DNA ligase and incubated at 4° C. for 4 hours. Using the thus obtained recombinant plasmid DNA, transformation of *E. coli* HB101 was carried out to obtain plasmid pAGE109 as shown in FIG. 7.

(5) Construction of pAGE502

Plasmid pAGE502 was constructed in the following manner in order to convert the SV40 promoter and enhancer of pAGE107 into immunoglobulin H chain promoter and enhancer.

A 2 μg portion of the plasmid pAGE107 disclosed in JP-A-3-22979 or EP-A-0 405 285 was dissolved in 100 μl of a buffer solution containing 10 mM Tris-HCl (pH 7.5), 6 mM magnesium chloride and 50 mM sodium chloride. The thus prepared solution was mixed with 10 units of HindIII and incubated at 37° C. for 4 hours. The resulting reaction mixture was subjected to phenol-chloroform extraction and ethanol precipitation and the thus recovered sample was dissolved in 40 μl of the DNA polymerase I buffer solution. The resulting solution was mixed with 5 units of *E. coli* DNA polymerase I Klenow fragment and incubated at 16° C. for 2 hours to convert the cohesive 5'-end formed by the HindIII digestion into blunt end. The resulting reaction mixture was extracted with phenol and chloroform and then treated with ethanol. The thus precipitated sample was dissolved in 30 μl of a buffer solution containing 10 mM Tris-HCl (pH 7.5), 6 mM magnesium chloride and 100 mM sodium chloride. The thus prepared solution was mixed with 10 units of XhoI and incubated at 37° C. for 4 hours. The resulting reaction mixture was subjected to agarose gel electrophoresis and about 1.5 μg of a pAGE107 DNA fragment of about 5.95 kb was obtained which contained G418 resistance gene and ApR gene cleaved with XhoI and HindIII.

Next, a 2 μg portion of the plasmid pAGE501 obtained in the above step (3) was dissolved in 100 μl of a buffer solution containing 10 mM Tris-HCl (pH 7.5), 6 mM magnesium chloride and 175 mM sodium chloride. The thus prepared solution was mixed with 10 units of SalI and incubated at 37° C. for 4 hours. After subjecting the resulting reaction mixture to phenol-chloroform extraction and ethanol precipitation, the thus recovered sample was dissolved in 40 μl of the DNA polymerase buffer solution. The resulting solution was mixed with 5 units of *E. coli* DNA polymerase I Klenow fragment and incubated at 16° C. for 2 hours to convert the cohesive 5'-end formed by the SalI digestion into blunt end. The resulting reaction mixture was extracted with phenol and chloroform and then treated with ethanol. The thus precipitated sample was dissolved in 30 μl of a buffer solution containing 10 mM Tris-HCl (pH 7.5), 6 mM magnesium chloride and 100 mM sodium chloride. The thus prepared solution was mixed with 10 units of XhoI and incubated at 37° C. for 4 hours. The resulting reaction mixture was subjected to agarose gel electrophoresis and about 0.2 μg of a pAGE501 DNA a fragment of about 1.8 kb was obtained which contained KM50 immunoglobulin H chain promoter and enhancer genes cleaved with XhoI and SalI.

Figure 8:
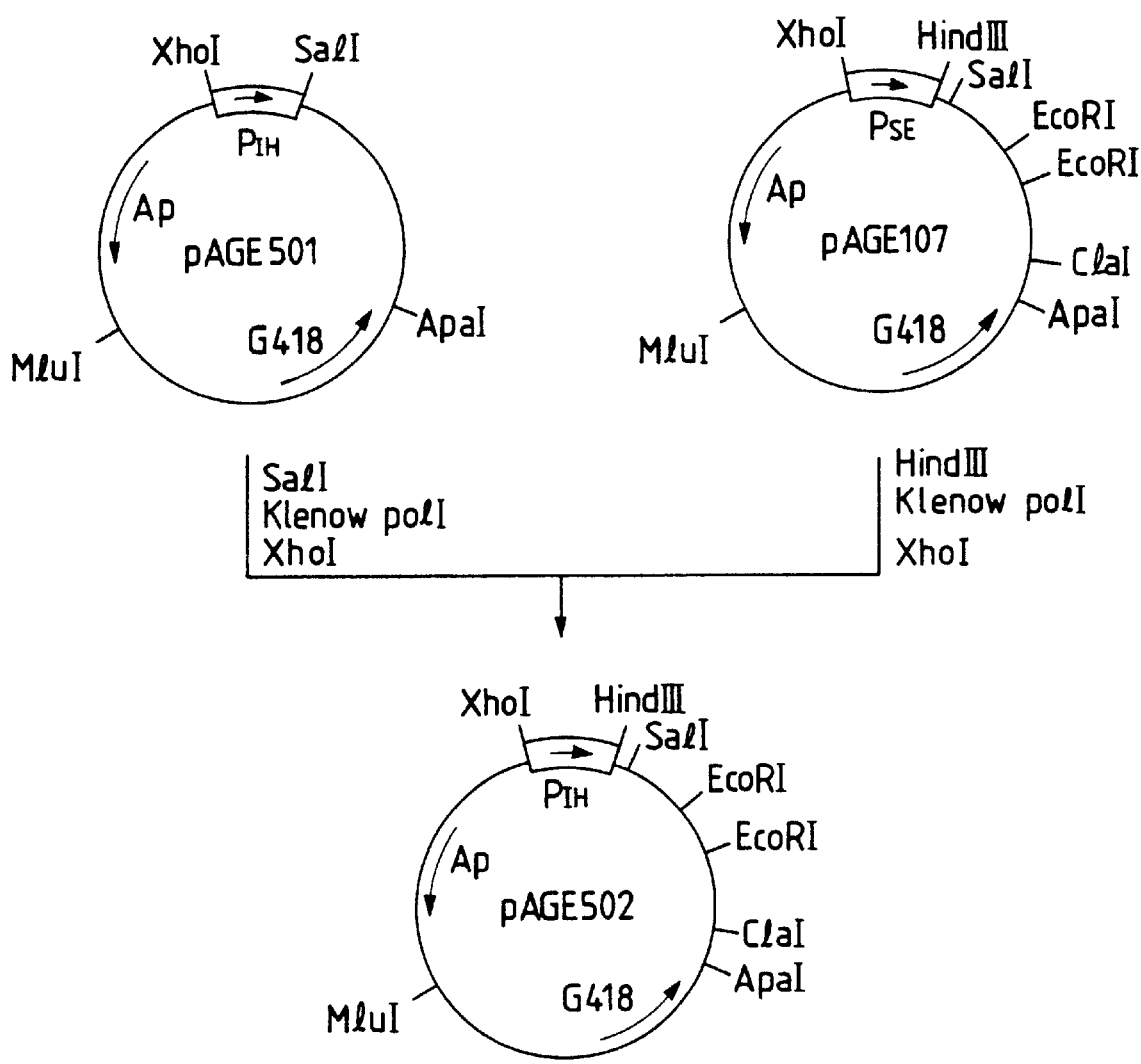
FIG. 8 shows a construction scheme for plasmid pAGE502.

Next, 0.1 μg of the thus obtained pAGE107 HindIII-XhoI fragment (about 5.95 kb) and 0.1 μg of the pAGE501 SalI-XhoI fragment (about 1.8 kb) were dissolved in 20 μl of the T4 ligase buffer, and the resulting solution was mixed with 350 units of T4 DNA ligase and incubated at 4° C. for 24 hours. Using the thus obtained recombinant plasmid DNA, transformation of *E. coli* HB101 was carried out to obtain plasmid pAGE502 as shown in FIG. 8.

(6) Construction of pAGE503

One of the two EcoRI cleavage sites in plasmid pAGE502 was deleted in the following manner to construct pAGE503.

A 2 μg portion or the plasmid pAGE109 obtained in the above step (4) was dissolved in 30 μl of a buffer solution containing 10 mM Tris-HCl (pH 7.5), 6 mM magnesium chloride and 50 mM sodium chloride. The thus prepared solution was mixed with 10 units of HindIII and 10 units of ClaI and incubated at 37° C. for 4 hours. The resulting reaction mixture was subjected to agarose gel electrophoresis and about 0.2 μg of a pAGE109 DNA fragment of about 1 kb was recovered which contained the poly(A) signal gene of beta-globin and SV40 early genes cleaved with ClaI and HindIII.

Figure 9:
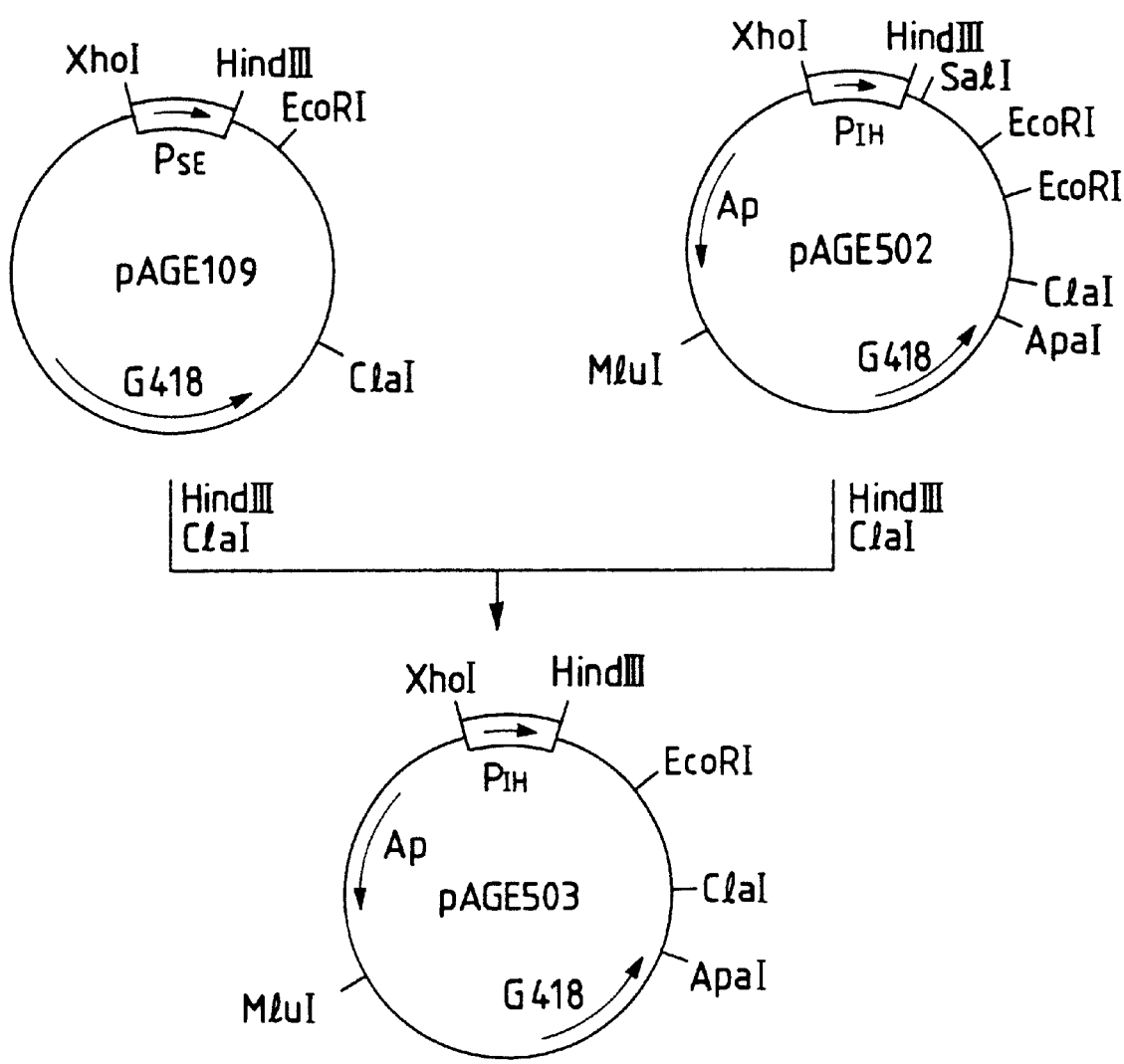
FIG. 9 shows a construction scheme for plasmid pAGE503.

Next, a 2 μg portion of the plasmid pAGE502 obtained in the above step (5) was dissolved in 30 μl of a buffer solution containing 10 mM Tris-HCl (pH 7.5), 6 mM magnesium chloride and 50 mM sodium chloride. The thus prepared solution was mixed with 10 units of HindIII and 10 units of ClaI and incubated at 37° C. for 4 hours. The resulting reaction mixture was subjected to agarose gel electrophoresis and then to the aforementioned DEAE paper method to recover about 1 μg of a pAGE502 DNA fragment of about 6.1 kb which contained KM50 immunoglobulin H chain promoter and enhancer genes, ApR gene and G418 resistance gene cleaved with HindIII and ClaI. Next, 0.1 μg of the thus obtained pAGE109 HindIII-ClaI fragment (about 1 kb) and 0.1 μg of the pAGE-502 HindIII-ClaI fragment (about 6.1 kb) were dissolved in 20 μl of the T4 ligase buffer, and the resulting solution was mixed with 350 units of T4 DNA ligase and incubated at 4° C. for 24 hours. Using the thus obtained recombinant plasmid DNA, transformation of *E. coli* HB101 was carried out to obtain plasmid pAGE503 as shown in FIG. 9.

(7) Construction of pSE1d1

A dhfr gene was introduced into plasmid pAGE107 in the following manner to construct plasmid pSE1d1.

A 2 μg portion of the plasmid pAGE107 disclosed in JP-A 3-22979 or EP-A-0 405 285 was dissolved in 100 μl of a buffer solution containing 100 mM Tris-HCl (pH 7.5), 6 mM magnesium chloride and 50 mM sodium chloride. The thus prepared solution was mixed with 10 units of EcoRI and incubated at 37° C. for 4 hours. After subjecting the resulting reaction mixture to phenol-chloroform extraction and ethanol precipitation, the thus recovered sample was dissolved in 40 μl of the DNA polymerase I buffer solution. The resulting solution was mixed with 5 units of *E. coli* DNA polymerase I Klenow fragment and incubated at 16° C. for 2 hours to convert the cohesive 5'-end formed by the EcoRI digestion into blunt end. The resulting reaction mixture was extracted with phenol and chloroform and then treated with ethanol. The thus precipitated sample was dissolved in 30 μl of a buffer solution which was composed of 10 mM Tris-HCl (pH 7.5), 6 mM magnesium chloride and 50 mM sodium chloride. The thus prepared solution was mixed with 10 units of HindIII and incubated at 37° C. for 4 hours. The resulting reaction mixture was subjected to agarose gel electrophoresis and about 1.5 μg of a pAGE107 DNA fragment of about 5.6 kb was recovered which contained G418 resistance gene and ApR gene cleaved with EcoRI and HindIII.

Next, a 2 μg portion of a plasmid pSV2-dhfr (Subramani et al., Mol. Cell. Biology, 1, 854 (198)) was dissolved in 100 μl of a buffer solution containing 10 mM Tris-HCl (pH 7.5), 6 mM magnesium chloride and 100 mM sodium chloride. The thus prepared solution was mixed with 10 units of BglII and incubated at 37° C. for 4 hours. After subjecting the resulting reaction mixture to phenol-chloroform extraction and ethanol precipitation, the thus recovered sample was dissolved in 40 μl of the DNA polymerase I buffer solution. The resulting solution was mixed with 5 units of *E. coli* DNA polymerase I Klenow fragment and incubated at 16° C. for 2 hours to convert the cohesive 5'-end formed by the BclII digestion into blunt end. The resulting reaction mixture was extracted with phenol and chloroform and then treated with ethanol. The thus precipitated sample was dissolved in 30 μl of a buffer solution containing 10 mM Tris-HCl (pH 7.5), 6 mM magnesium chloride and 100 mM sodium chloride. The thus prepared solution was mixed with 10 units of HindIII and incubated at 37° C. for 4 hours. The resulting reaction mixture was subjected to agarose gel electrophoresis, about 0.2 μg of a pSV2-dhfr DNA fragment of about 0.76 kb was recovered which contained dhfr gene cleaved with BglII and HindIII.

Figure 10:
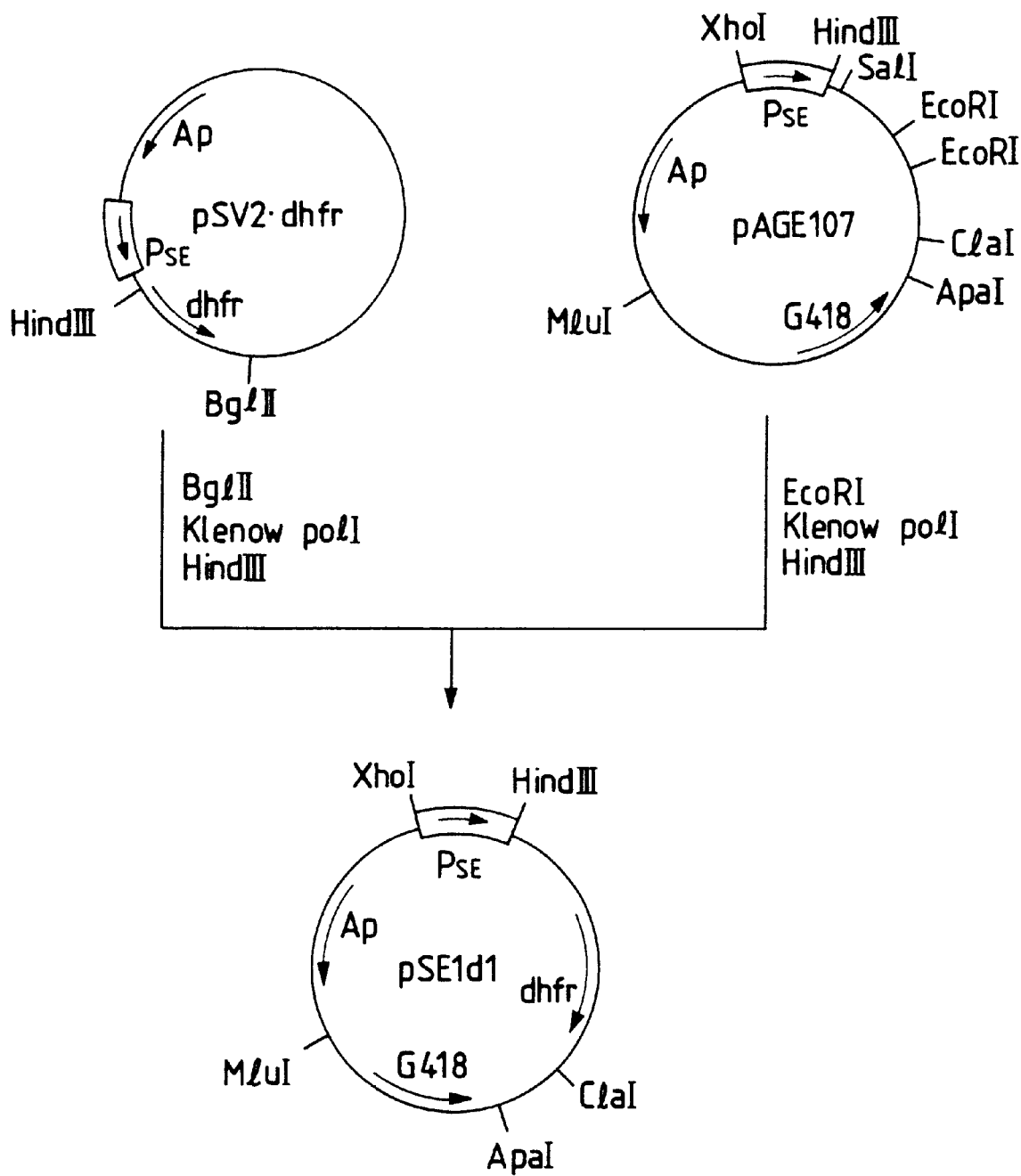
FIG. 10 shows a construction scheme for plasmid pSEd1.

Next, 0.1 μg of the thus obtained pAGE107 HindIII-EcoRI fragment (about 5.6 kb) and 0.1 μg the pSV2-dhfr BglII-HindIII fragment (about 0.76 kb) were dissolved in 20 μl of the T4 ligase buffer, and the resulting solution was mixed with 350 units of T4 DNA ligase and incubated at 4° C. for 24 hours. Using the thus obtained recombinant plasmid DNA, transformation of *E. coli* HB101 was carried out to obtain plasmid pSE1d1 as shown in FIG. 10.

(8) Construction of pSE1d2

The HindIII cleavage site was removed from the plasmid pSE1d1 in the following manner to construct plasmid pSE1d2.

A 2 μg portion of the plasmid pSE1d1 obtained in the above step (7) was dissolved in 100 μl of a buffer solution containing 10 mM Tris-HCl (pH 7.5), 6 mM magnesium chloride and 50 mM sodium chloride. The thus prepared solution was mixed with 10 units of HindIII and incubated at 37° C. for 4 hours. After subjecting the resulting reaction mixture to phenol-chloroform extraction and ethanol precipitation, the thus recovered sample was dissolved in 40 μl of the DNA polymerase I buffer solution. The resulting solution was mixed with 5 units of *E. coli* DNA polymerase I Klenow fragment and incubated at 16° C. for 2 hours to convert the cohesive 5'-end formed by the HindIII digestion into blunt end. The resulting reaction mixture was extracted with phenol and chloroform and then treated with ethanol. The thus precipitated sample was dissolved in 20 μl of the T4 ligase buffer, and the resulting solution was mixed with 350 units of T4 DNA ligase and incubated at 4° C. for 24 hours. Using the thus obtained recombinant plasmid DNA, transformation of *E. coli* HB101 was carried out to obtain plasmid pSE1d2 as shown in FIG. 11.

(9) Construction of pIg1SE1d2

The dhfr gene was introduced into plasmid pAGE503 in the following manner to construct plasmid pIg1SE1d2.

A 2 μg portion of the plasmid pAGE503 obtained in the above step (6) was dissolved in 100 μl of a buffer solution containing 100 mM. Tris-HCl (pH 7.5), 6 mM magnesium chloride and 50 mM sodium chloride. The thus prepared solution was mixed with 10 units of ClaI and incubated at 37° C. for 4 hours. After subjecting the resulting reaction mixture to phenol-chloroform extraction and ethanol precipitation, the thus recovered sample was dissolved in 40 μl of the DNA polymerase I buffer solution. The resulting solution was mixed with 5 units of *E. coli* DNA polymerase I Klenow fragment and incubated at 16° C. for 2 hours to convert the cohesive 5'-end formed by the ClaI digestion into blunt end. The resulting reaction mixture was extracted with phenol and chloroform and then treated with ethanol. The thus precipitated sample was dissolved in 30 μl of a buffer solution containing 10 mM Tris-HCl (pH 7.5), 6 mM magnesium chloride and 50 mM sodium chloride. The thus prepared solution was mixed with 10 units of MluI and incubated at 37° C. for 4 hours. The resulting reaction mixture was subjected to agarose gel electrophoresis and about 1 μg of a pAGE503 DNA fragment of about 5.4 kb was recovered which contained the KM50 immunoglobulin H chain promoter and enhancer genes cleaved with ClaI and MluI.

Next, a 2 μg portion of the plasmid pSEld2 obtained in the above step (8) was dissolved in 100 μl of a buffer solution containing 10 mM Tris-HCl (pH 7.5), 6 mM magnesium chloride and 100 mM sodium chloride. The thus prepared solution was mixed with 10 units of XhoI and incubated at 37° C. for 4 hours. The resulting reaction mixture was subjected to phenol-chloroform extraction and ethanol precipitation and the thus recovered sample was dissolved in 40 μl of the DNA polymerase I buffer solution. The resulting solution was mixed with 5 units of *E. coli* DNA polymerase I Klenow fragment and incubated at 16° C. for 2 hours to convert the cohesive 5'-end formed by the XhoI digestion into blunt end. The resulting reaction mixture was extracted with phenol and chloroform and then treated with ethanol. The thus precipitated sample was dissolved in 30 μl of a buffer solution containing 10 mM Tris-HCl (pH 7.5), 6 mM magnesium chloride and 100 mM sodium chloride. The thus prepared solution was mixed with 10 units of MluI and incubated at 37° C. for 4 hours. The resulting reaction mixture was subjected to agarose gel electrophoresis and about 1 μg of a pSEld2 DNA fragment of about 3.8 kb was recovered which contained dhfr gene cleaved with XhoI and MluI.

Figure 12:
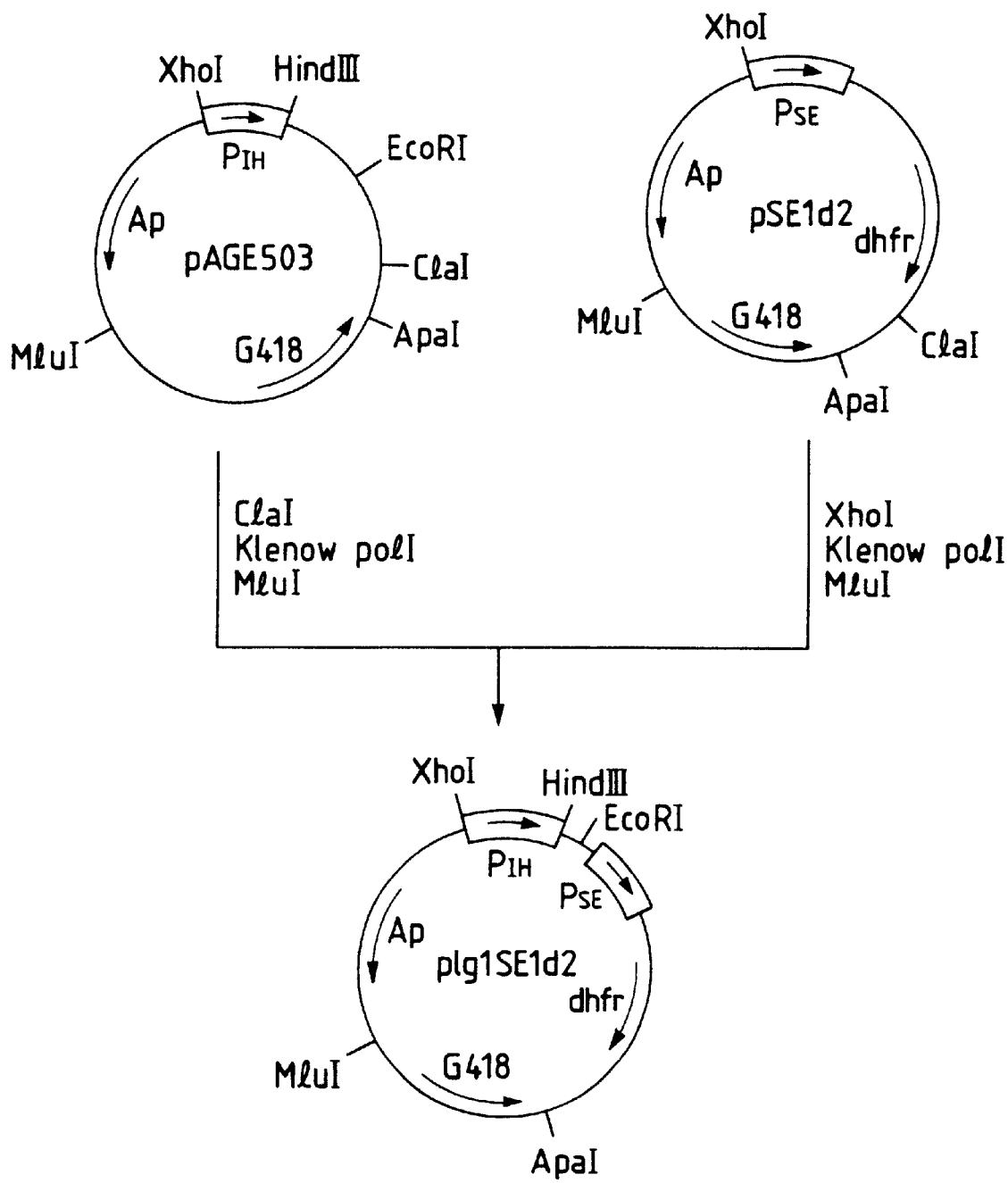
FIG. 12 shows a construction scheme for plasmid pIG1SE1d2.

Next, 1 μg of the thus obtained pAGE503 ClaI-MluI fragment (about 5.4 kb) and 1 μg of the pSEld2 XhoI-MluI fragment (about 3.8 kb) were dissolved in 20 μl of the T4 ligase buffer, and the resulting solution was mixed with 350 units of T4 DNA ligase and incubated at 4° C. for 24 hours. Using the thus obtained recombinant plasmid DNA, transformation of *E. coli* HB101 was carried out to obtain plasmid pIg1SEld2 as shown in FIG. 12.

(10) Construction of pIg1SEld3

The ApaI cleavage site was removed from the plasmid pIg1SEld2 in the following manner to construct plasmid pIg1SEld3.

A 2 μg portion of the plasmid pIg1SEld2 obtained in, the above step (9) was dissolved in 100 μl of a buffer solution containing 10 my Tris-HCl (pH 7.5) and 6 mM magnesium chloride. The thus prepared solution was mixed with 10 units of ApaI and incubated at 37° C. for 4 hours. After subjecting the resulting reaction mixture to phenol-chloroform extraction and ethanol precipitation, the thus recovered sample was dissolved in 40 μl of the DNA polymerase I buffer solution. The resulting solution was mixed with 5 units of *E. coli* DNA polymerase I Klenow fragment and incubated at 16° C. for 2 hours to convert the cohesive 3'-end formed by the ApaI digestion into blunt end. The resulting reaction mixture was extracted with phenol and chloroform and then treated with ethanol. The thus precipitated sample was dissolved in 20 μl of the T4 ligase buffer, and the resulting solution was mixed with 350 units of T4 DNA ligase and incubated at 4° C. for 24 hours. Using the thus obtained recombinant plasmid DNA, transformation of *E. coli* HB101 was carried out to obtain plasmid pIg1SEld3 as shown in FIG. 13.

(11) Construction of pIg1SEld4

In order to establish a cloning site between HindIII cleavage site and EcoRI cleavage site of the plasmid pIg1SEld3, plasmid pIg1SEld4 was constructed by inserting the synthetic DNA shown in SEQ ID NO: 5 into the plasmid pIg1SEld3 in the following manner.

A 2 μg portion of the plasmid pIg1SEld3 obtained in the above step (10) was dissolved in 30 μl of a buffer solution containing 10 mM Tris-HCl (pH 7.5), 6 mM magnesium chloride and 50 mM sodium chloride. The thus prepared solution was mixed with 10 units of HindIII and 10 units of EcoRI and incubated at 37° C. for 4 hours. The resulting reaction mixture was subjected to agarose gel electrophoresis and about 1 μg of a pIg1SEld3 DNA fragment of about 9.2 kb was recovered which contained the KM50 immunoglobulin H chain promoter and enhancer genes, ApR gene, G418 resistance gene and dhfr gene cleaved with HindIII and EcoRI.

Figure 14:
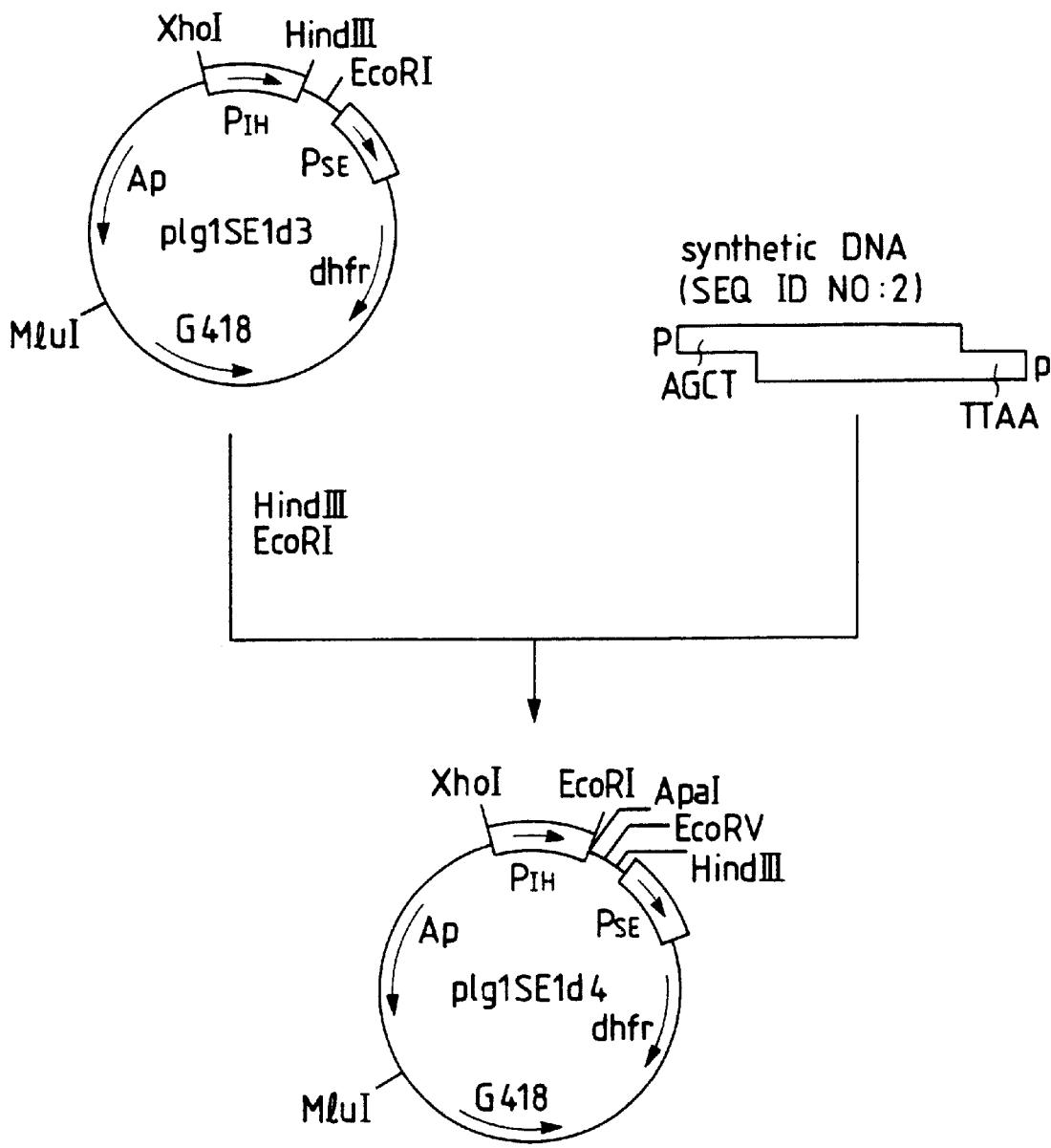
FIG. 14 shows a construction scheme for plasmid pIG1SE1d4.

Next, 0.1 μg of the thus obtained pIg1SEld3 HindIII-EcoRI fragment (about 9.2 kb) and 10 ng of the synthetic DNA (SEQ ID NO: 2) were dissolved in 20 μl of the T4 ligase buffer, and the resulting solution was mixed with 350 units of T4 DNA ligase and incubated at 4° C. for 24 hours. Using the thus obtained recombinant plasmid DNA, transformation of *E. coli* H3101 was carried out to obtain plasmid pIg1SEld4 as shown in FIG. 14.

3. Preparation of Moloney Mouse Leukemia Virus Long Terminal Repeat (To Be Referred to as "MoLTR" Hereinafter)

Since MoLTR is known to have promoter and enhancer activities (Kuwana et al., Biochem. Biophys. Res. Comun., 149, 960 (1987)), a plasmid pPMOL3 containing MoLTR was prepared in the following manner in order to use MoLTR as cassette vector promoter and enhancer.

A 3 μg portion of the plasmid pPMOL1 disclosed in JP-A 1-63394 was dissolved in 30 μl of a buffer solution containing 10 mM Tris-HCl (pH 7.5), 7 mM magnesium chloride and 6 mM 2-mercaptoethanol. The thus prepared solution was mixed with 10 units of ClaI and incubated at 37° C. for 4 hours. After subjecting the resulting reaction mixture to phenol-chloroform extraction and ethanol precipitation, the thus recovered sample was dissolved in 40 μl of the DNA polymerase I buffer solution. The resulting solution was mixed with 5 units of *E. coli* DNA polymerase I Klenow fragment and incubated at 16° C. for 2 hours to convert the cohesive 5'-end formed by the ClaI digestion into blunt end. The reaction was stopped by phenol extraction, followed by chloroform extraction and ethanol precipitation to recover 2 μg of DNA fragments. The thus precipitated DNA sample and 0.01 μg of a synthetic DNA XhoI linker (Takara Shuzo Co., Ltd.) were dissolved in 20 μl of the T4 ligase buffer, and the resulting solution was mixed with 175 units of T4 DNA ligase and incubated at 4° C. for 24 hours. Using the resulting reaction mixture, transformation of *E. coli* HB101 was carried out to obtain plasmid pPMOL2 as shown in FIG. 15. Next, a 3 μg portion of the thus obtained plasmid pPMOL2 was dissolved in 30 μl of a buffer solution containing 10 mM Tris-HCl (pH 7.5), 7 mM magnesium chloride, 10 mM sodium chloride and 6 mM 2-mercaptoethanol. The thus prepared solution was mixed with 10 units of SmaI and incubated at 37° C. for 4 hours. The resulting reaction mixture was subjected to phenol-chloroform extraction and ethanol precipitation and 2 μg of DNA fragments were recovered. The thus recovered DNA sample and 0.01 μg of a synthetic DNA EcoRI linker (Takara Shuzo Co., Ltd.) were dissolved in 20 μl of the T4 ligase buffer, and the resulting solution was mixed with 175 units of T4 DNA ligase and incubated at 4° C. for 24 hours. Using the resulting reaction mixture, transformation of *E. coli* HB101 was carried out to obtain plasmid pPMOL3 as shown in FIG. 16.

4. Cloning of H Chain Constant Region (Cgl) cDNA and L Chain Constant Region (Ck) cDNA of Human Immunoglobulin IgGl (1) Preparation of mRNA from Chimera Antibody-producing SP2-PC Chimera-1 cells Using a mRNA extraction kit, Fast Track (No. K1593-02, available from Invitrogen), 6.2 μg of mRNA was obtained from 1×10$^8$ cells of chimera antibody-producing SP2-PC Chimera-1 which has anti-phosphorylcholine activity and is disclosed in FEBS Letters (244, 301–306 (1989)).

(2) Preparation of SP2-PC Chimera-1 cDNA Library and Cloning of Human Immunoglobulin H. Chain Constant Region (Cgl) cDNA and L Chain Constant Region (Ck) cDNA A 2 μg portion of the mRNA obtained in the above step (1) was subjected to EcoRI adaptor addition using cDNA Synthesis Kit (No. 27-9260-01, available from Pharmacia) followed by kination. The resulting cDNA solution was subjected to phenol-chloroform extraction and ethanol precipitation to recover 4 μg of cDNA. The thus recovered cDNA was dissolved in 20 μl of sterile water, and the resulting solution was subjected to agarose gel electrophoresis to recover about 0.3 μg of a DNA fragment of about 1.8 kb and about 0.3 μg of a DNA fragment of about 1.0 kb.

Next, a 5 μg portion of the vector pUC18 was dissolved in 100 μl of a buffer solution containing 100 mM Tris-HCl (pH 7.5), 6 mM magnesium chloride and 100 mM sodium chloride. The thus prepared solution was mixed with 50 units of EcoRI and incubated at 37° C. for 4 hours to cleave the pUC18 DNA at its EcoRI cleavage site. The resulting reaction mixture was subjected to phenol-chloroform extraction and ethanol precipitation to recover about 3 μg of a pUC18 DNA fragment cleaved with EcoRI.

Next, 0.1 μg of the thus obtained pUC18 EcoRI fragment (about 2.7 kb) and the 1.8 kb and 1.0 kb cDNA fragments (0.1 μg for each) prepared from the SP2-PC Chimera-1 cells were dissolved in 20 μl of the T4 ligase buffer, and the resulting solution was mixed with 350 units of T4 DNA ligase and incubated at 4° C. for 24 hours.

Using the thus obtained recombinant plasmid DNA, transformation of *E. coli* LE392 was carried out. About 3,000 colonies thus obtained were fixed on nitrocellulose filters. Two $^{32}$P-labeled probes were prepared from human immunoglobulin constant region chromosomal genes (Cgl as an IgGl H chain constant region and Ck as an IgG1 L chain constant region) which have been isolated by Kameyama et al. (FEBS Letters, 244, 301 (1989)). From colonies which showed strong reactions at 65° C. with these probes, one showing strong reaction with Cg1 (pPCVHhCGI1) and the other showing strong reaction with Ck (pPCVLhCK1) were obtained.

(3) Introduction of EcoRV Site Into Human Ig k Chain Constant Region

An EcoRV site was introduced into 5'-end side of the human Ig k chain constant region by means of site-specific mutagenesis using a kit purchased from Promega (Catalogue No. Q6210). A 2 μg portion of the plasmid pPCVLhCK1 was dissolved in 30 μl of a buffer solution containing 10 mM Tris-HCl (pH 7.5), 6 mM magnesium chloride and 50 mM sodium chloride. The thus prepared solution was mixed with 10 units of EcoRI and 10 units of KpnI and incubated at 37° C. for 4 hours. The resulting reaction mixture was subjected to agarose gel electrophoresis and about 0.2 μg of a pPCV-LhCK1 DNA fragment of about 0.8 kb was recovered which contained the human immunoglobulin L chain constant region cleaved with EcoRI and KpnI.

Next, a 2 μg portion of pSELECT1 (a kit available from Promega, Catalogue No. Q6210) was dissolved in 30 μl of a buffer solution containing 10 mM Tris-HCl (pH 7.5), 6 mM magnesium chloride and 50 by sodium chloride. The thus prepared solution was mixed with 10 units of EcoRI and 10 units of KpnI and incubated at 37° C. for 4 hours. The resulting reaction mixture was subjected to agarose gel electrophoresis and about 1 μg of a pSELECT1 DNA fragment of about 5.7 kb cleaved with EcoRI and KpnI was recovered.

Figure 17:
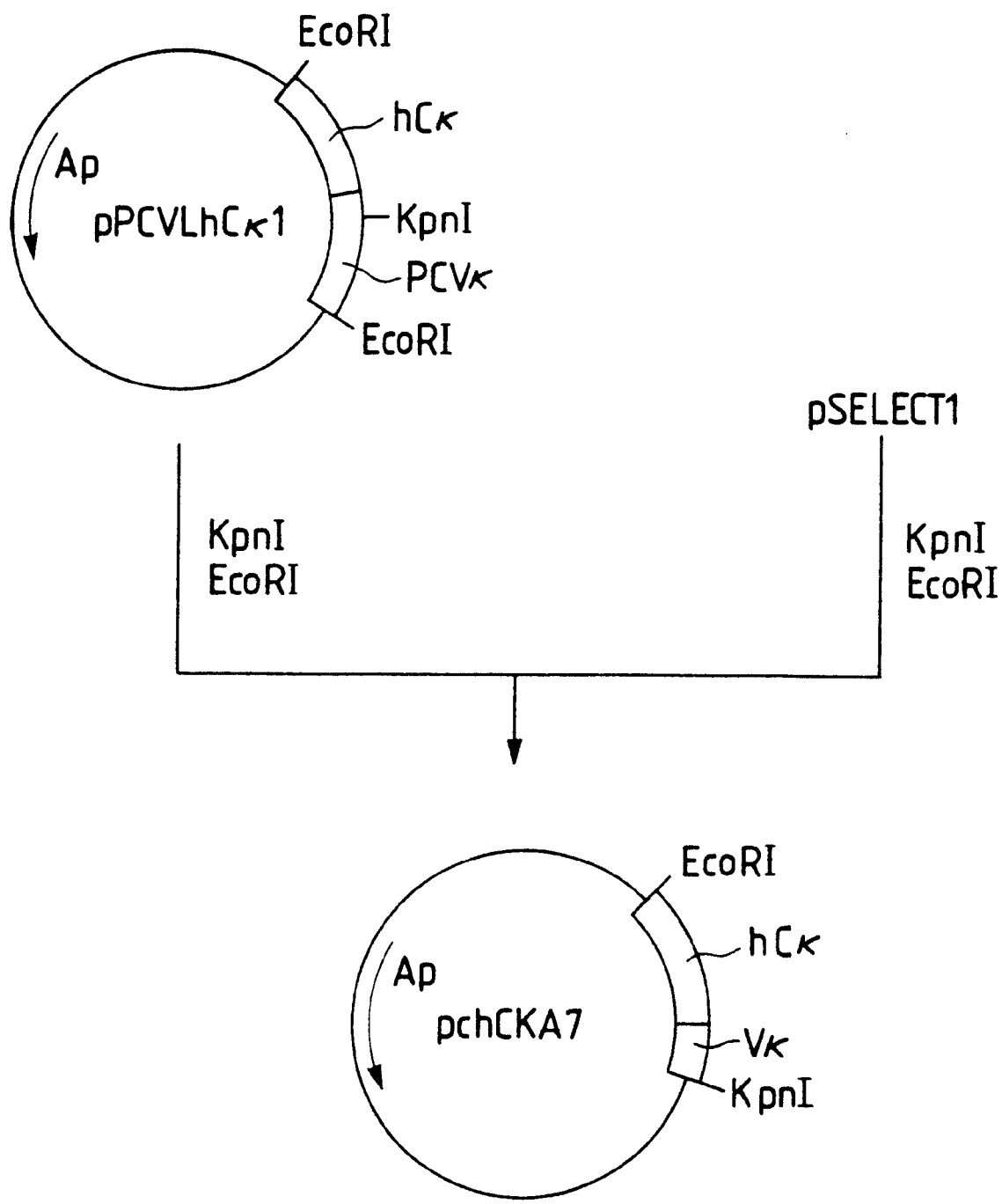
FIG. 17 shows a construction scheme for plasmid pch-CKA7.

Next, 0.1 μg of the pPCVLhCK1 EcoRI-KpnI fragment (about 0.8 kb) and 0.1 μg of the pSELECT1 EcoRI-KpnI fragment (about 5.7 kb) obtained above were dissolved in 20 μl of the T4 ligase buffer, and the resulting solution was mixed with 350 units of T4 DNA ligase and incubated at 4° C. for 24 hours. Using the thus obtained recombinant plasmid DNA, transformation of *E. coli* JM109 was carried out to obtain plasmid pchCKA7 as shown in FIG. 17.

Next, using the plasmid pchCKA7 thus obtained and the synthetic DNA of SEQ ID NO:6 as mutagenesis primer, the ACC sequence of the human immunoglobulin L chain constant region (12 to 14 position bases from the N-terminal) was converted into GAT in order to construct a plasmid pchCKB1 (FIG. 18) in which an EcoRV site was introduced into the converted site.

Next, the EcoRV site of the plasmid pchCKB1 was converted into HindIII cleavage site in the following manner. A 2 μg portion of the plasmid pchCKB1 obtained above was dissolved in 10 μl of a buffer solution containing 100 mM Tris-HCl (pH 7.5), 6 mM magnesium chloride and 100 mM sodium chloride. The thus prepared solution was mixed with 10 units of EcoRI and incubated a 37° C. for 4 hours. After subjecting the resulting reaction mixture to phenol-chloroform extraction and ethanol precipitation, the thus recovered sample was dissolved in 40 μl of the DNA polymerase I buffer solution. The resulting solution was mixed with 5 units of *E. coli* DNA polymerase I Klenow fragment and incubated at 37° C. for 30 minutes to convert the cohesive 5'-end formed by the EcoRI digestion into blunt end. The resulting reaction mixture was extracted with phenol and chloroform and then treated with ethanol. The thus precipitated sample was dissolved in 20 μl of the T4 ligase buffer containing 0.1 μg of HindIII linker (Takara Shuzo Co., Ltd.), and the resulting solution was mixed with 350 units of T4 DNA ligase and incubated at 4° C. for 24 hours. Using the thus obtained recombinant plasmid DNA, transformation of *E. coli* HB101 was carried out to obtain plasmid pchCKC1 as shown in FIG. 19.

5. Construction of Cassette Vector (1) Construction of a Cassette Vector for Use in the Construction of Humanized Chimera Antibody H Chain Expression Vector A 2 μg portion of the plasmid pIg1SEId4 obtained in the aforementioned step 2-(11) was dissolved in 30 μl of a buffer solution containing 10 mm Tris-HCl (pH 7.5), 6 mM magnesium chloride and 100 mM sodium chloride. The thus prepared solution was mixed with 10 units of EcoRV and 10 units of ApaI and incubated at 37° C. for 4 hours. The resulting reaction mixture was subjected to agar-se gel electrophoresis and about 1.5 μg of a pIg1SEId4 DNA fragment of about 9.2 kb cleaved with EcoRV and ApaI was recovered.

Next, a 2 μg portion of the plasmid pPCVHhCGI1 obtained in the aforementioned step 4-(2) was dissolved in 30 μl of a buffer solution containing 10 mM Tris-HCl (pH 7.5) and 6 mM magnesium chloride. The thus prepared solution was mixed with 10 units of ApaI and 10 units of SmaI and incubated at 37° C. for 1 hour. The resulting reaction mixture was subjeced to agarose gel electrophoresis and about 0.2 μg of a pPCVHhCGI1 DNA fragment of about 1 kb was recovered which contained the human immunoglobulin H chain constant region gene cleaved with ApaI and SmaI.

Figure 20:
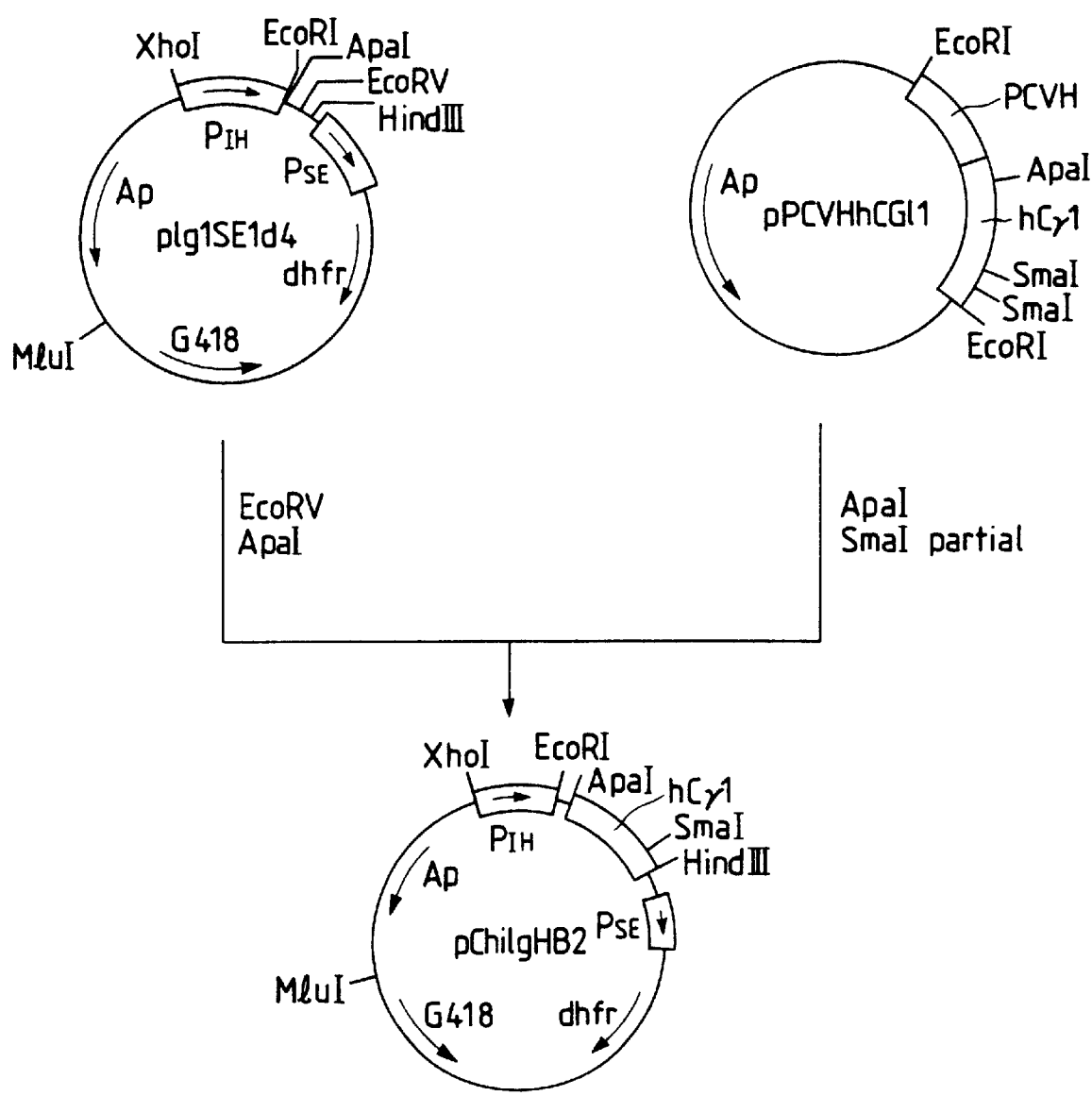
FIG. 20 shows a construction scheme for plasmid pChi-IgHB2.

Next, 0.1 μg of the pIg1SEId4 EcoRV-ApaI fragment (about 9.2 kb) and 0.1 μg of the pPCVHhCGI1 ApaI-SmaI fragment (about 1 kb) prepared above were dissolved in 20 μl of the T4 ligase buffer. The resulting solution was mixed with 350 units of T4 DNA ligase and incubated at 4° C. for 24 hours. Using the thus obtained recombinant plasmid DNA, transformation of E. coli HB101 was carried out to obtain a plasmid pChiIgHB2 (FIG. 20) as a cassette vector for use in the construction of a humanized chimera antibody H chain expression vector.

(2) Construction of a Cassette Vector for Use in the Construction of Humanized Chimera Antibody L Chain Expression Vector A 2 μg portion of the plasmid pIg1SEId4 obtained in the aforementioned step 2-(11) was dissolved in 30 μl of a buffer solution containing 10 mM Tris-HCl (pH 7.5), 6 mM magnesium chloride and 100 mM sodium chloride. The thus prepared solution was mixed with 10 units of EcoRV and 10 units of HindIII and incubated at 37° C. for 4 hours. The resulting reaction mixture was subjected to agarose gel electrophoresis and about 1.5 μg of a pIg1SEId4 DNA fragment of about 9.2 kb cleaved with EcoRV and HindIII was recovered.

Next, a 2 μg portion of the plasmid pchCKC1 obtained in the aforementioned step 4-(3) was dissolved in 30 μl of a buffer solution containing 10 mM Tris-HCl (pH 7.5), 6 mM magnesium chloride and 100 mM sodium chloride. The thus prepared solution was mixed with 10 units of EcoRV and 10 units of HindIII and incubated at 37° C. for 1 hour. The resulting reaction mixture was subjected to agarose gel electrophoresis and about 0.2 μg of a pPCVLhCK1 DNA fragment of about 0.6 kb was recovered which contained the human immunoglobulin L chain constant region gene cleaved with EcoRV and HindIII.

Figure 21:
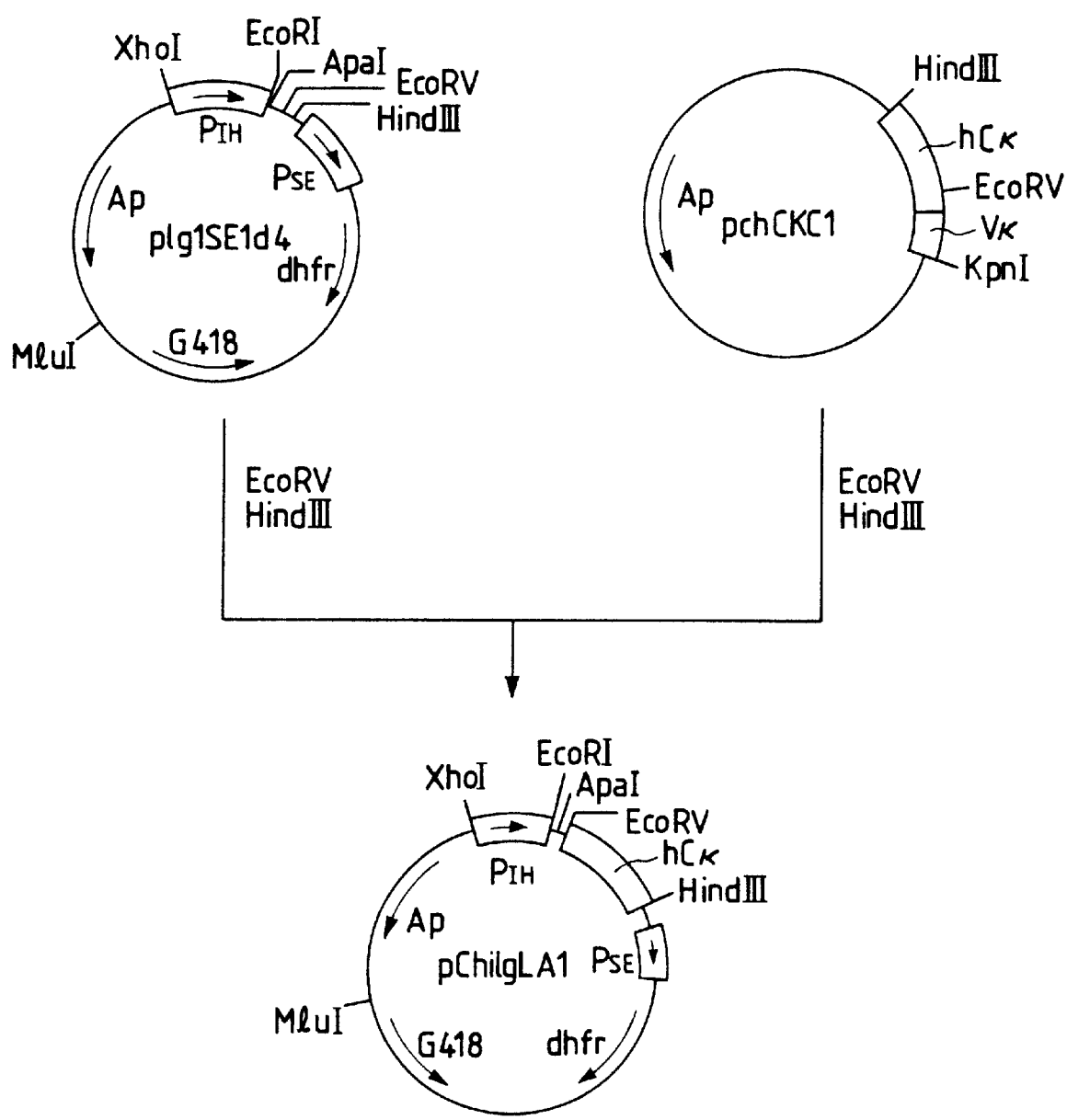
FIG. 21 shows a construction scheme for plasmid pChi-IgLA1.

Next, 0.1 μg of the pIg1SEId4 EcoRV-HindIII fragment (about 9.2 kb) and 0.1 μg of the pchCKC1 EcoRV-HindIII fragment (about 0.6 kb) prepared above were dissolved in 20 μl of the T4 ligase buffer. The resulting solution was mixed with 350 units of T4 DNA ligase and incubated at 4° C. for 24 hours. Using the thus obtained recombinant plasmid DNA, transformation of E. coli HB101 was carried out to obtain a plasmid pChiIgLA1 (FIG. 21) as a cassette vector for use in the construction of a humanized chimera antibody L chain expression vector.

EXAMPLE 2

Anti-GD$_3$ Chimera Antibody

1. Preparation of mRNA from a Hybridoma Cell Line Capable of Producing Mouse Anti-GD$_3$ Monoclonal Antibody KM-641

Using a mRNA extraction kit, Fast Track (No. K1593-02, available from Invitrogen), 34 μg of mRNA was prepared from 1×10$^8$ cells of a hybridoma cell line which is capable of producing mouse anti-GD$_3$ monoclonal antibody KM-641 prepared by the method described later in Reference Example shown below.

2. Preparation of cDNA Libraries of KM-641 H Chain and L Chain Genes

Using ZAP-cDNA Synthesis Kit (No. sc200400), a cDNA synthesis kit available from Stratagene Cloning Systems, cDNA having EcoRI adaptor on its 5'-end and XhoI adaptor on its 3'-end was prepared from 3 μg of the mRNA obtained in the above procedure 1. About 6 μg of the cDNA was dissolved in 10 μl of sterile water and subjected to agarose gel electrophoresis to recover 0.1 μg of an H chain-corresponding cDNA fragment of about 1.8 kb and 0.1 μg of an L chain-corresponding cDNA fragment of about 1.0 kb. Next, 0.1 μg of the 1.8 kb cDNA fragment, 0.1 μg of the 1.0 kb cDNA fragment and 1 μg of Uni-ZAP XR (available from Stratagene Cloning Systems; a preparation obtained by digesting Lambda ZAPII vector with EcoRI and XhoI, followed by treatment with calf intestine alkaline phosphatase) to be used as a vector were dissolved in 11.5 μl of the T4 ligase buffer, and the resulting solution was mixed with 175 units of T4 DNA ligase and incubated at 12° C. for 10 hours and then at room temperature for 2 hours. A 4 μl portion of the resulting reaction mixture was subjected to lambda phage packaging using Giga Pack Gold (Stratagene Cloning Systems) in accordance with the conventional method (Maniatis et al., Molecular Cloning, 1989, p2.95). An E. coli strain PLK-F was infected with the thus packaged product in accordance with the conventional method (Maniatis et al., Molecular Cloning, 1989, p2.95–107) to obtain an H chain cDNA library and an L chain cDNA library, each containing about 10,000 phage clones. Next, these phage particles were fixed on nitrocellulose filters in accordance with the conventional method (Maniatis et al., Molecular Cloning, 1989, p2.112).

3. Cloning of Monoclonal Antibody KM-641 H Chain and L Chain cDNA

Figure 22:
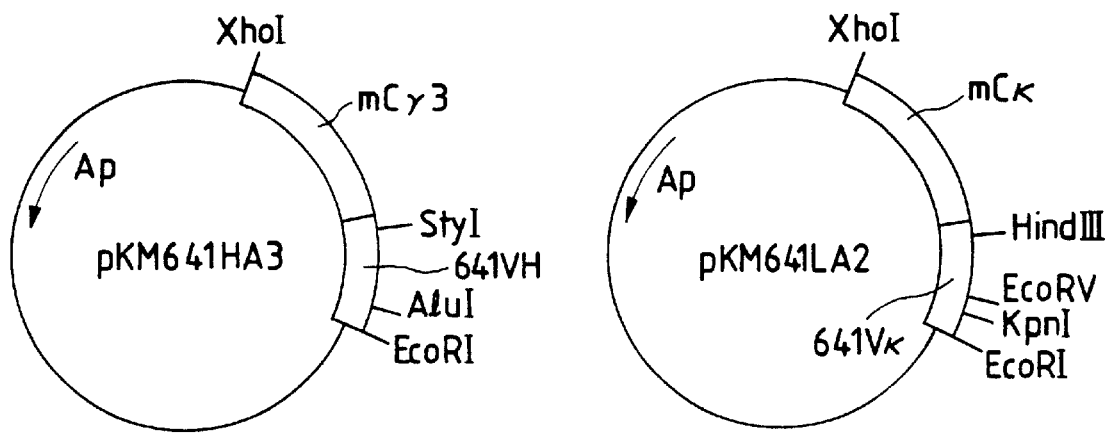
FIG. 22 shows plasmids pKM641HA3 and pKM641LA2.

Two $^{32}$P-labeled probes were prepared from an EcoRI fragment of about 6.8 kb containing a mouse immunoglobulin constant region chromosomal gene Cg1 (Roeder et al., Proc. Natl. Acad. Sci. U.S.A., 78, 474 (1981)) and a mouse Ck gene-containing HindIII-BamHI fragment of about 3 kb (Sakano et al., Nature, 280, 288 (1979)). A phage clone which showed strong reaction at 65° C. with one of these two probes were obtained from each of the H chain cDNA library and the L chain cDNA library prepared in the above procedure 2 in accordance with the conventional method (Maniatis et al., Molecular Cloning, 1989, p2.108). Next, using ZAP-cDNA Synthesis Kit (No. sc200400), a cDNA synthesis kit of Stratagene Cloning Systems each of the thus obtained phage clones was introduced into plasmid pBluescript to isolate a recombinant plasmid pKM641HA3 containing the KM-641 H chain cDNA and a recombinant plasmid pKM641LA2 containing the KM-641 L chain cDNA. When each of the plasmids pKM641HA3 and pKM641LA2 was digested with EcoRI and XhoI, it was found that cDNA of about 1.6 kb had been inserted into the former plasmid, and cDNA of about 0.9 kb into the latter (FIG. 22).

4. Immunoglobulin Variable Region Base Sequences of KM-641 H Chain cDNA (pKM641HA3) and KM-641 L Chain cDNA (pKM641LA2)

Immunoglobulin variable region base sequences of the plasmids pKM641HA3 and pM641LA2 obtained in the above procedure 3 were determined by the dideoxy method (Maniatis et al., Molecular Cloning, 1989, p13.42) using Sequenase Version 2.0 DNA Sequencing Kit (United States Biochemical Corporation). The results are shown in SEQ ID NO:7 and SEQ ID NO:9. The plasmid pKM641LA2 was a complete cDNA containing a leader sequence and having a methionine-corresponding sequence which was assumed to be the initiation codon ATG located close to the 5'-end. The plasmid pKM641HA3, on the other hand, did not have such a methionine-corresponding initiation codon-like sequence on its 5'-end side, and its leader sequence was partially deficient.

5. Construction of KM-641 Chimera H Chain Expression Vector

Figure 23:
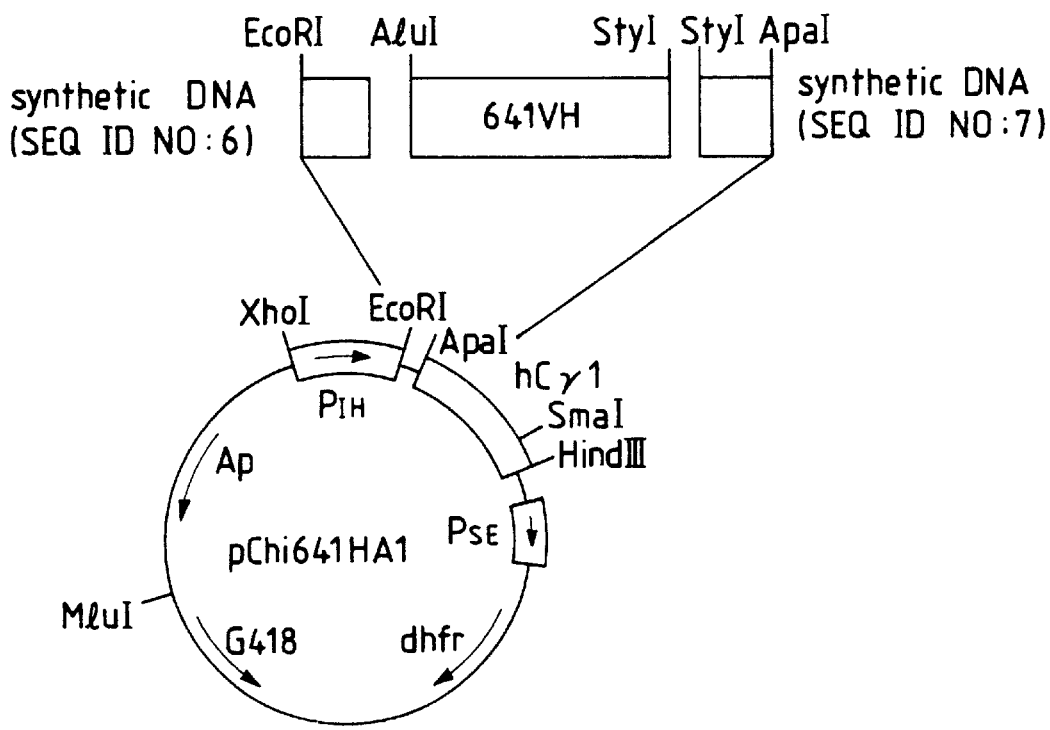
FIG. 23 shows plasmid pChi641HA1.

H chain variable region gene obtained by cleaving the plasmid pKM641HA3 variable region at the 5'-end AluI site and 3'-end StyI site was ligated with the cassette vector for use in the construction of the humanized chimera antibody H chain obtained in Example 1 using the synthetic DNA sequences shown in SEQ ID NO:11 and SEQ ID NO:13, thereby constructing a humanized chimera antibody H chain expression vector pchi641HA1 (FIG. 23).

Firstly, the DNA shown in SEQ ID NO:13 (see FIG. 23) was synthesized using a DNA synthesizer. This synthetic DNA comprises a base sequence derived from plasmid pKM641HA3 ranging from the 3'-end of its immunoglobulin H chain variable region to a StyI cleavage site in the vicinity of the 3'-end and a base sequence derived from plasmid pAGE28 ranging from the 5'-end of its immunoglobulin H chain constant region to an ApaI cleavage site in the vicinity of the 5'-end. Thus, the synthetic DNA has a StyI cleavage site and an ApaI cleavage site on both of its end. Next, the thus synthesized DNA was introduced into the plasmid pKM641HA3 in the following manner.

Figure 24:
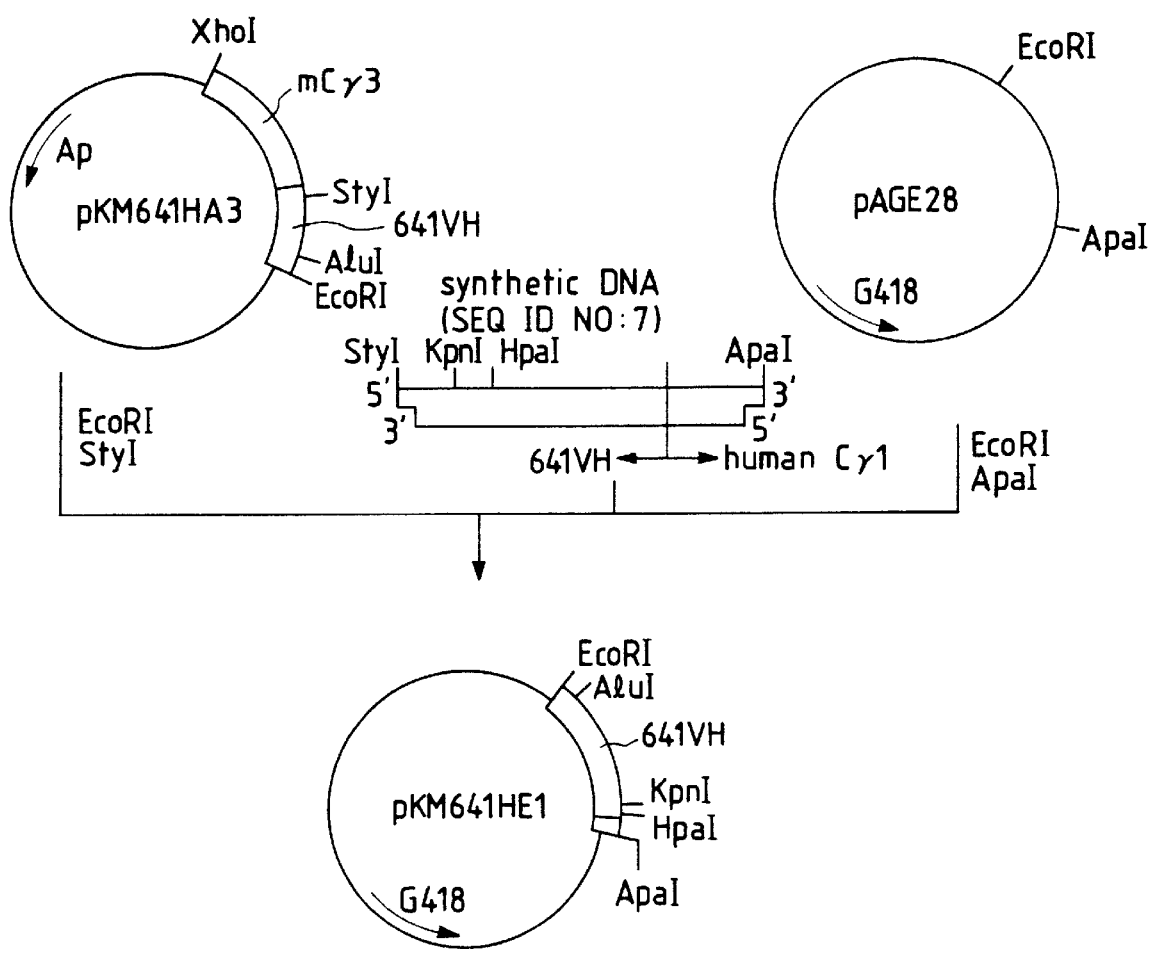
FIG. 24 shows a construction scheme for plasmid pKM641HE1.

A 3 µg portion of the plasmid pKM641HA3 was dissolved in 30 µl of a buffer solution containing 50 mM Tris-HCl (pH 7.5), 10 mM magnesium chloride, 50 mM sodium chloride and 1 mM DTT. The thus prepared solution was mixed with 10 units of EcoRI and 10 units of StyI and incubated at 37° C. for 4 hours. The resulting reaction mixture was subjected to agarose gel electrophoresis and about 0.3 µg of a DNA fragment of about 0.41 kb was recovered. Next, a 3 µg portion of pAGE28 (Mizukami et al., J. Biochem., 101, 1307–1310 (1987)) was dissolved in 30 µl of a buffer solution containing 10 mM Tris-HCl (pH 7.5), 7 mM magnesium chloride and 6 mM 2-mercaptoethanol. The thus prepared solution was mixed with 10 units of EcoRI and 10 units of ApaI and incubated at 37° C. for 4 hours. The resulting reaction mixture was subjected to agarose gel electrophoresis and about 2 µg of a DNA fragment of about 2.45 kb was recovered. Next, 0.1 µg of the pKM641HA3 EcoRI-StyI fragment (about 0.41 kb) and 0.1 µg of the pAGE28 EcoRI-ApaI fragment (about 2.45 kb) prepared above and 0.3 µg of the synthetic DNA of SEQ ID NO:13 were dissolved in 20 µl of the T4 ligase buffer solution. The resulting solution was mixed with 350 units of T4 DNA ligase and incubated at 4° C. for 24 hours. Using the thus obtained recombinant plasmid DNA, transformation of E. coli HB101 was carried out to obtain a plasmid pKM641HE1 as shown in FIG. 24.

Since the thus constructed plasmid pKM641HE1 lacks a leader sequence, the following attempt was made to supplement the plasmid with the leader sequence using the synthetic DNA of SEQ ID NO:11.

A 3 µg portion of the plasmid pKM641HE1 was dissolved in 30 µl of a buffer solution containing 10 mM Tris-HCl (pH 7.5), 7 mM magnesium chloride and 6 mM 2-mercaptoethanol. The thus prepared solution was mixed with 10 units of EcoRI and 10 units of ApaI and incubated at 37° C. for 4 hours. The resulting reaction mixture was subjected to agarose gel electrophoresis and about 0.4 µg of a DNA fragment of about 0.42 kb was recovered. Next, a 0.4 µg portion of the thus prepared pKM641HE1 EcoRI-ApaI fragment (about 0.42 kb) was dissolved in 30 µl of a buffer solution containing 10 mM Tris-HCl (pH 7.5), 7 mM magnesium chloride, 50 mM sodium chloride and 6 mM 2-mercaptoethanol. The thus prepared solution was mixed with 10 units of AluI and incubated at 37° C. for 4 hours. The resulting reaction mixture was subjected to phenol-chloroform extraction and ethanol precipitation and about 0.3 µg of a DNA fragment of about 0.4 kb was recovered.

Figure 25:
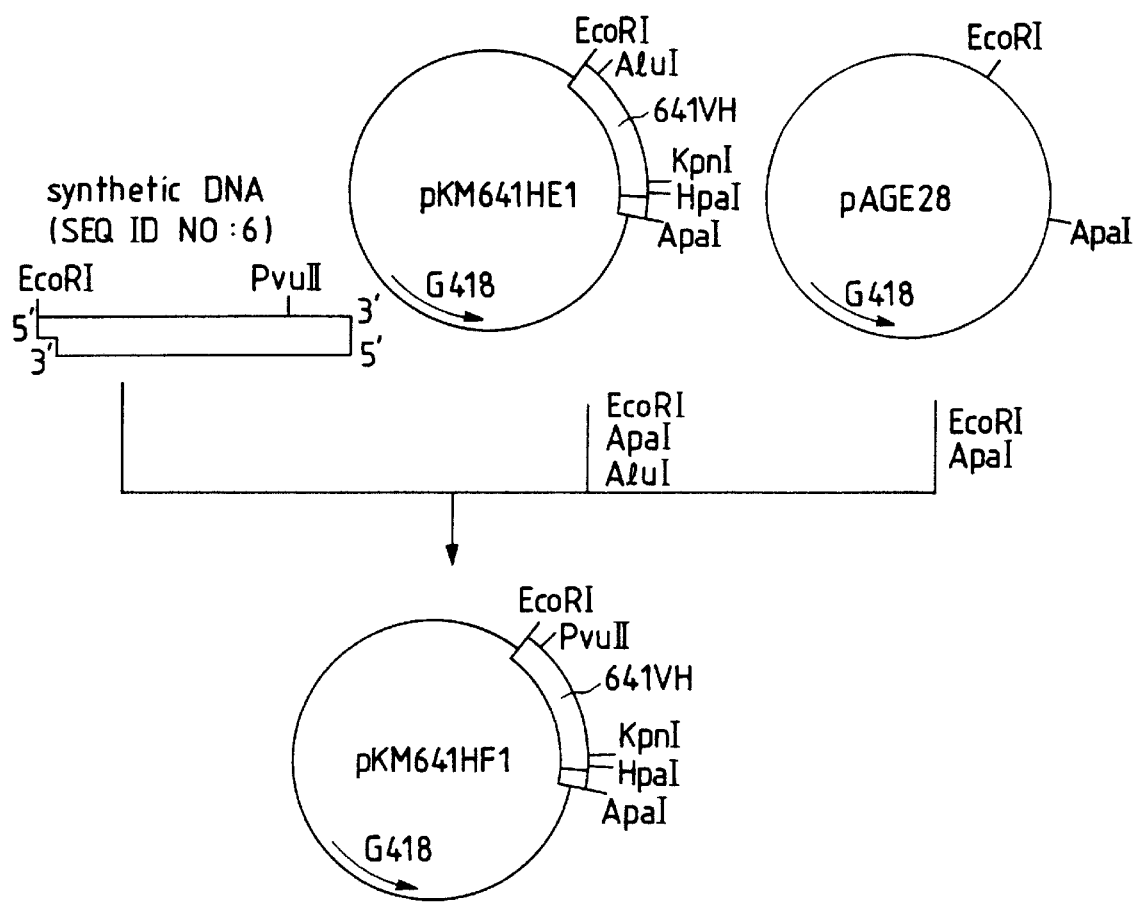
FIG. 25 shows a construction scheme for plasmid pKM641HF1.

Next, 0.1 µg of the pKM641HE1 AluI-ApaI fragment (about 0.4 kb) and 0.1 µg of the pAGE28 EcoRI-ApaI fragment (about 2.45 kb) prepared above and 0.3 µg of the synthetic DNA of SEQ ID NO:11 were dissolved in 20 µl of the T4 ligase buffer solution. The resulting solution was mixed with 350 units of T4 DNA ligase and incubated at 4° C. for 24 hours. Using the thus obtained recombinant plasmid DNA, transformation of E. coli HB101 was carried out to obtain a plasmid pKM641HF1 as shown in FIG. 25.

Next, immunoglobulin H chain variable region of the thus obtained plasmid pKM641HF1 was introduced into the aforementioned cassette vector pChiIgHB2 in the following manner.

Figure 26:
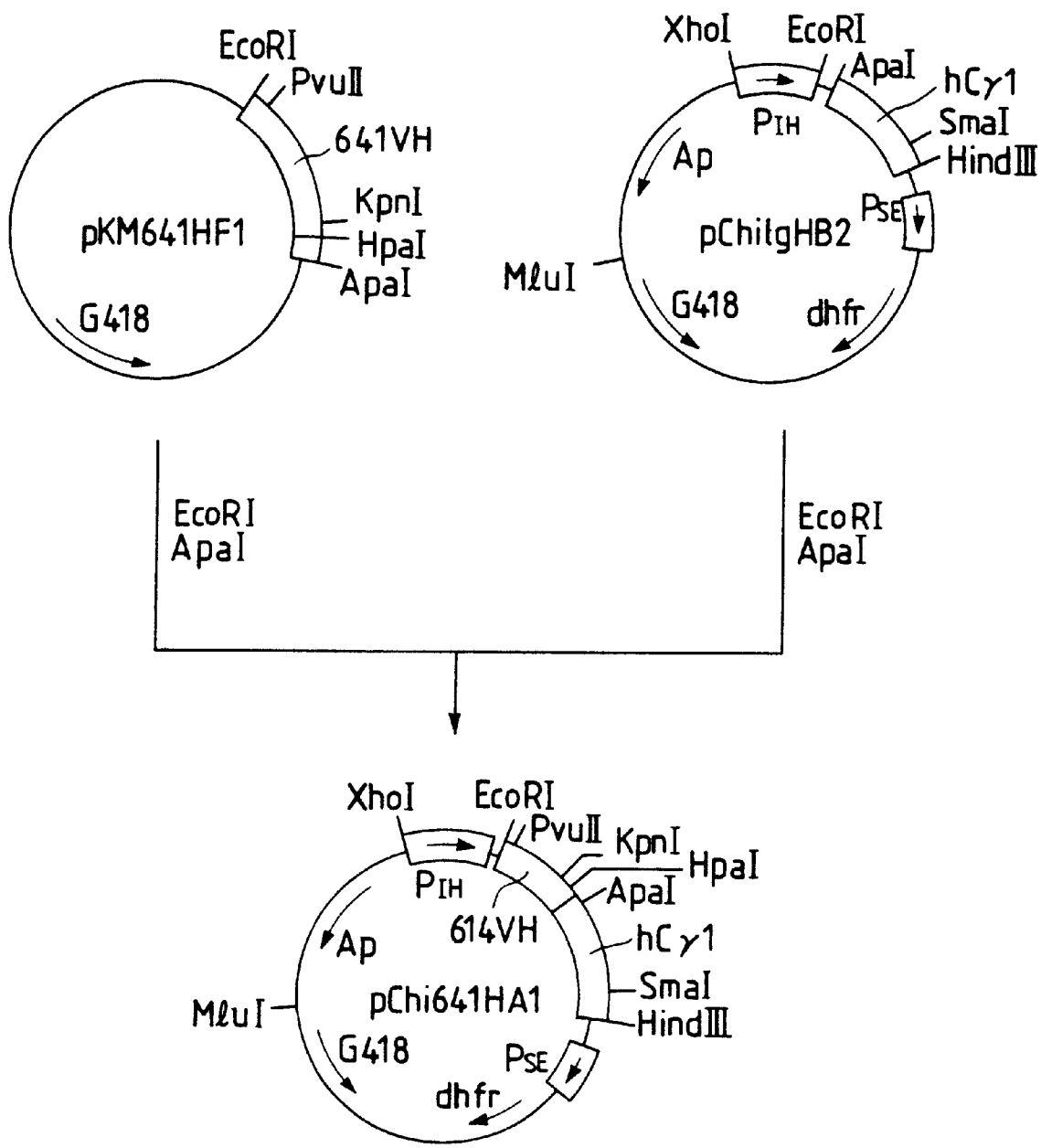
FIG. 26 shows a construction scheme for plasmid pChi641HA1.

A 3 µg portion of the plasmid pKM641HF1 was dissolved in 30 µl of a buffer solution containing 10 mM Tris-HCl (pH 7.5), 7 mM magnesium chloride and 6 mM 2-mercaptoethanol. The thus prepared solution was mixed with 10 units of EcoRI and 10 units of ApaI and incubated at 37° C. for 4 hours. The resulting reaction mixture was subjected to agarose gel electrophoresis and about 0.5 µg of a DNA fragment of about 0.44 kb was recovered. Next, a 3 µg portion of the pChiIgHB2 was dissolved in 30 µl of a buffer solution containing 10 mM Tris-HCl (pH 7.5), 7 mM magnesium chloride and 6 mM 2-mercaptoethanol. The thus prepared solution was mixed with 10 units of EcoRI and 10 units of ApaI and incubated at 37° C. for 4 hours. The resulting reaction mixture was subjected to phenol-chloroform extraction and ethanol precipitation and about 3 µg of DNA was recovered. Next, 0.1 µg of the pKM641HF1 EcoRI-ApaI fragment (about 0.44 kb) and 0.1 µg of the pChiIgHB2 EcoRI-ApaI fragment (about 10.1 kb) prepared above were dissolved in 20 µl of the T4 ligase buffer. The resulting solution was mixed with 350 units of T4 DNA ligase and incubated at 4° C. for 24 hours. Using the thus obtained recombinant plasmid DNA, transformation of E. coli HB101 was carried out to obtain a plasmid pChi641HA1 as shown in FIG. 26.

Next, KM50-derived immunoglobulin H chain promoter and enhancer regions of the thus obtained plasmid pChi641HA1 were converted into MoLTR in the following manner.

Figure 27:
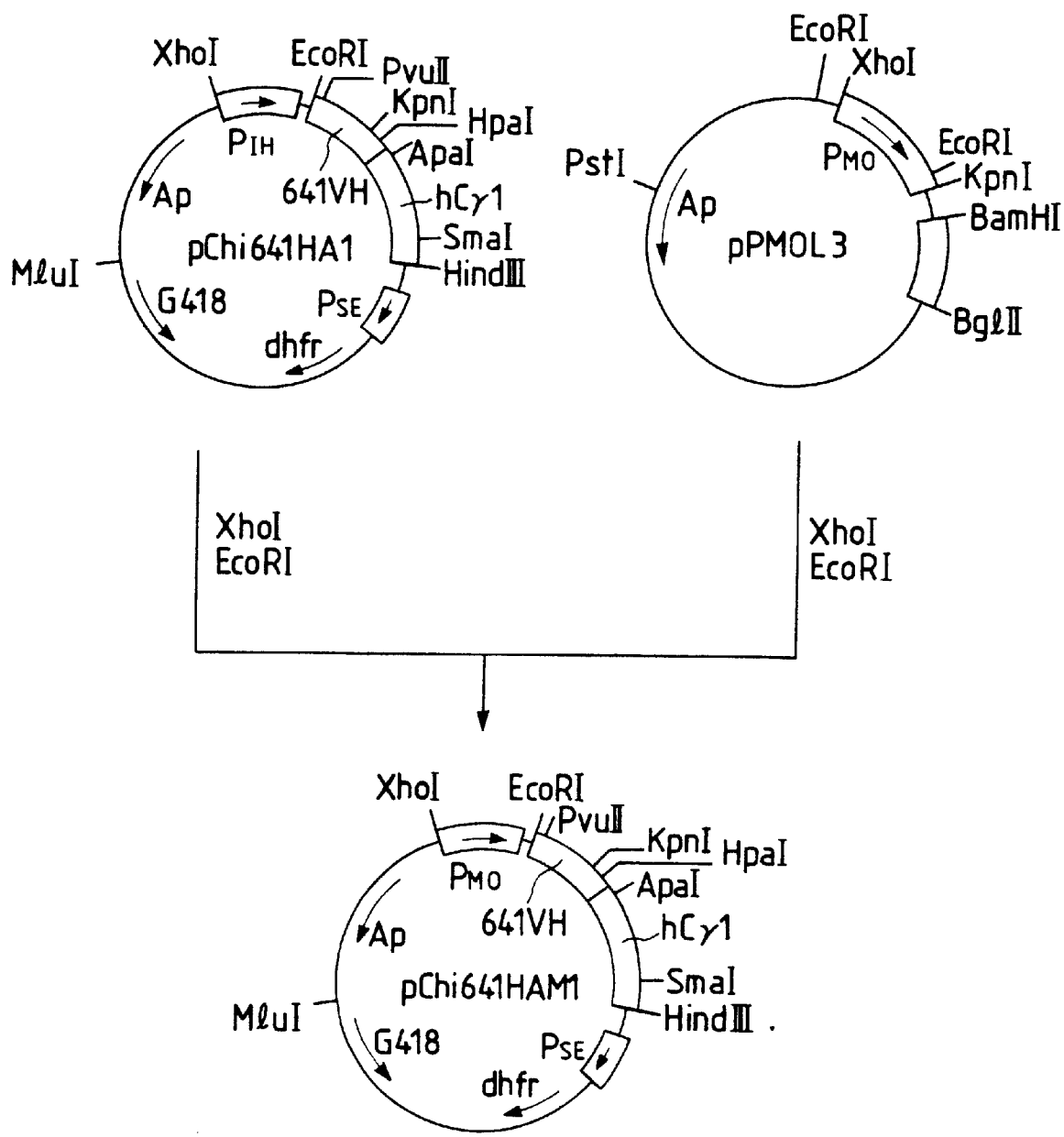
FIG. 27 shows a construction scheme for plasmid pChi641HAM1.

A 3 µg portion of the plasmid pChi641HA1 was dissolved in 30 µl of a buffer solution containing 50 mM Tris-HCl (pH 7.5), 10 mM magnesium chloride, 50 mM sodium chloride and 1 mM DTT. The thus prepared solution was mixed with 10 units of EcoRI and 10 units of XhoI and incubated at 37° C. for 4 hours. The resulting reaction mixture was subjected to agarose gel electrophoresis and about 0.2 µg of a DNA fragment of about 8.8 kb was recovered. Next, a 3 µg portion of the pPMOL3 prepared in procedure 2 of Example 1 was dissolved in 30 µl of a buffer solution containing 50 mM Tris-HCl (pH 7.5), 10 mM magnesium chloride, 50 mM sodium chloride and 1 mM DTT. The thus prepared solution was mixed with 10 units of EcoRI and 10 units of XhoI and incubated at 37° C. for 4 hours. The resulting reaction mixture was subjected to agarose gel electrophoresis and about 0.3 μg of a DNA fragment of about 0.63 kb containing MoLTR was recovered. Next, 0.1 μg of the pChi641HA1 EcoRI-XhoI fragment and 0.1 μg of the pPMOL3 EcoRI-XhoI fragment prepared above were dissolved in 20 μl of the T4 ligase buffer solution. The resulting solution was mixed with 175 units of T4 DNA ligase and incubated at 4° C. for 24 hours. Using the resulting reaction mixture, transformation of E. coli HB101 was carried out to obtain a plasmid pChi641HAM1 (FIG. 27) as a KM-641 chimera H chain expression vector.

6. Construction of RM-641 Chimera L Chain Expression Vector

Figure 28:
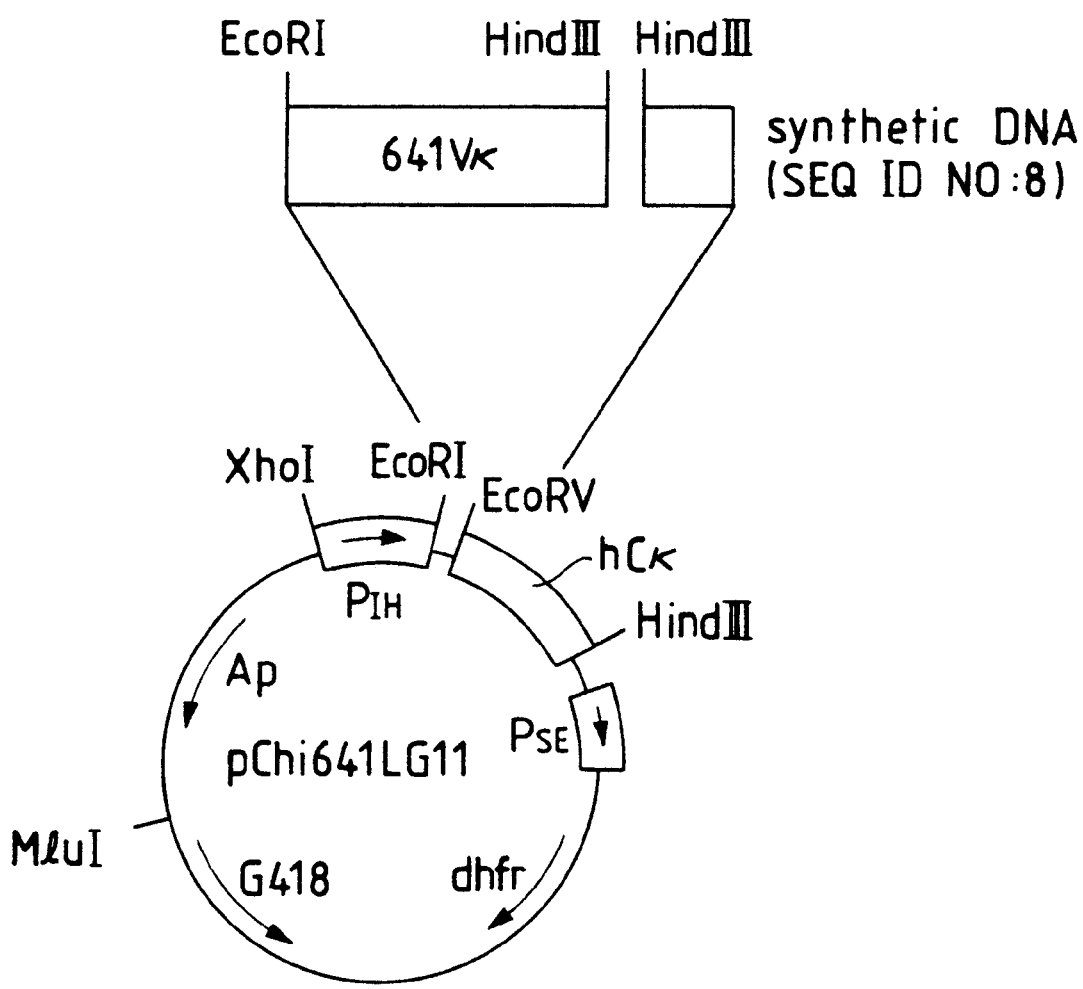
FIG. 28 shows plasmid pChi641LG11.

L chain variable region gene obtained by cleaving the plasmid pKM641LA2 variable region gene at its 5'-end EcoRI site and 3'-end HindIII site was ligated with the cassette vector for the expression of chimera L chain, using the synthetic DNA shown in SEQ ID NO: 15, thereby constructing an L chain expression vector pchi641LG11 (FIG. 28).

Firstly, the DNA of SEQ ID NO: 8 (see FIG. 29) was synthesized using a DNA synthesizer. This synthetic DNA comprises a base sequence corresponding to a region of the plasmid pKM641LA2 ranging from the 3'-end of the immunoglobulin L chain variable region to a HindIII cleavage site in the vicinity of the 3'-end and a base sequence corresponding to a region of the plasmid pChiIgLA1 ranging from the 5'-end to an EcoRV cleavage site in the vicinity of the 5'-end. Thus, it has a HindIII cleavage site and an EcoRV cleavage site on both ends. Next, the thus synthesized DNA was introduced into the plasmid pKM641LA2 in the following manner.

Figure 29:
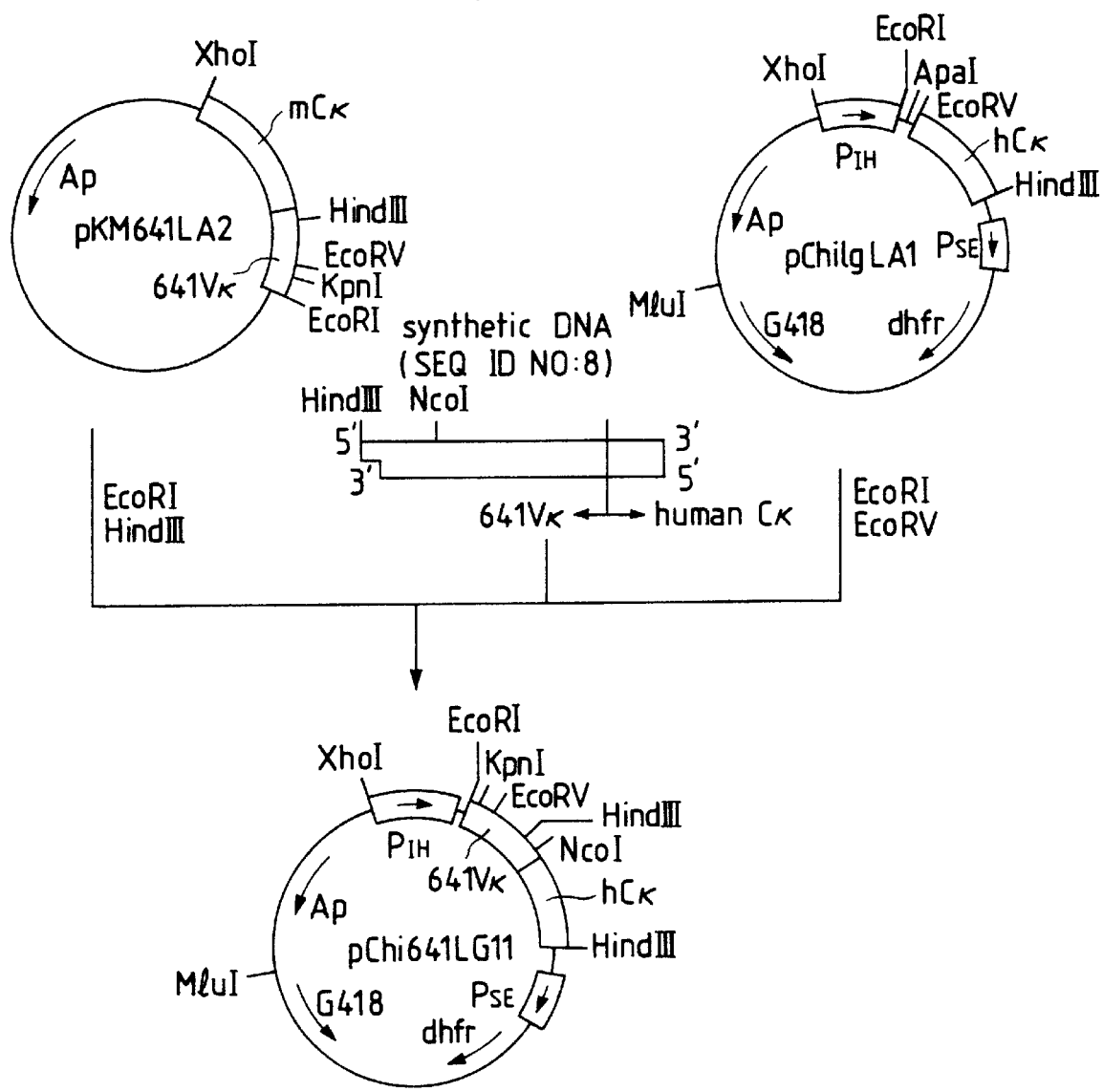
FIG. 29 shows a construction scheme for plasmid pChi641LG11.

A 3 μg portion of the plasmid pKM641LA2 was dissolved in 30 μl of a buffer solution containing 10 mM Tris-HCl (pH 7.5), 7 mM magnesium chloride, 50 mM sodium chloride and 6 mM 2-mercaptoethanol. The thus prepared solution was mixed with 10 units of EcoRI and 10 units of HindIII and incubated at 37° C. for 4 hours. The resulting reaction mixture was subjected to agarose gel electrophoresis and about 0.3 μg of a DNA fragment of about 0.35 kb was recovered. Next, a 3 μg portion of pChiIgLA1 was dissolved in 30 μl of a buffer solution containing 50 mM Tris-HCl (pH 7.5), 10 mM magnesium chloride, 50 mM sodium chloride and 1 mM DTT. The thus prepared solution was mixed with 10 units of EcoRI and 10 units of EcoRV and incubated at 37° C. for 4 hours. The resulting reaction mixture was subjected to phenol-chloroform extraction and ethanol precipitation and about 3 μg of DNA was recovered and dissolved in 10 μl of the TE solution (a buffer solution containing 10 mM Tris-HCl and 1 mM EDTA (pH 7.5)). Next, 0.1 μg of the pKM641LA2 EcoRI-HindIII fragment (about 0.35 kb) and 0.1 μg of the pChiIgLA1 EcoRI-EcoRV fragment (about 9.7 kb) prepared above and 0.3 μg of the synthetic DNA of SEQ ID NO:15 were dissolved in 20 μl of the T4 ligase buffer solution. The resulting solution was mixed with 350 units of T4 DNA ligase and incubated at 4° C. for 24 hours. Using the thus obtained recombinant plasmid DNA, transformation of E. coli HB101 was carried out to obtain a plasmid pChi641LG11 as shown in FIG. 29.

Next, KM50-derived immunoglobulin H chain promoter and enhancer regions of the thus obtained plasmid pChi641LG11 were converted into MoLTR in the following manner.

Figure 30:
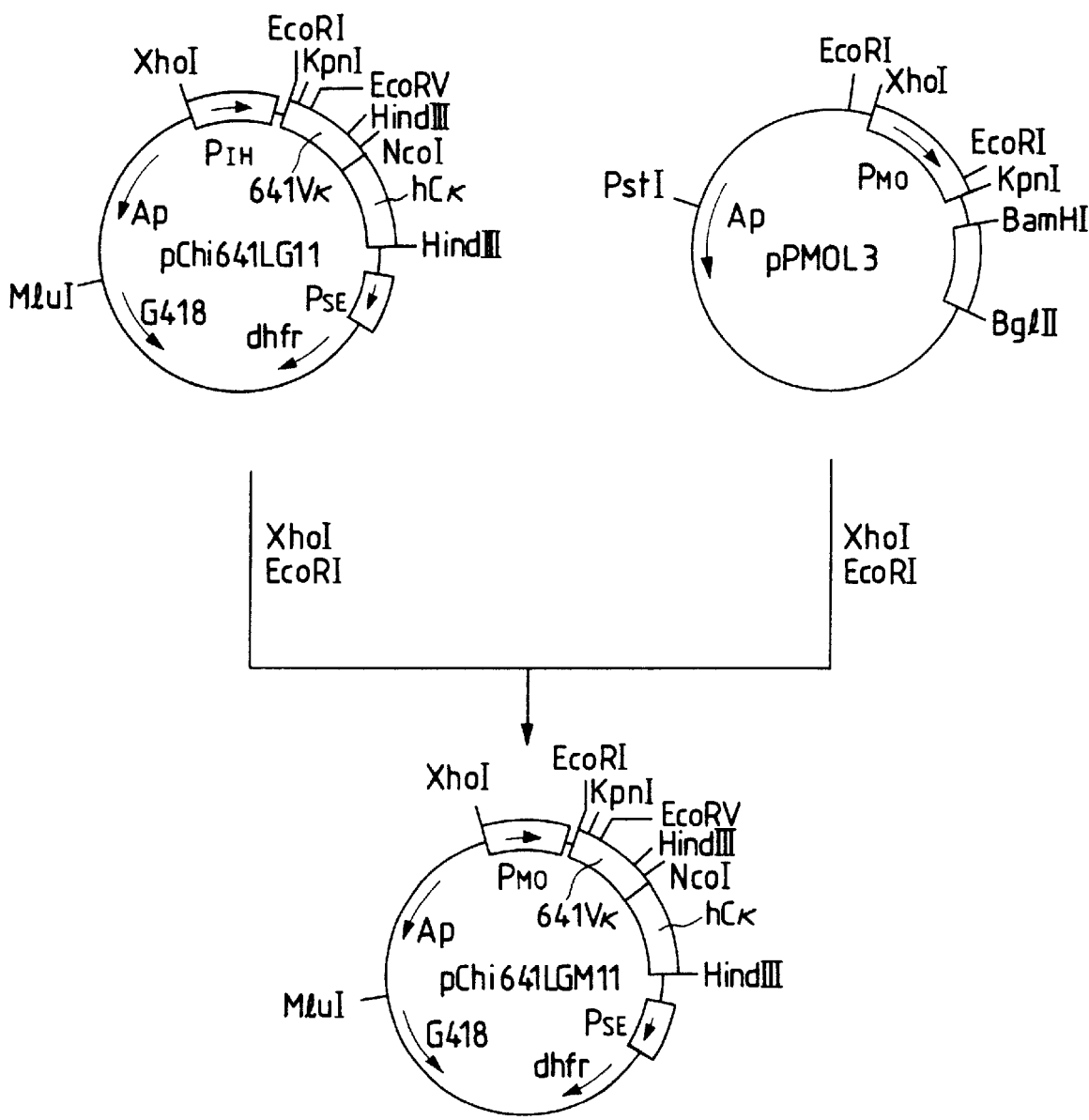
FIG. 30 shows a construction scheme for plasmid pChi641LGM11.

A 3 μg portion of the plasmid pChi641LG11 was dissolved in 30 μl of a buffer solution containing 50 mM Tris-HCl (pH 7.5), 10 mM magnesium chloride, 50 mM sodium chloride and 1 mM DTT. The thus prepared solution was mixed with 10 units of EcoRI and 10 units of XhoI and incubated at 37° C. for 4 hours. The resulting reaction mixture was subjected to agarose gel electrophoresis and about 0.2 μg of a DNA fragment of about 8.3 kb was recovered. Next, 0.1 μg of the pChi641LG11 EcoRI-XhoI fragment and 0.1 μg of the pPMOL3 EcoRI-XhoI fragment prepared above were dissolved in 20 μl of the T4 ligase buffer. The resulting solution was mixed with 175 units of T4 DNA ligase and incubated at 4° C. for 24 hours. Using the resulting reaction mixture, transformation of E. coli HB101 was carried out to obtain a plasmid pChi641LGM11 (FIG. 30) as a KM-641 chimera L chain expression vector.

7. Expression of Anti-GD3 Chimera Antibody in SP2/0 Cells

Introduction of plasmid into SP2/0 cells was carried out making use of the electroporation technique in accordance with the method of Miyaji et al. (Cytotechnology, 3, 133–140 (1990)).

The plasmids pChi641LG11 and pChi641HA1 (2 μg for each), or the plasmids pChi641LGM11 and pChi641HAM1 (2 μg for each), were simultaneously introduced into $2 \times 10^6$ of SP2/0 cells, and the resulting cells were suspended in 40 ml of RPMI1640-FCS(10) which has been prepared by supplementing RPMI1640 medium (Nissui Pharmaceutical Co., Ltd.) with 10% of FCS, ¹⁄₄₀ volume of 7.5% $NaHCO_3$, 3% of 200 mM L-glutamine solution (available from GIBCO) and 0.5% of a penicillin-streptomycin solution (GIBCO, a solution containing 5,000 units/ml of penicillin and 5,000 units/ml of streptomycin). The thus prepared cell suspension was distributed in 200 μl-portions into wells of a 96-well microtiter plate (Flow Laboratories), and the cells were cultured at 37° C. in a $CO_2$ incubator. After 24 hours of the culturing, G418 (GIBCO) was added to the cell suspension to a final concentration of 0.5 mg/ml, and the culturing was continued for 1 to 2 weeks. When transformant colonies were developed and grown into confluent stages, culture broths were recovered from the wells to measure anti-$GD_3$ chimera antibody activities by ELISA method in the following manner.

<Enzyme Immunoassay (ELISA)>

A 2 ng portion of $GD_3$ (available from Iatron) or other type of ganglioside was dissolved in 2 μl of ethanol solution containing 5 ng of phosphatidylcholine (Sigma Chemical Co.) and 2.5 ng of cholesterol (Sigma Chemical Co.). A 20 μl portion of the thus prepared solution or the same volume of its dilution solution was distributed into each well of a 96-well microtiter plate (available from Greiner). After air-drying, blocking was effected with PBS containing 1% BSA. To each well was added 50 to 100 μl of a culture supernatant of a transformant, a purified mouse monoclonal antibody solution or a purified chimera antibody solution. After reaction at 4° C. for 10 hours, each well was washed with PBS and charged with 50 to 100 μl of peroxidase-labeled protein A (Funakoshi Pharmaceutical Co., Ltd.), followed by 1 to 2 hours of reaction at room temperature. After washing with PBS, 50 to 100 μl of ABTS substrate solution prepared by dissolving 550 mg of diammonium 2,2'-azinobis(3-ethylbenzothiazoline-6-sulfonate) in 0.1 M citrate buffer (pH 4.2) and adding 1 μl/ml of hydrogen peroxide to the resulting solution just before its use was added to each well to develop color, and $OD_{415}$ of the reaction mixture was measured.

Among clones Anus obtained, culture broth of a clone having the highest activity measured by ELISA method contained anti-$GD_3$ chimera antibody in an amount of about 0.1 μg/ml.

The clone having anti-GD$_3$ chimera antibody activity was suspended in the aforementioned RPMI1640-FCS(10) medium supplemented with 0.5 mg/ml of G418 and 50 nM of methotrexate (to be referred to as "MTX" hereinafter) to a final cell density of 1–2×10$^5$ cells/ml. The thus prepared cell suspension was distributed in 2-ml portions into wells of a 24 well plate, and the cells were cultured at 37° C. for 2 to 3 weeks in a CO$_2$ incubator to induce clones resistant to 50 nM MTX. When the thus induced clones were grown into confluent stages, anti-GD$_3$ chimera antibody activities in the culture broths were measured by the ELISA method. Among clones thus obtained, culture broth of a 50 nM MTX-resistant clone having the highest activity measured by ELISA method contained anti-GD$_3$ chimera antibody in an amount of about 0.3 μg/ml.

The 50 nM MTX-resistant clone was suspended in the RPMI1640-FCS(10) medium supplemented with 0.5 mg/ml of G418 and 200 nM of MTX to a final cell density of 1–2×10$^5$ cells/ml. The thus prepared cell suspension was distributed in 2-m portions into wells of a 24 well plate, and the cells were cultured at 37° C. for 2 to 3 weeks in a CO$_2$ incubator to induce clones resistant to 200 nM MTX. When the thus induced clones were grown into confluent stages, anti-GD$_3$ chimera antibody activities in the culture broths were measured by the ELISA method. Among clones thus obtained, culture broth of a 200 nM MTX-resistant clone having the highest activity measured by ELISA method contained anti-GD$_3$ chimera antibody in an amount of about 2 μg/ml. This 200 nM MTX-resistant clone was named transformant KM-871.

Expression of anti-GD$_3$ chimera antibody protein in the transformant KM-871 was confirmed by SDS-polyacrylamide gel electrophoresis (SDS-PAG) in the following manner.

The transformant KM-871 was suspended in GIT medium (Nihon Seiyaku Co., Ltd.) supplemented with 0.5 mg/ml of G418 and 200 nM of MTX to a final cell density of 1–2×10$^5$ cells/ml. The thus prepared cell suspension was distributed in 100-ml portions in 175 cm$^2$ flasks (available from Greiner), and the cells were cultured at 37° C. for 3 to 5 days in a CO$_2$ incubator. When the cells were grown into confluent stage, the resulting culture broth (about 900 ml) was recovered and subjected to salting-out with 50% ammonium sulfate. Using Affigel Protein A MAPS-II Kit (Bio-Rad Laboratories), about 100 μg of purified anti-GD$_3$ chimera antibody KM-871 was obtained. About 5 μg of the thus purified anti-GD$_3$ chimera antibody KM-871 was subjected to electrophoresis in accordance with the conventional method (Laemmli, Nature, 227, 680 (1970)) to check its molecular weigh. The results are shown in FIG. 31. As shown in the figure, under reductive conditions, molecular weights of the chimera H chain and the chimera L chain were found to be about 50 kilodaltons and about 25 kilodaltons, respectively, thus confirming expression of the H and L chains having correct molecular weights. Under non-reductive conditions, molecular weight of the chimera antibody was found to be about 150 kilodaltons which confirmed expression of the correct size antibody consisting of two H chains and two L chains.

8. Reaction Specificity of Anti-GD$_3$ Chimera Antibody KM-871

Reactivities of the anti-GD$_3$ chimera antibody with ganglioside GM$_1$, N-acetyl GM$_2$ (Boehringer-Mannheim Corp.), N-glycolyl GM$_2$, N-acetyl GM$_3$, N-glycolyl GM$_3$, GD$_{1a}$, GD$_{1b}$ (Iatron), GD$_2$, GD$_3$ (Iatron), GT$_{1b}$ (Funakoshi Pharmaceutical Co., Ltd.) and GQ$_{1b}$ (Iatron) were measured by the ELISA method. In this instance, GM$_1$ and GD$_{1a}$ were purified from bovine brain, N-glycolyl GM$_2$ and N-glycolyl GM$_3$ from mouse liver, N-acetyl GM$_3$ from dog erythrocytes and GD$_2$ from a cultured cell line IMR32 (ATCC CCL127), in accordance with the conventional method (J. Biol. Chem., 263, 10915 (1988)). The results are shown in Table 1.

TABLE 1

| | Binding activity of antibody (OD$_{415}$) | |
|---|---|---|
| Ganglioside | Anti-GD$_3$ chimera antibody (0.3 μg/ml) | Mouse anti-GD$_3$ antibody (0.4 μg/ml) |
| N-acetyl GM$_3$ | 0.007 | 0.006 |
| N-glycolyl GM$_3$ | 0 | 0 |
| N-acetyl GM$_2$ | 0 | 0 |
| N-glycolyl GM$_2$ | 0 | 0 |
| GM$_1$ | 0 | 0 |
| GD$_2$ | 0 | 0 |
| GD$_3$ | 0.717 | 1.33 |
| GD$_{1a}$ | 0 | 0 |
| GD$_{1b}$ | 0 | 0 |
| GT$_{1b}$ | 0 | 0 |
| GQ$_{1b}$ | 0 | 0.16 |

As shown in Table 1, anti-GD$_3$ chimera antibody KM-871 and mouse anti-GD$_3$ antibody KM-641 reacted only with GD$_3$, thus showing no changes in the reaction specificity by the chimera formation.

9. Reactivity of Anti-GD$_3$ Chimera Antibody KM-871 by Fluorescent Antibody Technique The cultured human malignant melanoma SK-MEL-28 (ATCC HTB72) and G361 cells (JCRB) both of which produced ganglioside GD$_3$ were placed in a microtube (Treff) to give a cell number of 1×10$^6$ cells per tube and washed by centrifugation (1,200 rpm, 5 minutes) with PBS. 50 μl of anti-GD$_3$ chimera antibody EM-871 (10 μg/ml) was added to the microtube and the mixture was allowed to react at 4° C. for 30 minutes. Thereafter, the cells were washed three times by centrifugation (1,200 rpm, 5 minutes) with PBS, then 20 μl of fluorescein isocyanate-labeled Protein A (Boehringer Mannheim-Yamanouchi, 30-fold diluted) was added and, after stirring, the mixture was allowed to react at 4° C. for 30 minutes. Thereafter, the cells were washed three times by centrifugation (1,200 rpm, 5 minutes) with PBS, further suspended in PBS, and submitted for analysis using FCS-1 flow cell sorter (Nippon Bunko).

Control tests without the addition of KM-871 were performed by the same analytical procedure as mentioned above.

Figure 32A:
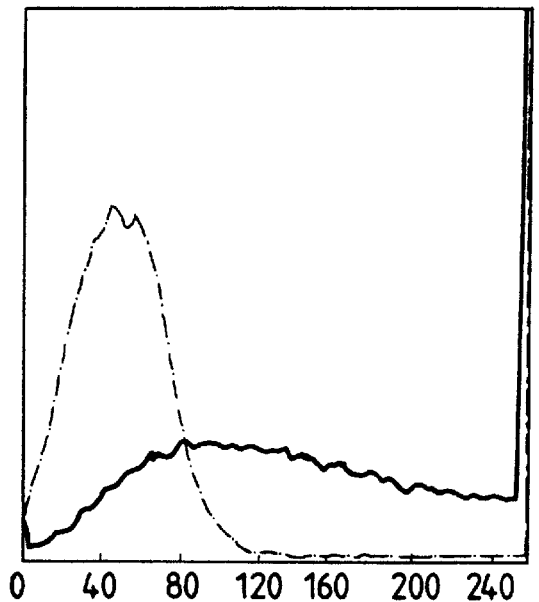
FIG. 32 is a graph showing reactivity of anti-GD$_3$ chimera antibody KM-871 with ganglioside GD$_3$-positive G361 and SK-MEL-28 cells measured by fluorescent antibody technique with the cell number on the ordinate and the fluorescence intensity on the abscissa. A dotted line shows reactivity in the absence of the antibody, while a solid line shows reactivity in the presence of KM-871.
Figure 32B:
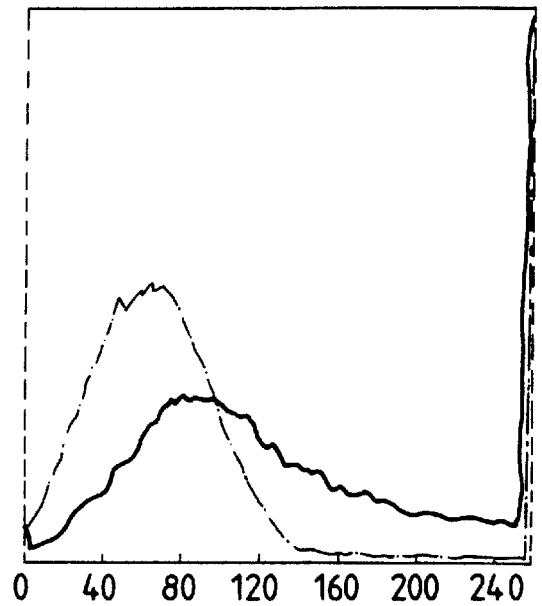

The results are shown in FIG. 32. The fluorescence intensity peak for EM-871 showed shifting to the right (increased fluorescence intensity) as compared with the control, indicating that this antibody had reacted directly with ganglioside GD, on the surface of the SK-MEL-28 and G361 cells.

10. In vitro Antitumor Effect of Anti-GD3 Chimera Antibody KM-871 (Complement-dependent Cytotoxicity:CDC)

(a) Preparation of Target Cells

Suspensions of the target cells, namely SK-MEL-28 cells and G361 cells, in RPMI-1640 medium supplemented with 10% FCS were respectively adjusted to a cell concentration of 1×10$^7$ cells/ml, Na$_2$$^{51}$CrO$_4$ was added to a concentration of 100 μCi/1×10$^7$ cells, reaction was performed at 37° C. for 1 hour and, thereafter, the cells were washed three times with the medium. The cells were allowed to stand in the medium at 4° C. for 30 minutes for spontaneous dissociation and then centrifuged (1,200 rpm, 5 minutes), and the medium was added to adjust the cell concentration to 4×10$^6$ cells/ml.

(b) Preparation of Complement

Serum from three healthy subjects were mixed to sere as a source of human complement.

(c) CDC Activity Measurement

To U-bottomed 96-well plates was added anti-$GD_3$ chimera antibody KM-871 or anti-$GD_3$ mouse antibody KM-641 to final concentrations within the range of. 0.05 µg/ml to 50 µg/ml. To each well were added 2×10⁵ target cells. Reaction was performed at room temperature for 1 hour. The supernatants were removed by centrifugation (1,200 rpm, 5 minutes), the complement solution prepared as described above under (b) was added in 150-µl portions (final concentration of 15 v/v %), and reaction was performed at 37° C. for 1 hour. After centrifugation (1,200 rpm, 5 minutes), the amount of $^{51}Cr$ in each supernatant was determined using a γ-counter. The amount of $^{51}Cr$ resulting from spontaneous dissociation was determined by adding to target cells the medium alone in place of the antibody and complement solution and determining the amount of $^{51}Cr$ in the supernatant in the same manner as described above. The total amount of free $^{51}Cr$ was determined by adding 5 N sodium hydroxide in place of the antibody and complement solution, proceeding as described above, and determining the amount of $^{51}Cr$ in the supernatant.

The CDC activity was calculated as follows:

$$\text{CDC activity (\%)} = \frac{\text{Amount of }^{51}Cr \text{ in sample supernatent} - \text{Amount of }^{51}Cr \text{ resulting from spontaneous dissociation}}{\text{Total amount of free }^{51}Cr - \text{Amount of }^{51}Cr \text{ resulting from spontaneous dissociation}} \times 100$$

Figure 33A:
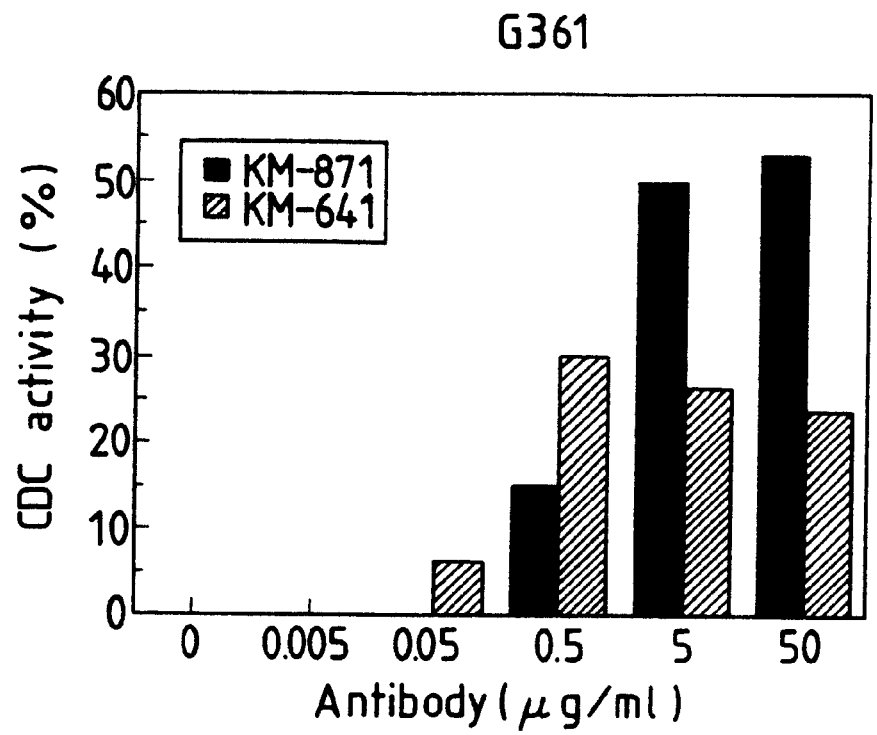
FIG. 33 is a graph showing complement-dependent cytotoxicity (CDC) of anti-GD$_3$ chimera antibody KM-871 and anti-GD$_3$ mouse antibody KM-641 against ganglioside GD$_3$-positive G361 and SK-MEL-28 cells with cytotoxicity on the ordinate and an antibody concentration on the abscissa. A blackened bar shows CDC activity of KM-871, while a striped bar shows that of KM-641.
Figure 33B:
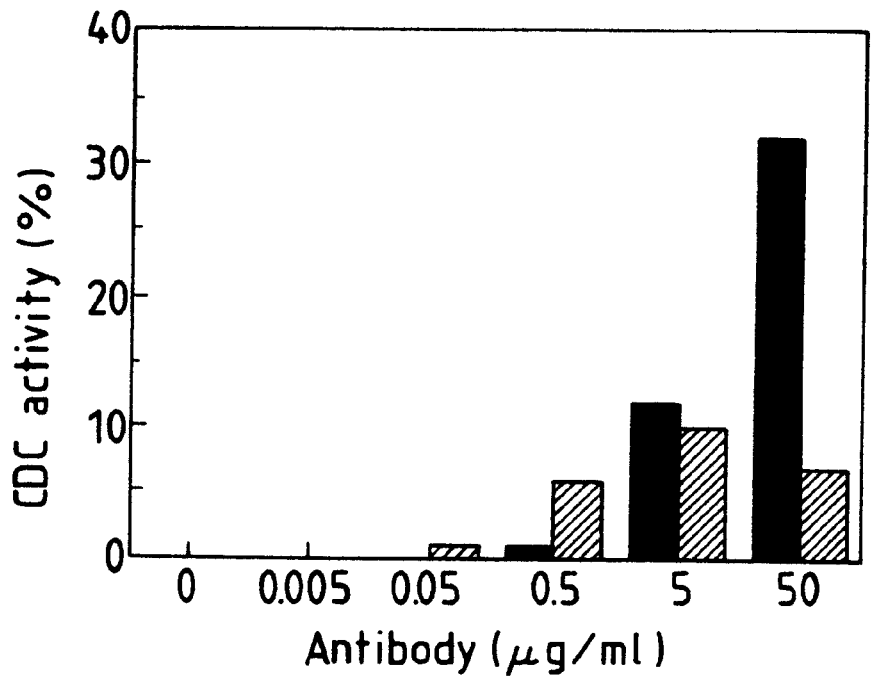

The results are shown in FIG. 33. It was found from the results that chimera antibody KM-871 showed strong cytotoxicity against the SK-MEL-28 and G361 cells as compared to mouse antibody KM-641, which indicates that chimera antibody KM-871 would be clinically more useful than mouse antibody KM-641.

11. In vitro Antitumor Effect of Anti-$GD_3$ Chimera Antibody KM-871 (Antibody-dependent Cell-mediated Cytotoxicity:ADCC)

(a) Preparation of Target Cells

The target SK-MEL-28 and G361 cells were prepared in the same manner as described above under 10 (a).

(b) Preparation of Effector Cells 50 ml of human venous blood was collected, 0.5 ml of heparin sodium (Takeda Chemical Industries, 1,000 units/ml) was added, and the mixture was stirred gently and then centrifuged (1,500 to 1,800 g, 15 minutes) using Polymorphprep (Nycomed Pharma AS). The layer of lymphocytes and polymorphonuclear leukocytes was separated, and the cells were washed three times by centrifugation (1,500 to 1,800 g, 15 minutes) with PRMI-1640 medium and suspended in RPMI-1640 medium supplemented with 10% FCS (5×10⁶ cells/ml) for use as effector cells.

(c) ADCC Activity Measurement

To U-bottomed 96-well plates was added anti-$GD_3$ chimera antibody KM-871 or anti-$GD_3$ mouse antibody KM-641 in 50-µl portions to final concentrations of 10 µg/ml. To each well were added 100 µl of target cells (2×10⁵ cells) and 50 µl of effector cells (5×10⁵ cells) so that the ratio of effector cells to target cells should be 50:1 or 100:1. Reaction was performed at 37° C. for 4 hours, followed by centrifugation (1,200 rpm, 5 minutes). The amount of $^{51}Cr$ in each supernatant was determined using a γ-counter. The amount of $^{51}Cr$ resulting from spontaneous dissociation was determined by adding to target cells the medium alone in place of the antibody and effector cells and measuring the amount of $^5Cr$ in the supernatant in the same manner as described above. The total amount of free $^{51}Cr$ was determined by adding 5 N sodium hydroxide in place of the antibody and effector cells, proceeding as described above, and determining the amount of $^{51}Cr$ in the supernatant.

The ADCC activity was calculated as follows:

$$\text{ADCC activity (\%)} = \frac{\text{Amount of }^{51}Cr \text{ in sample supernatent} - \text{Amount of }^{51}Cr \text{ resulting from spontaneous dissociation}}{\text{Total amount of free }^{51}Cr - \text{Amount of }^{51}Cr \text{ resulting from spontaneous dissociation}} \times 100$$

As a control, the medium was added in place of the antibodies, the procudure mentioned above was followed, and the amount of $^{51}Cr$ in the control supernatant was determined for ADCC activity calculation.

Figure 34:
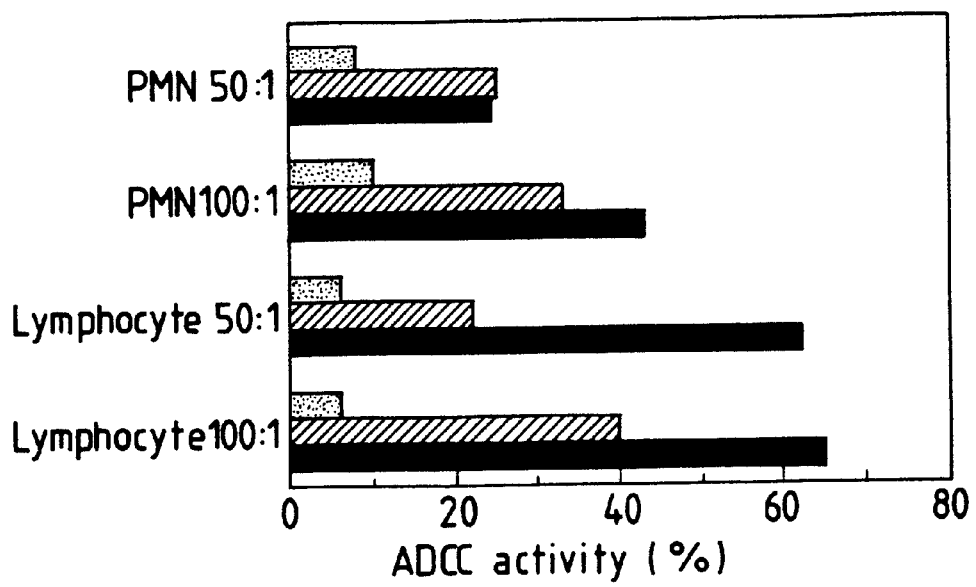
FIG. 34 is a graph showing antibody-dependent cell-mediated cytotoxicity (ADCC) of KM-871 and KM-641 against ganglioside GD$_3$-positive cell G361 with a ratio of effector cells to target cells on the ordinate and ADCC activity on the abscissa. A blackened bar shows ADCC activity of KM-871, a dotted bar shows ADCC activity of KM-641 and a striped bar shows control (in the absence of the antibody). PMN means polymorphonuclear leukocyte.

The results are shown in FIG. 34. In both cases of using lymphocytes and polymorphonuclear leukocytes as effector cells, chimera antibody KM-871 showed strong antibody-dependent cell-mediated cytotoxicity against the G361 cells as compared to mouse antibody KM-641, which indicates that chimera antibody KM-871 would be clinically more useful than mouse antibody K-641.

12. In vivo Therapeutic Effect of Anti-$GD_3$ Chimera Antibody KM-871 (Therapeutic Effect on Transplanted Tumors)

Human malignant melanoma G361 cells (1×10⁷ cells) were intracutaneously transplanted to abdominal parts of Balb/c nu/nu mice (5 to 7 aminals/group). Anti-$GD_3$ chimera antibody KM-871 (100 µg/animal) was intravenously administered into mice four times starting from the next day of the transplantation of the tumor cells. To the mice of the control group, 100 µg of anti-$GD_3$ mouse antibody KM-641 or anti-Sialyl Le$^a$ monoclonal antibody AMC-462 (ECACC 86050801) was intravenously administered five times starting from the day of the transplantation. The therapeutic effect on transplanted tumor cells was determined in terms of tumor size (volume) calculated by the following equation.

$$\text{Tumor size (mm}^3\text{)} = 0.4 \times a \times b^1$$

a: major axis b: minor axis

Figure 35:
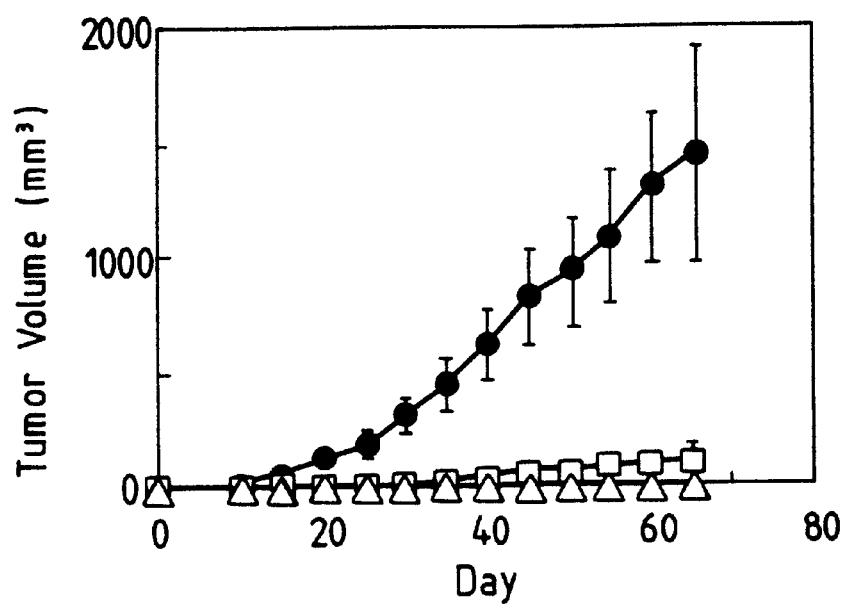
FIG. 35 is a graph showing therapeutic effect of KM-871 on transplanted tumors with the tumor size on the ordinate and days after transplantation of tumors on the abscissa, in which closed circle shows effect of anti-Sialyl Le$^2$ monoclonal antibody AMC-462, open square shows that of KM-641 and open triangle shows that of KM-871.

The results are shown in FIG. 35. As shown in FIG. 35, remarkable growth of tumors was observed in the control group to which AMC-462 was administered, while the growth of tumors was significantly suppressed in the group to which KM-641 was administered. KM-871 showed further stronger therapeutic effect so that the establishment of tumors was completely inhibited 65 days after the transplantation.

Reference Example 1

(1) Preparation of Antigen

In 30 ml of chloroform/methanol (2/1) solution were dissolved 5 µg of ganglioside $GD_3$ having NeuAcα2→8NeuAcα2→3Gal sugar chain on its non-reducing end (Iatron), 0.5 µmol of dipalmitoylphosphatidylcholine (Sigma Chemical Co.), 0.5 μmol of cholesterol (Nakalai Tesque), 0.05 μmol of dipalmitoylphosphatidylic acid (Sigma Chemical Co.) and 2.5 μg of Lipid A (Funakoshi Pharmaceutical Co., Ltd.). The thus prepared solution was warmed at 45° C. to remove solvents, thereby obtaining a uniform lipid thin film. After completely removing solvents by sacking the film for 1 hour using a vacuum pump, the resulting film was mixed with 0. 5 ml of PBS solution and stirred at 45° C. to obtain an antigen solution.

(2) Preparation of Antibody-producing Cells

Mice was immunized by administering 0.5 ml of the antigen solution obtained in the above step (1) into the caudal vein once every week for 7 weeks. For further immunization, ganglioside $GD_3$-positive SK-MEL-28 (ATCC HTB 72) cells ($1 \times 10^7$ cells) were intraperitoneally administered once every week for three weeks. On the third day after the last administration, spleen cells were prepared from each mouse for use in the following cell fusion.

(3) Preparation of Mouse Myeloma Cells

A mouse myeloma cell line P3-U1 having 8-azaguanine resistance was cultured in normal medium (RPMI1640 medium containing 10% fetal calf serum (FCS)) to obtain $2 \times 10^7$ or more cells for use in the following cell fusion as parent cells.

(4) Preparation of Hybridoma

The spleen cells and myeloma cells obtained in the above steps (2) and (3), respectively, were used in ratio of 10:1 and subjected to cell fusion in accordance with the aforementioned procedure. After culturing at 37° C. for 14 days in HAT medium (prepared by supplementing normal medium with hypoxanthin ($10^{-4}$ M), thymidine ($1.5 \times 10^{-5}$ M) and aminopterine ($4 \times 10^{-7}$ M)) under an atmosphere of 5% $CO_2$, fused cells were selected and cultured in HT medium (HAT medium minus aminopterine). Then, active wells were selected by assaying the antibody titers against ganglioside $GD_3$, and after changing to normal medium, cloning was repeated twice. Thereafter, hybridomas which showed specific reaction with ganglioside $GD_3$ were selected by enzyme immunoassay or immunohistological evaluation (ABC method). That is, 2 ng of ganglioside $GM_3$ (purified from dog erythrocytes in accordance with the method of Nores et al., J. Immunol., 139, 3171 (1987)) and 2 ng of ganglioside $GD_3$ (Iatron) were dissolved in 2 ml ethanol solution containing 5 ng of phosphatidylcholine (Sigma Chemical Co.) and 2.5 ng of cholesterol (Sigma Chemical Co.). The thus prepared solution was distributed in 20-μl portions into wells of a 96 well microtiter plate (Flow Laboratories), air-dried and then subjected to blocking using 1% BSA-PBS solution. Each of the resulting hybridoma culture supernatant was distributed in 50-μl portions into the plate wells carrying a ganglioside $GD_3$ adsorbed and the plate carrying ganglioside $GM_3$ adsorbed thereon, and the reaction was allowed to proceed at 4° C. for 18 hours.

After the reaction, a hybridoma strain capable of producing mouse monoclonal antibody specifically reactive with ganglioside $GD_3$ but not with ganglioside $GM_3$ were selected in accordance with the known method (Cancer Res., 46, 4438 (1986)). This mouse monoclonal antibody was named "mouse monoclonal antibody KM-641", and the hybridoma which produces this antibody was named "hybridoma KM-641". The hybridoma KM-641 has been deposited on Sep. 27, 1990, with Fermentation Research Institute, Agency of Industrial Science and Technology 1–3, Higashi 1 chome, Tsukuba-shi, Ibaraki, JAPAN, under the Budapest Treaty and has been assigned the designation as FERM BP-3116.

The present invention provides a process for the production of humanized chimera antibody wherein the chimera antibody can be produced easily without changing any one of amino acids of its mouse antibody variable region, as well as a humanized chimera antibody specific for ganglioside $GD_3$.

While the invention has been described in detail and with reference to specific embodiments thereof, it will be apparent to one skilled in the art that various changes and modifications can be made therein without departing from the spirit and scope of the invention.

What is claimed is:

1. A polypeptide comprising the amino acid sequence of residues 11 to 129 defined in SEQ ID NO:18.

2. A polypeptide comprising the amino acid sequence of residues 21 to 127 defined in SEQ ID NO:19.

* * * * *